United States Patent
Das et al.

(10) Patent No.: US 9,682,977 B2
(45) Date of Patent: Jun. 20, 2017

(54) BICYCLIC HETEROARYL INDOLE ANALOGUES USEFUL AS ROR GAMMA MODULATORS

(71) Applicant: Glenmark Pharmaceuticals S.A., La Chaux-de-Fonds (CH)

(72) Inventors: Sanjib Das, West Bengal (IN); Sachin Sundarlal Chaudhari, Navi Mumbai (IN); Abraham Thomas, Navi Mumbai (IN); Shailesh Ramesh Pardeshi, Maharashtra (IN); Vishal Govindrao Deshmukh, Maharashtra (IN); Prashant Dilip Wadekar, Maharashtra (IN); Neelima Khairatkar-Joshi, Thane (IN); Daisy Manish Shah, Mumbai (IN); Malini Bajpai, Uttar Pradesh (IN)

(73) Assignee: GLENMARK PHARMACEUTICALS S.A., La Chaux-de-Fonds (CH)

( * ) Notice: Subject to any disclaimer, the term of this patent is extended or adjusted under 35 U.S.C. 154(b) by 0 days.

(21) Appl. No.: 15/103,658

(22) PCT Filed: Dec. 9, 2014

(86) PCT No.: PCT/IB2014/066720
§ 371 (c)(1),
(2) Date: Jun. 10, 2016

(87) PCT Pub. No.: WO2015/087234
PCT Pub. Date: Jun. 18, 2015

(65) Prior Publication Data

US 2016/0326163 A1  Nov. 10, 2016

(30) Foreign Application Priority Data

Dec. 10, 2013  (IN) .......................... 3853/MUM/2013
Feb. 14, 2014  (IN) ............................ 527/MUM/2014
Jul. 4, 2014   (IN) .......................... 2172/MUM/2014

(51) Int. Cl.
| | | |
|---|---|---|
| C07D 231/56 | (2006.01) |
| C07D 401/04 | (2006.01) |
| C07D 209/12 | (2006.01) |
| C07D 471/04 | (2006.01) |

(52) U.S. Cl.
CPC ......... *C07D 471/04* (2013.01); *C07D 209/12* (2013.01); *C07D 231/56* (2013.01); *C07D 401/04* (2013.01)

(58) Field of Classification Search
CPC ... C07D 231/56; C07D 401/04; C07D 209/12
See application file for complete search history.

(56) References Cited

FOREIGN PATENT DOCUMENTS

| EP | 1837329 A1 | 9/2007 |
|----|-----------|--------|
| WO | WO-2006050006 A2 | 5/2006 |
| WO | WO-2012024620 A2 | 2/2012 |
| WO | WO-2012027965 A1 | 3/2012 |
| WO | WO-2012028100 A1 | 3/2012 |
| WO | WO-2012064744 A2 | 5/2012 |
| WO | WO-2012100732 A1 | 8/2012 |
| WO | WO-2012100734 A1 | 8/2012 |
| WO | WO-2012106995 A1 | 8/2012 |
| WO | WO-2012139775 A1 | 10/2012 |
| WO | WO-2013171729 A2 | 11/2013 |

OTHER PUBLICATIONS

International Search Report issued in PCT/IB2014/066720 on Feb. 9, 2015.

*Primary Examiner* — Bruck Kifle
(74) *Attorney, Agent, or Firm* — Blank Rome LLP

(57) ABSTRACT

The present disclosure is directed to compounds of formula (I) and pharmaceutically acceptable salts thereof, wherein X, $X^1$, M, $R^2$, $R^3$, $R^4$, $R^5$, m, n, and p are as defined herein, which are active as modulators of retinoid-related orphan receptor gamma t (RORγt). These compounds prevent, inhibit, or suppress the action of RORγt and are therefore useful in the treatment of RORγt mediated diseases, disorders, syndromes or conditions such as, e.g., pain, inflammation, COPD, asthma, rheumatoid arthritis, colitis, multiple sclerosis, neurodegenerative diseases and cancer.

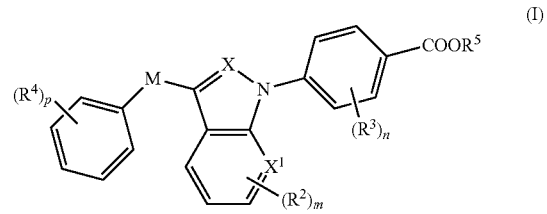

(I)

11 Claims, No Drawings

BICYCLIC HETEROARYL INDOLE ANALOGUES USEFUL AS ROR GAMMA MODULATORS

RELATED APPLICATIONS

This application is the national stage of International Patent Application No. PCT/IB2014/066720, filed 9 Dec. 2014, which claims the benefit of Indian Provisional Application Nos. 3853/MUM/2013 filed on 10 Dec. 2013; 527/MUM/2014 filed 14 Feb. 2014; and 2172/MUM/2014 filed on 4 Jul. 2014, each of which is hereby incorporated by reference in its entirety.

FIELD OF THE INVENTION

The present patent application is directed to bicyclic heteroaryl compounds which may be useful as retinoid-related orphan receptor gamma t (RORγt) modulators.

BACKGROUND OF THE INVENTION

Retinoid-related orphan receptors (RORs) are transcription factors which belong to the steroid hormone nuclear receptor super family. The ROR family consists of three members, ROR alpha (RORα), ROR beta (RORβ) and ROR gamma (RORγ), also known as NR1F1, NR1F2 and NR1F3 respectively (and each encoded by a separate gene RORA, RORB and RORC, respectively). RORs contain four principal domains shared by the majority of nuclear receptors: an N-terminal A/B domain, a DNA-binding domain, a hinge domain, and a ligand binding domain. Each ROR gene generates several isoforms which differ only in their N-terminal A/B domain. Two isoforms of RORγ, RORγ1 and RORγt (also known as RORγ2) have been identified.

RORγt is a truncated form of RORγ, lacking the first N-terminal 21 amino acids and is exclusively expressed in cells of the lymphoid lineage and embryonic lymphoid tissue inducers (Sun et al., Science, 2000, 288, 2369-2372; Eberl et al., Nat Immunol., 2004, 5: 64-73) in contrast to RORγ which is expressed in multiple tissues (heart, brain, kidney, lung, liver and muscle).

RORγt has been identified as a key regulator of Th17 cell differentiation. Th17 cells are a subset of T helper cells which produce IL-17 and other proinflammatory cytokines and have been shown to have key functions in several mouse autoimmune disease models including experimental autoimmune encephalomyelitis (EAE) and collagen-induced arthritis (CIA). In addition, Th17 cells have also been associated in the pathology of a variety of human inflammatory and autoimmune disorders including multiple sclerosis, rheumatoid arthritis, psoriasis, Crohn's disease and asthma (Jetten et al., Nucl. Recept. Signal, 2009, 7:e003; Manel et al., Nat. Immunol., 2008, 9, 641-649). The pathogenesis of chronic autoimmune diseases including multiple sclerosis and rheumatoid arthritis arises from the break in tolerance towards self-antigens and the development of auto-aggressive effector T cells infiltrating the target tissues. Studies have shown that Th17 cells are one of the important drivers of the inflammatory process in tissue-specific autoimmunity (Steinman et al., J. Exp. Med., 2008, 205: 1517-1522; Leung et al., Cell. Mol. Immunol., 2010 7: 182-189). Th17 cells are activated during the disease process and are responsible for recruiting other inflammatory cells types, especially neutrophils, to mediate pathology in the target tissues (Korn et al., Annu. Rev. Immunol., 2009, 27:485-517) and RORγt has been shown to play a critical role in the pathogenic responses of Th17 cells (Ivanov et al., Cell, 2006 126: 1121-1133). RORγt deficient mice have shown no Th17 cells and also resulted in amelioration of EAE. The genetic disruption of RORγ in a mouse colitis model also prevented colitis development (Buonocore et al., Nature, 2010, 464: 1371-1375). The role of RORγt in the pathogenesis of autoimmune or inflammatory diseases has been well documented in the literature. (Jetten et al., Adv. Dev. Biol., 2006, 16:313-355; Meier et al. Immunity, 2007, 26:643-654; Aloisi et al., Nat. Rev. Immunol., 2006, 6:205-217; Jager et al., J. Immunol., 2009, 183:7169-7177; Serafmi et al., Brain Pathol., 2004, 14: 164-174; Magliozzi et al., Brain, 2007, 130: 1089-1104; Barnes et al., Nat. Rev. Immunol., 2008, 8: 183-192).

In addition, RORγt is also shown to play a crucial role in other non-Th17 cells, such as mast cells (Hueber et al., J Immunol., 2010, 184: 3336-3340). RORγt expression and secretion of Th17-type of cytokines has also been reported in NK T-cells (Eberl et al., Nat. Immunol., 2004, 5: 64-73) and gamma-delta T-cells (Sutton et al, Nat. Immunol., 2009, 31: 331-341; Louten et al., J Allergy Clin. Immunol., 2009, 123: 1004-1011), suggesting an important function for RORγt in these cells.

PCT Publication Nos. WO 2012/139775, WO 2012/027965, WO 2012/028100, WO 2012/100732, WO 2012/100734, WO2012/064744 and WO 2013/171729 disclose heterocyclic compounds which are modulators of retinoid-related orphan receptor gamma (RORγ) receptor activity.

In view of the above, a need exists for new therapeutic agents that modulate the activity of RORγt and thus will provide new methods for treating diseases or condition associated with the modulation of RORγt.

The present application is directed to compounds that are modulators of the RORγt receptor.

SUMMARY OF THE INVENTION

In one aspect, the present invention relates to compound of formula (I)

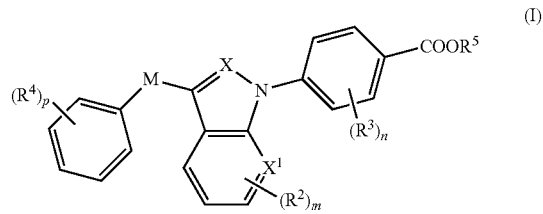

or a pharmaceutically acceptable salt thereof,
wherein,
M is selected from —O— and —C(O)—;
X is selected from N and CH;
$X^1$ is selected from N and CH;
each occurrence of $R^2$ is independently selected from halogen, hydroxyl and —CON(CH$_3$)$_2$;
each occurrence of $R^3$ is independently selected from halogen and hydroxyl;
each occurrence of $R^4$ is independently selected from halogen, $C_{1-8}$alkyl, halo$C_{1-8}$alkyl and $C_{3-6}$cycloalkyl;
$R^5$ is selected from hydrogen and $C_{1-4}$alkyl;
'm' is 0, 1, 2 or 3;
'n' is 0, 1, 2 or 3; and
'p' is 0, 1, 2, 3 or 4.

The compounds of formula (I) may involve one or more embodiments. Embodiments of formula (I) include compounds of formula (Ia) and formula (Ib) as described hereinafter. It is to be understood that any of the embodiments described below are illustrative of the present invention and are not intended to limit the claims to the specific embodiments exemplified. It is also to be understood that the embodiments defined herein may be used independently or in conjunction with any definition, any other embodiment defined herein. Thus the invention contemplates all possible combinations and permutations of the various independently described embodiments. For example, the invention provides compounds of formula (I) as defined above wherein M is —O— (according to an embodiment defined below), X is N (according to another embodiment defined below) and $R^3$ is F (according to yet another embodiment defined below).

According to one embodiment, specifically provided are compounds of formula (I), in which M is —O—.

According to another embodiment, specifically provided are compounds of formula (I), in which M is —C(O)—.

According to yet another embodiment, specifically provided are compounds of formula (I), in which X is N.

According to yet another embodiment, specifically provided are compounds of formula (I), in which X is CH.

According to yet another embodiment, specifically provided are compounds of formula (I), in which $X^1$ is N.

According to yet another embodiment, specifically provided are compounds of formula (I), in which $X^1$ is CH.

According to yet another embodiment, specifically provided are compounds of formula (I), in which $X^1$ is N or CH.

According to yet another embodiment, specifically provided are compounds of formula (I), in which each occurrence of $R^2$ is independently halogen (e.g. F, Cl or Br) or —CON(CH$_3$)$_2$.

According to yet another embodiment, specifically provided are compounds of formula (I), in which each occurrence of $R^2$ is independently F or —CON(CH$_3$)$_2$.

According to yet another embodiment specifically provided are compounds of formula (I), in which 'm' is 0 or 1.

According to yet another embodiment, specifically provided are compounds of formula (I), in which each occurrence of $R^2$ is independently F or CON(CH$_3$)$_2$ and 'm' is 0 or 1.

According to yet another embodiment, specifically provided are compounds of formula (I), in which each occurrence of $R^3$ is independently halogen (e.g. F, Cl or Br).

According to yet another embodiment, specifically provided are compounds of formula (I), in which 'n' is 0 or 1.

According to yet another embodiment, specifically provided are compounds of formula (I), in which each occurrence of $R^3$ is F.

According to yet another embodiment, specifically provided are compounds of formula (I), in which each occurrence of $R^3$ is F and 'n' is 0 or 1.

According to yet another embodiment, specifically provided are compounds of formula (I), in which each occurrence of $R^4$ is independently halogen (e.g. F, Cl or Br), $C_{1-8}$alkyl (e.g. methyl or ethyl), halo$C_{1-8}$alkyl (e.g. CHF$_2$ or CF$_3$) or $C_{3-6}$cycloalkyl (e.g. cyclopropyl).

According to yet another embodiment specifically provided are compounds of formula (I), in which 'p' is 0, 1 or 2.

According to yet another embodiment, specifically provided are compounds of formula (I), in which each occurrence of $R^4$ is independently halogen (e.g. F, Cl or Br), $C_{1-4}$alkyl (e.g. methyl or ethyl), halo$C_{1-4}$alkyl (e.g. CHF$_2$ or CF$_3$) or $C_{3-6}$cycloalkyl (e.g. cyclopropyl); and 'p' is 0, 1 or 2.

According to yet another embodiment, specifically provided are compounds of formula (I), in which each occurrence of $R^4$ is independently F, Cl, CH$_3$, CF$_3$, CHF$_2$ or cyclopropyl.

According to yet another embodiment, specifically provided are compounds of formula (I), in which each occurrence of $R^4$ is independently F, Cl, CH$_3$, CF$_3$, CHF$_2$ or cyclopropyl; and 'p' is 0, 1 or 2.

According to yet another embodiment, specifically provided are compounds of formula (I), in which $R^4$ is a present on the phenyl ring at the 2-position or the 3-position, and optionally one or more at other positions (e.g., $R^4$ is a present on the phenyl ring at the 2-position and the 3-position, the 2-position and the 4-position, the 2-position and the 5-position, the 2-position and the 6-position, the 3-position and the 4-position, the 3-position and the 5-position, or the 3-position and the 6-position).

According to yet another embodiment, specifically provided are compounds of formula (I), in which $R^4$ is present on the phenyl ring at the 2-position and the 6-position.

According to yet another embodiment, specifically provided are compounds of formula (I), in which

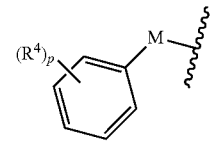

is phenoxy, 2-methylphenoxy, 3-methylphenoxy, 2-(trifluoromethyl)phenoxy, 2,6-dichlorophenoxy, 2-chloro-6-(trifluoromethyl)phenoxy, 4-chloro-2-(trifluoromethyl)phenoxy, 2-chloro-6-(difluoromethyl)phenoxy, 2-chloro-6-cyclopropylphenoxy, benzoyl, 2-fluorobenzoyl, 2-chlorobenzoyl, 2,6-dichlorobenzoyl, 2,6-difluorobenzoyl, 2-chloro-6-(trifluoromethyl)benzoyl or (2-chloro-6-cyclopropylphenyl)carbonyl.

According to yet another embodiment, specifically provided are compounds of formula (I), in which

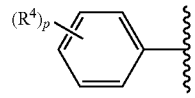

is phenyl, 2-fluorophenyl, 2-methylphenyl, 3-methylphenyl, 2-(trifluoromethyl)phenyl, 2,6-dichlorophenyl, 2,6-difluorophenyl, 2-chloro-6-(trifluoromethyl)phenyl, 4-chloro-2-(trifluoromethyl)phenyl, 2-chloro-6-(difluoromethyl)phenyl or 2-chloro-6-cyclopropylphenyl.

According to yet another embodiment, specifically provided are compounds of formula (I), in which $R^5$ is hydrogen.

According to yet another embodiment, specifically provided are compounds of formula (I), in which $R^5$ is $C_{1-4}$alkyl (e.g. methyl, ethyl, n-propyl, isopropyl or n-butyl).

According to yet another embodiment, specifically provided are compounds of formula (I), in which $R^5$ is hydrogen, —CH$_3$, —CH$_2$CH$_3$, —CH$_2$CH$_2$CH$_3$, —CH$_2$CH(CH$_3$)$_2$ or —CH$_2$CH$_2$CH$_2$CH$_3$.

According to yet another embodiment, specifically provided are compounds of formula (I), in which

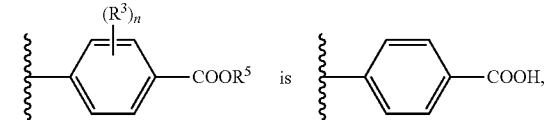

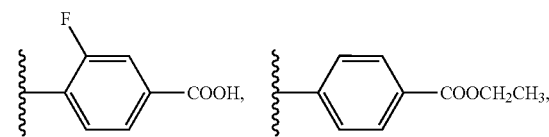

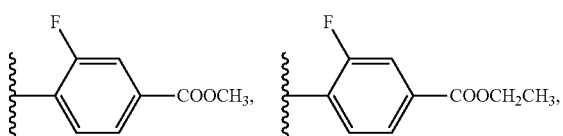

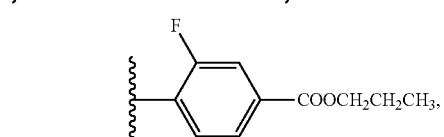

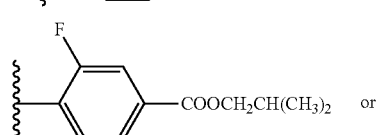

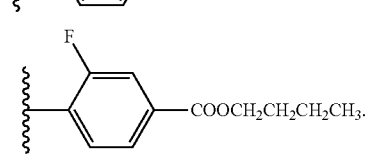

According to yet another embodiment, specifically provided are compounds of formula (I), in which

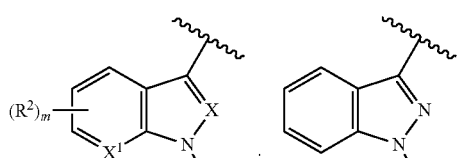

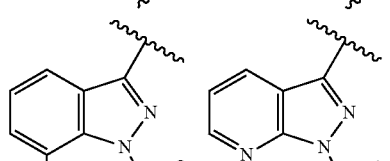

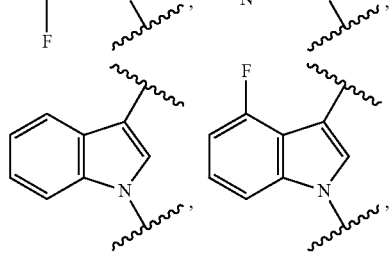

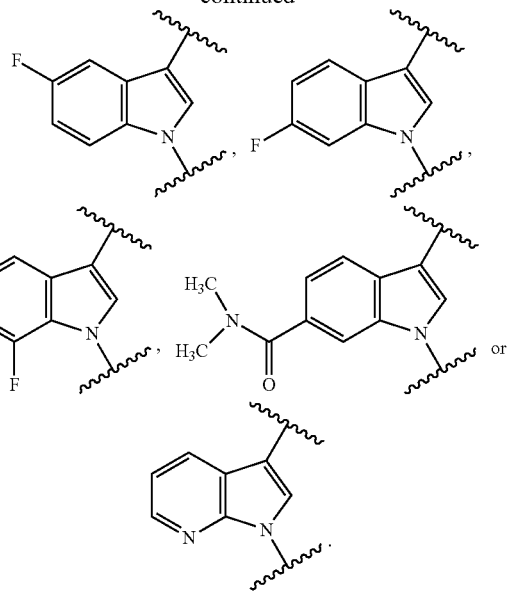

According to yet another embodiment, specifically provided are compounds of formula (I), in which
M is —O— or —C(O)—;
X is N or CH;
$X^1$ is N or CH;
each occurrence of $R^2$ is independently halogen (e.g. F, Cl or Br) or —CON(CH$_3$)$_2$;
each occurrence of $R^3$ is halogen (e.g. F, Cl or Br);
each occurrence of $R^4$ is independently halogen (e.g. F, Cl or Br), C$_{1-8}$alkyl (e.g. methyl or ethyl), haloC$_{1-8}$alkyl (e.g. CHF$_2$ or CF$_3$) or C$_{3-6}$cycloalkyl (e.g. cyclopropyl);
$R^5$ is hydrogen or C$_{1-4}$alkyl (e.g. methyl, ethyl, n-propyl, isopropyl or n-butyl);
'm' is 0 or 1;
'n' is 0 or 1; and
'p' is 0, 1 or 2.

According to yet another embodiment, specifically provided are compounds of formula (I), in which
M is —O— or —C(O)—;
X is N or CH;
$X^1$ is N or CH;
each occurrence of $R^2$ is independently F or —CON(CH$_3$)$_2$;
each occurrence of $R^3$ is F;
each occurrence of $R^4$ is independently F, Cl, CH$_3$, CHF$_2$, CF$_3$ or cyclopropyl;
$R^5$ is hydrogen, —CH$_3$, —CH$_2$CH$_3$, —CH$_2$CH$_2$CH$_3$, —CH$_2$CH(CH$_3$)$_2$ or —CH$_2$CH$_2$CH$_2$CH$_3$;
'm' is 0 or 1;
'n' is 0 or 1; and
'p' is 0, 1 or 2.

According to yet another embodiment, specifically provided are compounds of formula (I), in which
X is N or CH;
$X^1$ is N or CH;
each occurrence of $R^2$ is independently F or —CON(CH$_3$)$_2$;
each occurrence of $R^3$ is F;
$R^5$ is hydrogen, —CH$_3$, —CH$_2$CH$_3$, —CH$_2$CH$_2$CH$_3$, —CH$_2$CH(CH$_3$)$_2$ or —CH$_2$CH$_2$CH$_2$CH$_3$;
'm' is 0 or 1;
'n' is 0 or 1; and

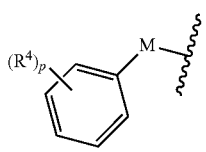

is phenoxy, 2-methylphenoxy, 3-methylphenoxy, 2-(trifluoromethyl)phenoxy, 2,6-dichlorophenoxy, 2-chloro-6-(trifluoromethyl)phenoxy, 4-chloro-2-(trifluoromethyl)phenoxy, 2-chloro-6-(difluoromethyl)phenoxy, 2-chloro-6-cyclopropylphenoxy, benzoyl, 2-fluorobenzoyl, 2-chlorobenzoyl, 2,6-dichlorobenzoyl, 2,6-difluorobenzoyl, 2-chloro-6-(trifluoromethyl)benzoyl or (2-chloro-6-cyclopropylphenyl)carbonyl.

According to yet another embodiment, specifically provided are compounds of formula (I), in which

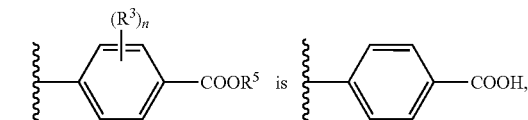

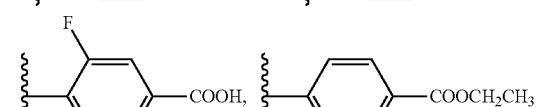

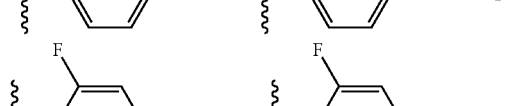

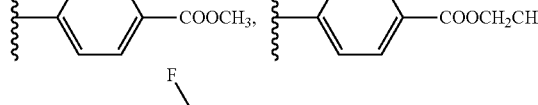

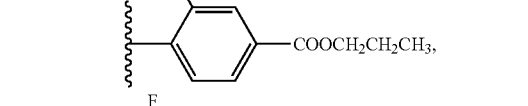

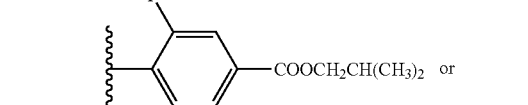

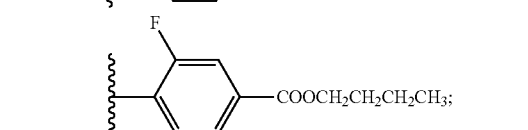

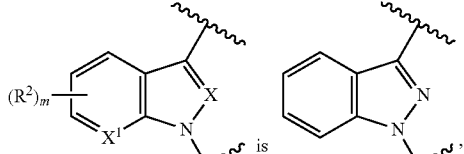

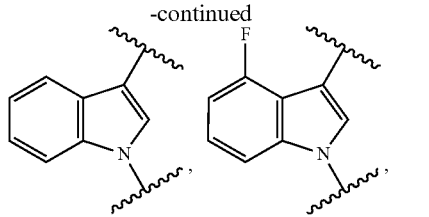

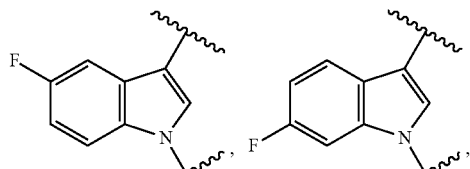

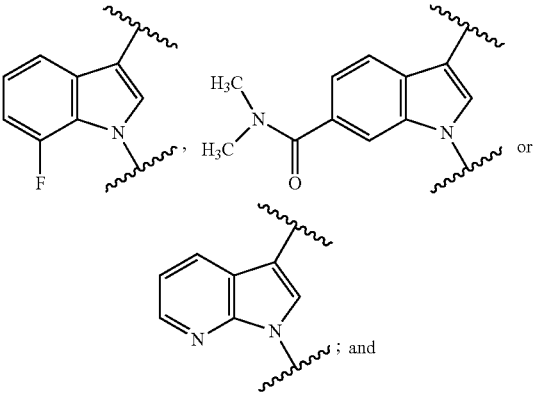

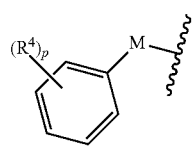

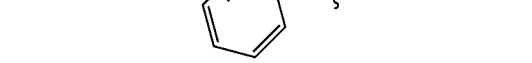

is phenoxy, 2-methylphenoxy, 3-methylphenoxy, 2-(trifluoromethyl)phenoxy, 2,6-dichlorophenoxy, 2-chloro-6-(trifluoromethyl)phenoxy, 4-chloro-2-(trifluoromethyl)phenoxy, 2-chloro-6-(difluoromethyl)phenoxy, 2-chloro-6-cyclopropylphenoxy, benzoyl, 2-fluorobenzoyl, 2-chlorobenzoyl, 2,6-dichlorobenzoyl, 2,6-difluorobenzoyl, 2-chloro-6-(trifluoromethyl)benzoyl or (2-chloro-6-cyclopropylphenyl)carbonyl.

According to an embodiment, specifically provided are compounds of formula (I) that exhibit an $IC_{50}$ value with respect to RORγt activity of less than about 500 nM, preferably less than about 100 nM, more preferably less than about 50 nM.

Further embodiments relating to groups M, X, $X^1$, $R^2$, $R^3$, $R^4$, $R^5$, m, n and p (and groups defined therein) as described above for Formula (I) are described hereinafter in relation to the compounds of formula (Ia) or Formula (Ib). It is to be understood that these embodiments are not limited to use in conjunction with formula (Ia) or (Ib), but apply independently and individually to the compounds of formula (I). For example, in an embodiment described hereinafter, the invention provides compounds of formula (Ia) or formula (Ib), in which $R^3$ is F and consequently there is also provided a compound of formula (I) in which $R^3$ is F.

The invention also provides a compound of formula (Ia), which is an embodiment of a compound of formula (I).

Accordingly the invention provides compound of formula (Ia)

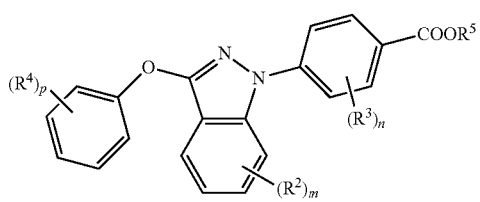

or a pharmaceutically acceptable salt thereof,
wherein,
each occurrence of $R^2$ is independently selected from halogen, hydroxyl and —CON(CH$_3$)$_2$;
each occurrence of $R^3$ is independently selected from halogen and hydroxyl;
each occurrence of $R^4$ is independently selected from halogen, C$_{1-8}$alkyl, haloC$_{1-8}$alkyl and C$_{3-6}$cycloalkyl;
$R^5$ is selected from hydrogen and C$_{1-4}$alkyl;
'm' is 0, 1, 2 or 3;
'n' is 0, 1, 2 or 3; and
'p' is 0, 1, 2, 3 or 4.

The compounds of formula (Ia) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition of any other embodiment defined herein. Thus, the invention contemplates all possible combinations and permutations of the various independently described embodiments. For example, the invention provides compounds of formula (Ia) as defined above wherein $R^3$ is F (according to an embodiment defined below), 'n' is 0 or 1 (according to another embodiment defined below) and 'p' is 0, 1 or 2 (according to yet another embodiment defined below).

According to one embodiment, specifically provided are compounds of formula (Ia), in which each occurrence of $R^2$ is independently halogen (e.g. F, Cl or Br).

According to another embodiment, specifically provided are compounds of formula (Ia), in which 'm' is 0 or 1.

According to yet another embodiment specifically provided are compounds of formula (Ia), in which each occurrence of $R^2$ is F; and 'm' is 0 or 1.

According to yet another embodiment specifically provided are compounds of formula (Ia), in which each occurrence of $R^3$ is independently halogen (e.g. F, Cl or Br).

According to yet another embodiment specifically provided are compounds of formula (Ia), in which 'n' is 0 or 1.

According to yet another embodiment specifically provided are compounds of formula (Ia), in which each occurrence of $R^3$ is halogen (e.g. F, Cl or Br); and 'n' is 0 or 1.

According to yet another embodiment specifically provided are compounds of formula (Ia), in which each occurrence of $R^3$ is F.

According to yet another embodiment, specifically provided are compounds of formula (Ia), in which each occurrence of $R^3$ is F; and 'n' is 0 or 1.

According to yet another embodiment, specifically provided are compounds of formula (Ia), in which each occurrence of $R^4$ is independently halogen (e.g. F, Cl or Br), C$_{1-8}$alkyl (e.g. methyl or ethyl), haloC$_{1-8}$alkyl (e.g. CHF$_2$ or CF$_3$) or C$_{3-6}$cycloalkyl (e.g. cyclopropyl).

According to yet another embodiment, specifically provided are compounds of formula (Ia), in which 'p' is 0, 1 or 2.

According to yet another embodiment, specifically provided are compounds of formula (Ia), in which each occurrence of $R^4$ is independently halogen (e.g. F, Cl or Br), C$_{1-4}$alkyl (e.g. methyl or ethyl), haloC$_{1-4}$alkyl (e.g. CHF$_2$ or CF$_3$) or C$_{3-6}$cycloalkyl (e.g. cyclopropyl); and 'p' is 0, 1 or 2.

According to yet another embodiment, specifically provided are compounds of formula (Ia), in which each occurrence of $R^4$ is independently F, Cl, CH$_3$, CHF$_2$, CF$_3$ or cyclopropyl.

According to yet another embodiment, specifically provided are compounds of formula (Ia), in which each occurrence of $R^4$ is independently F, Cl, CH$_3$, CHF$_2$, CF$_3$ or cyclopropyl; and 'p' is 1 or 2.

According to yet another embodiment, specifically provided are compounds of formula (Ia), in which $R^4$ is present on the phenyl ring at the 2-position or the 3-position, and optionally one or more other positions (e.g., $R^4$ is a present on the phenyl ring at the 2-position and the 3-position, the 2-position and the 4-position, the 2-position and the 5-position, the 2-position and the 6-position, the 3-position and the 4-position, the 3-position and the 5-position, or the 3-position and the 6-position).

According to yet another embodiment, specifically provided are compounds of formula (Ia), in which $R^4$ is present on the phenyl ring at the 2-position and the 6-position.

According to yet another embodiment, specifically provided are compounds of formula (Ia), in which

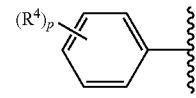

is phenyl, 2-fluorophenyl, 2-methylphenyl, 3-methylphenyl, 2-(trifluoromethyl)phenyl, 2,6-dichlorophenyl, 2,6-difluorophenyl, 2-chloro-6-(trifluoromethyl)phenyl, 4-chloro-2-(trifluoromethyl)phenyl, 2-chloro-6-(difluoromethyl)phenyl or 2-chloro-6-cyclopropylphenyl.

According to yet another embodiment, specifically provided are compounds of formula (Ia), in which $R^5$ is hydrogen.

According to yet another embodiment, specifically provided are compounds of formula (Ia), in which $R^5$ is C$_{1-4}$alkyl (e.g. methyl, ethyl, n-propyl, isopropyl or n-butyl).

According to yet another embodiment, specifically provided are compounds of formula (Ia), in which $R^5$ is hydrogen, —CH$_3$, —CH$_2$CH$_3$, —CH$_2$CH$_2$CH$_3$, —CH$_2$CH(CH$_3$)$_2$ or —CH$_2$CH$_2$CH$_2$CH$_3$.

According to yet another embodiment, specifically provided are compounds of formula (Ia), in which

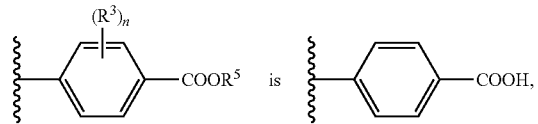

-continued

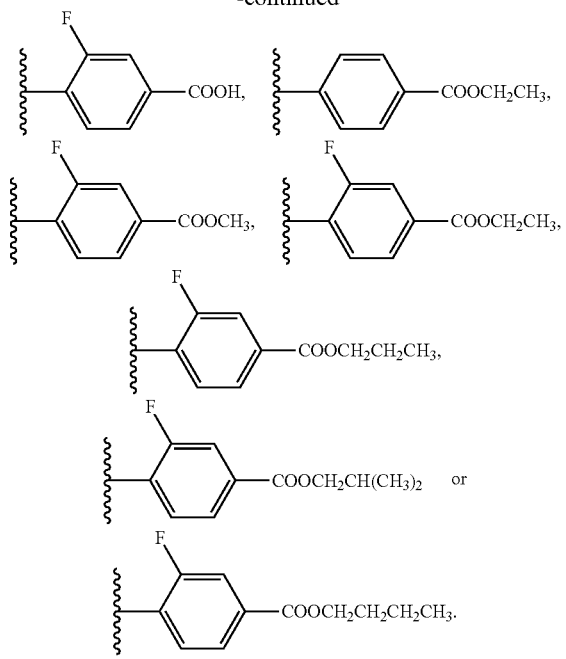

According to yet another embodiment, specifically provided are compounds of formula (Ia), in which

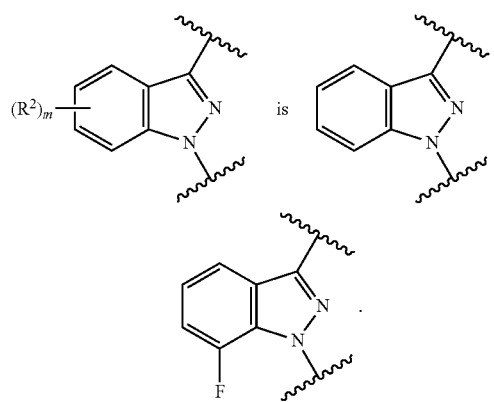

According to yet another embodiment, specifically provided are compounds of formula (Ia), in which each occurrence of $R^2$ is independently halogen (e.g. F, Cl or Br);

each occurrence of $R^3$ is independently halogen (e.g. F, Cl or Br);

each occurrence of $R^4$ is independently halogen (e.g. F, Cl or Br), $C_{1-8}$alkyl (e.g. methyl or ethyl), halo$C_{1-8}$alkyl (e.g. $CHF_2$ or $CF_3$) or $C_{3-6}$cycloalkyl (e.g. cyclopropyl);

$R^5$ is hydrogen or $C_{1-4}$alkyl (e.g. methyl, ethyl, n-propyl, isopropyl or n-butyl);

'm' is 0 or 1;

'n' is 0 or 1; and

'p' is 0, 1 or 2.

According to yet another embodiment, specifically provided are compounds of formula (Ia), in which each occurrence of $R^2$ is F;

each occurrence of $R^3$ is F;

each occurrence of $R^4$ is independently F, Cl, $CH_3$, $CHF_2$, $CF_3$ or cyclopropyl; $R^5$ is hydrogen, —$CH_3$, —$CH_2CH_3$, —$CH_2CH_2CH_3$, —$CH_2CH(CH_3)_2$ or —$CH_2CH_2CH_2CH_3$;

'm' is 0 or 1;

'n' is 0 or 1; and

'p' is 0, 1 or 2.

According to yet another embodiment, specifically provided are compounds of formula (Ia), in which each occurrence of $R^2$ is F;

each occurrence of $R^3$ is F;

$R^5$ is hydrogen, —$CH_3$, —$CH_2CH_3$, —$CH_2CH_2CH_3$, —$CH_2CH(CH_3)_2$ or —$CH_2CH_2CH_2CH_3$;

'm' is 0 or 1;

'n' is 0 or 1; and

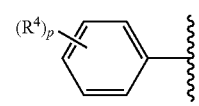

is phenyl, 2-fluorophenyl, 2-methylphenyl, 3-methylphenyl, 2-(trifluoromethyl)phenyl, 2,6-dichlorophenyl, 2,6-difluorophenyl, 2-chloro-6-(trifluoromethyl)phenyl, 4-chloro-2-(trifluoromethyl)phenyl, 2-chloro-6-(difluoromethyl)phenyl or 2-chloro-6-cyclopropylphenyl.

According to yet another embodiment, specifically provided are compounds of formula (Ia), in which

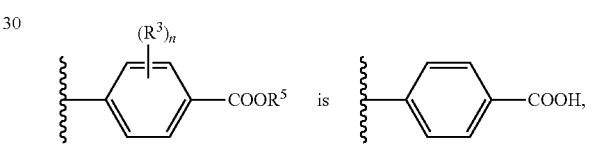

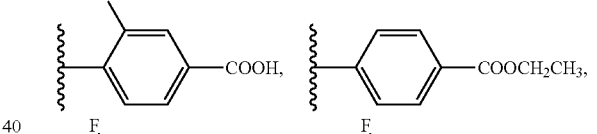

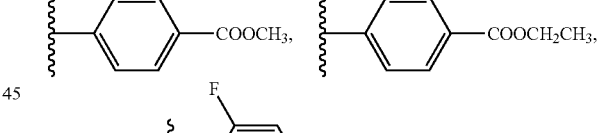

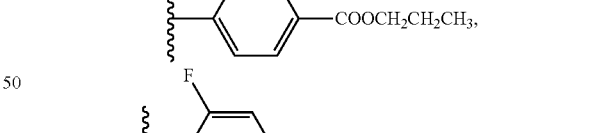

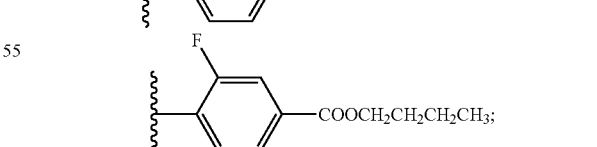

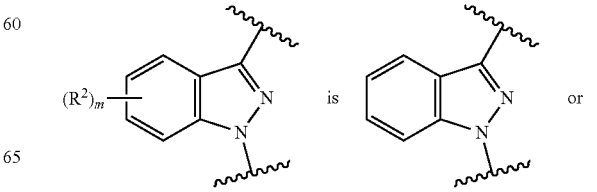

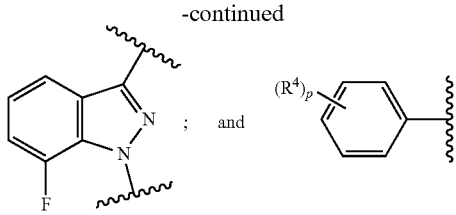

is phenyl, 2-fluorophenyl, 2-methylphenyl, 3-methylphenyl, 2-(trifluoromethyl)phenyl, 2,6-dichlorophenyl, 2,6-difluorophenyl, 2-chloro-6-(trifluoromethyl)phenyl, 4-chloro-2-(trifluoromethyl)phenyl, 2-chloro-6-(difluoromethyl)phenyl or 2-chloro-6-cyclopropylphenyl.

According to an embodiment, specifically provided are compounds of formula (Ia) that exhibit an $IC_{50}$ value with respect to RORγt activity of less than about 500 nM, preferably less than about 100 nM, more preferably less than about 50 nM.

The invention also provides a compound of formula (Ib), which is an embodiment of a compound of formula (I).

Accordingly the invention provides compound of formula (Ib)

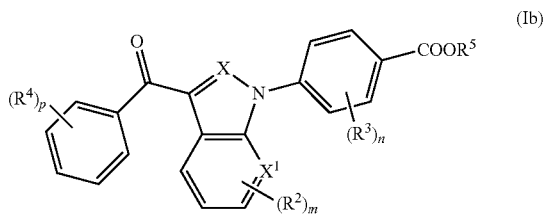

or a pharmaceutically acceptable salt thereof,
wherein,
X is selected from N and CH;
$X^1$ is selected from N and CH;
each occurrence of $R^2$ is independently selected from halogen, hydroxyl and —$CON(CH_3)_2$;
each occurrence of $R^3$ is independently selected from halogen and hydroxyl;
each occurrence of $R^4$ is independently selected from halogen, $C_{1-8}$alkyl, halo$C_{1-8}$alkyl and $C_{3-6}$cycloalkyl;
$R^5$ is selected from hydrogen and $C_{1-4}$alkyl;
'm' is 0, 1, 2 or 3;
'n' is 0, 1, 2 or 3; and
'p' is 0, 1, 2, 3 or 4.

The compounds of formula (Ib) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition of any other embodiment defined herein. Thus, the invention contemplates all possible combinations and permutations of the various independently described embodiments. For example, the invention provides compounds of formula (Ib) as defined above wherein $R^3$ is F (according to an embodiment defined below), 'n' is 0 or 1 (according to another embodiment defined below) and 'p' is 0, 1 or 2 (according to yet another embodiment defined below).

According to one embodiment, specifically provided are compounds of formula (Ib), in which X in N.

According to another embodiment, specifically provided are compounds of formula (Ib), in which X in CH.

According to yet another embodiment, specifically provided are compounds of formula (Ib), in which $X^1$ is N.

According to yet another embodiment, specifically provided are compounds of formula (Ib), in which $X^1$ is CH.

According to yet another embodiment, specifically provided are compounds of formula (Ib), in which $X^1$ is N or CH.

According to yet another embodiment, specifically provided are compounds of formula (Ib), in which each occurrence of $R^2$ is independently halogen (e.g. F, Cl or Br).

According to yet another embodiment, specifically provided are compounds of formula (Ib), in which 'm' is 0 or 1.

According to yet another embodiment specifically provided are compounds of formula (Ib), in which each occurrence of $R^2$ is F.

According to yet another embodiment, specifically provided are compounds of formula (Ib), in which each occurrence of $R^2$ is F; and 'm' is 0 or 1

According to yet another embodiment, specifically provided are compounds of formula (Ib), in which each occurrence of $R^3$ is independently halogen (e.g. F, Cl or Br).

According to yet another embodiment, specifically provided are compounds of formula (Ib), in which 'n' is 0 or 1.

According to yet another embodiment, specifically provided are compounds of formula (Ib), in which each occurrence of $R^3$ is halogen (e.g. F, Cl or Br); and 'n' is 0 or 1.

According to yet another embodiment, specifically provided are compounds of formula (Ib), in which each occurrence of $R^3$ is F.

According to yet another embodiment, specifically provided are compounds of formula (Ib), in which each occurrence of $R^3$ is F; and 'n' is 0 or 1.

According to yet another embodiment, specifically provided are compounds of formula (Ib), in which each occurrence of $R^4$ is independently halogen (e.g. F, Cl or Br), $C_{1-8}$alkyl (e.g. methyl or ethyl), halo$C_{1-8}$alkyl (e.g. $CHF_2$ or $CF_3$) or $C_{3-6}$cycloalkyl (e.g. cyclopropyl).

According to yet another embodiment, specifically provided are compounds of formula (Ib), in which 'p' is 0, 1 or 2.

According to yet another embodiment, specifically provided are compounds of formula (Ib), in which each occurrence of $R^4$ is independently halogen (e.g. F, Cl or Br), $C_{1-4}$alkyl (e.g. methyl or ethyl), halo$C_{1-4}$alkyl (e.g. $CHF_2$ or $CF_3$) or $C_{3-6}$cycloalkyl (e.g. cyclopropyl); and 'p' is 0, 1 or 2.

According to yet another embodiment, specifically provided are compounds of formula (Ib), in which each occurrence of $R^4$ is independently F, Cl, $CH_3$, $CF_3$, $CHF_2$ or cyclopropyl.

According to yet another embodiment, specifically provided are compounds of formula (Ib), in which each occurrence of $R^4$ is independently F, Cl, $CH_3$, $CF_3$, $CHF_2$ or cyclopropyl; and 'p' is 1 or 2.

According to yet another embodiment, specifically provided are compounds of formula (Ib), in which $R^4$ is present on the phenyl ring at the 2-position or the 3-position and optionally one or more other positions (e.g., $R^4$ is a present on the phenyl ring at the 2-position and the 3-position, the 2-position and the 4-position, the 2-position and the 5-position, the 2-position and the 6-position, the 3-position and the 4-position, the 3-position and the 5-position, or the 3-position and the 6-position).

According to yet another embodiment, specifically provided are compounds of formula (Ib), in which R⁴ is present on the phenyl ring at the 2-position and the 6-position.

According to yet another embodiment, specifically provided are compounds of formula (Ib), in which

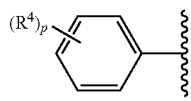

is phenyl, 2-fluorophenyl, 2-methylphenyl, 3-methylphenyl, 2-(trifluoromethyl)phenyl, 2,6-dichlorophenyl, 2,6-difluorophenyl, 2-chloro-6-(trifluoromethyl)phenyl, 4-chloro-2-(trifluoromethyl)phenyl, 2-chloro-6-(difluoromethyl)phenyl or 2-chloro-6-cyclopropylphenyl.

According to yet another embodiment, specifically provided are compounds of formula (Ib), in which R⁵ is hydrogen.

According to yet another embodiment, specifically provided are compounds of formula (Ib), in which R⁵ is $C_{1-4}$alkyl (e.g. methyl, ethyl, n-propyl, isopropyl or n-butyl).

According to yet another embodiment, specifically provided are compounds of formula (Ib), in which R⁵ is hydrogen, —CH₃, —CH₂CH₃, —CH₂CH₂CH₃, —CH₂CH(CH₃)₂ or —CH₂CH₂CH₂CH₃.

According to yet another embodiment, specifically provided are compounds of formula (Ib), in which

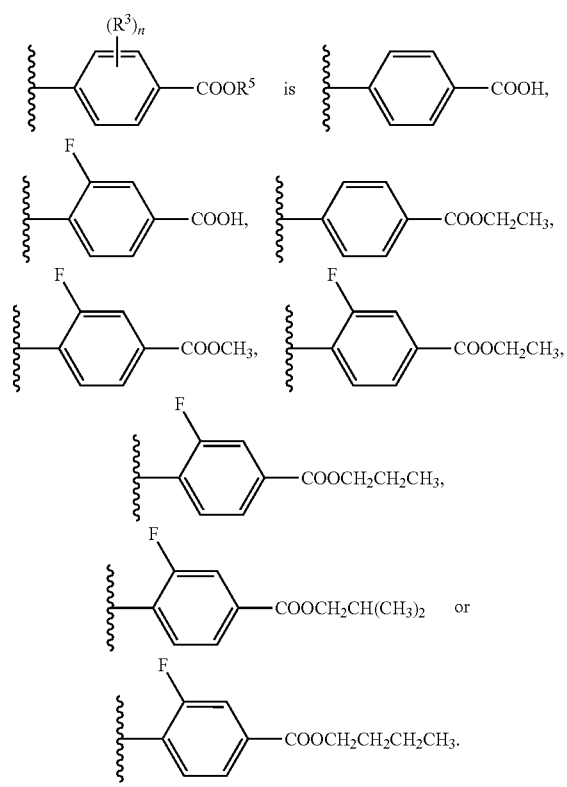

According to yet another embodiment, specifically provided are compounds of formula (Ib), in which

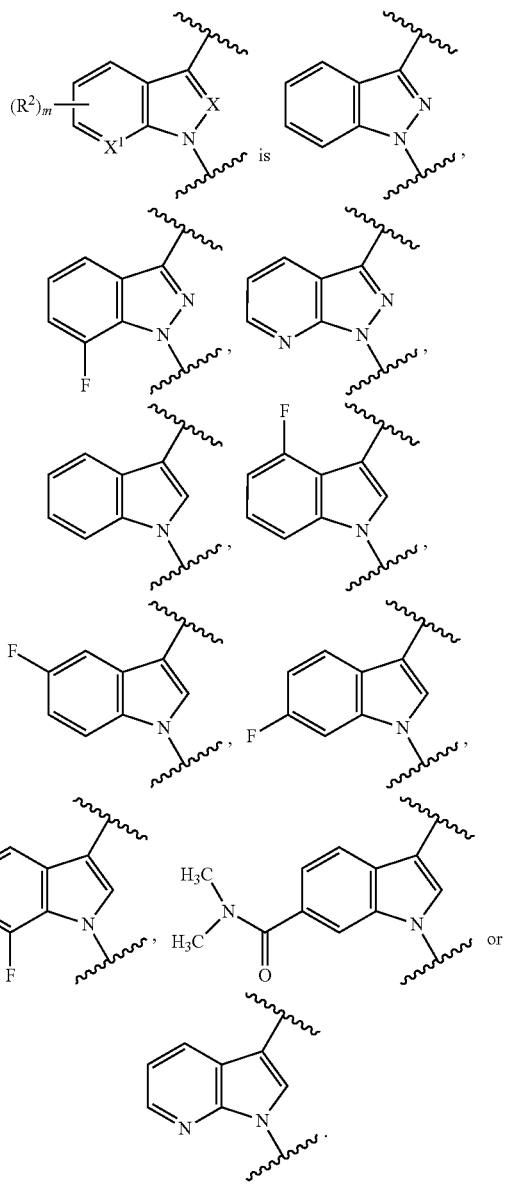

According to yet another embodiment, specifically provided are compounds of formula (Ib), in which
X is CH or N;
X¹ is N or CH;
each occurrence of R² is independently halogen (e.g. F, Cl or Br);
each occurrence of R³ is independently halogen (e.g. F, Cl or Br);
each occurrence of R⁴ is independently halogen (e.g. F, Cl or Br), $C_{1-8}$alkyl (e.g. methyl or ethyl), halo$C_{1-8}$alkyl (e.g. CHF₂ or CF₃) or $C_{3-6}$cycloalkyl (e.g. cyclopropyl);
R⁵ is hydrogen or $C_{1-4}$alkyl (e.g. methyl, ethyl, n-propyl, isopropyl or n-butyl);
'm' is 0 or 1;
'n' is 0 or 1; and
'p' is 0, 1 or 2.

According to yet another embodiment, specifically provided are compounds of formula (Ib), in which
X is N or CH;
X¹ is N or CH;

each occurrence of $R^2$ is F;
each occurrence of $R^3$ is F;
each occurrence of $R^4$ is independently F, Cl, $CH_3$, $CHF_2$, $CF_3$ or cyclopropyl;
$R^5$ is hydrogen, $-CH_3$, $-CH_2CH_3$, $-CH_2CH_2CH_3$, $-CH_2CH(CH_3)_2$ or $-CH_2CH_2CH_2CH_3$;
'm' is 0 or 1;
'n' is 0 or 1; and
'p' is 0, 1 or 2.

According to yet another embodiment, specifically provided are compounds of formula (Ib), in which
X is N or CH;
$X^1$ is N or CH;
each occurrence of $R^2$ is F;
each occurrence of $R^3$ is F;
$R^5$ is hydrogen, $-CH_3$, $-CH_2CH_3$, $-CH_2CH_2CH_3$, $-CH_2CH(CH_3)_2$ or $-CH_2CH_2CH_2CH_3$;
'm' is 0 or 1;
'n' is 0 or 1; and

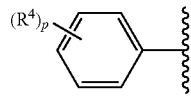

is phenyl, 2-fluorophenyl, 2-methylphenyl, 3-methylphenyl, 2-(trifluoromethyl)phenyl, 2,6-dichlorophenyl, 2,6-difluorophenyl, 2-chloro-6-(trifluoromethyl)phenyl, 4-chloro-2-(trifluoromethyl)phenyl, 2-chloro-6-(difluoromethyl)phenyl or 2-chloro-6-cyclopropylphenyl.

According to yet another embodiment, specifically provided are compounds of formula (Ib), in which is

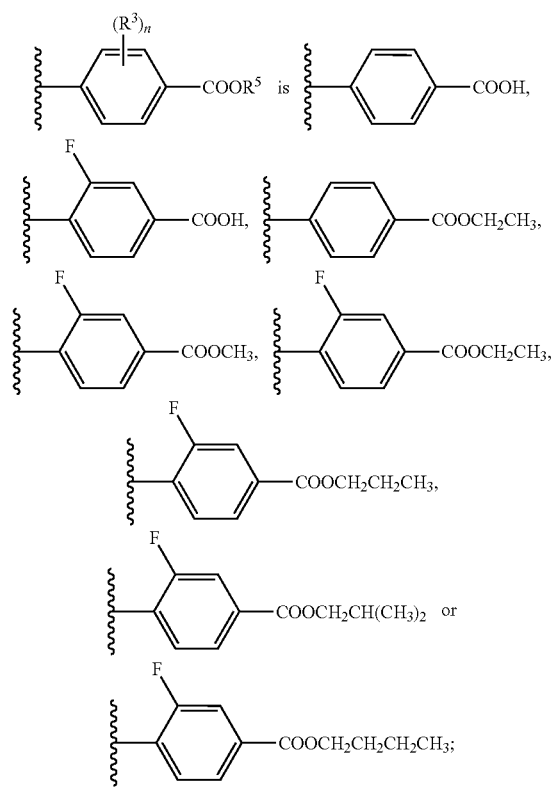

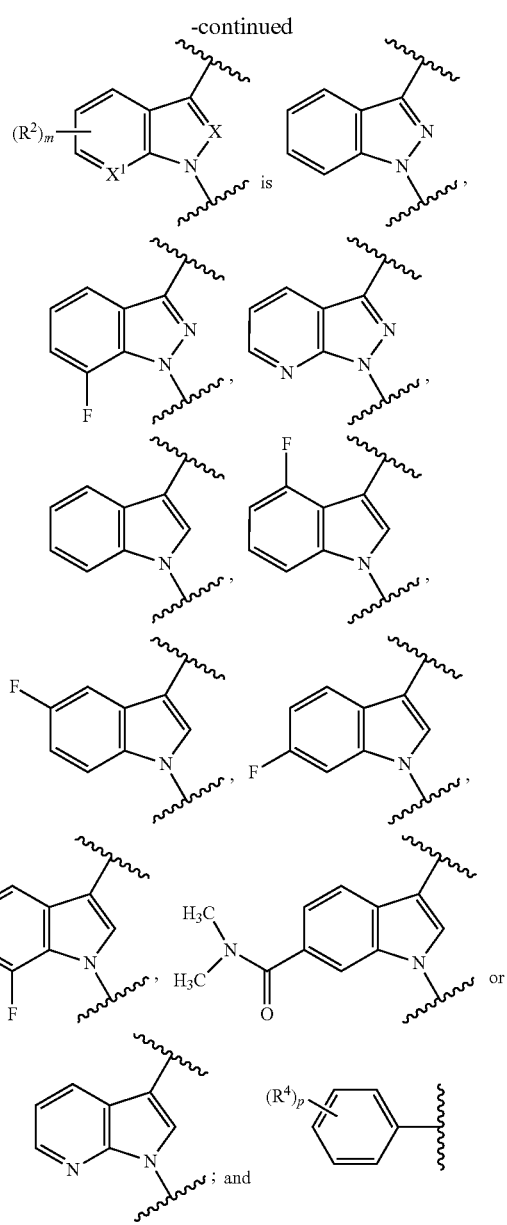

is phenyl, 2-fluorophenyl, 2-methylphenyl, 3-methylphenyl, 2-(trifluoromethyl)phenyl, 2,6-dichlorophenyl, 2,6-difluorophenyl, 2-chloro-6-(trifluoromethyl)phenyl, 4-chloro-2-(trifluoromethyl)phenyl, 2-chloro-6-(difluoromethyl)phenyl or 2-chloro-6-cyclopropylphenyl.

According to an embodiment, specifically provided are compounds of formula (Ib) that exhibit an $IC_{50}$ value with respect to RORγt activity of less than about 500 nM, preferably less than about 100 nM, more preferably less than about 50 nM.

Compounds of the present invention include the compounds in Examples 1-48. Thus, in one embodiment, the compound of formula (I) is selected from
4-[3-(2-Methylphenoxy)-1H-indazol-1-yl]benzoic acid;
4-{3-[2-(Trifluoromethyl)phenoxy]-1H-indazol-1-yl}benzoic acid;
4-[3-(3-Methylphenoxy)-1H-indazol-1-yl]benzoic acid;
4-(3-Phenoxy-1H-indazol-1-yl)benzoic acid;
4-[3-(2,6-Dichlorophenoxy)-1H-indazol-1-yl)benzoic acid;

4-[3-(2,6-Dichlorophenoxy)-1H-indazol-1-yl]-3-fluorobenzoic acid;
4-{3-[2-Chloro-6-(trifluoromethyl)phenoxy]-1H-indazol-1-yl}-3-fluorobenzoic acid;
3-Fluoro-4-{3-[2-(trifluoromethyl)phenoxy]-1H-indazol-1-yl}benzoic acid;
4-{3-[4-Chloro-2-(trifluoromethyl)phenoxy]-1H-indazol-1-yl}-3-fluorobenzoic acid;
4-{3-[2-Chloro-6-(difluoromethyl)phenoxy]-1H-indazol-1-yl}-3-fluorobenzoic acid;
4-[3-(2,6-Dichlorophenoxy)-7-fluoro-1H-indazol-1-yl]-3-fluorobenzoic acid;
4-{3-[2-Chloro-6-(difluoromethyl)phenoxy]-7-fluoro-1H-indazol-1-yl}-3-fluorobenzoic acid;
4-[3-(2-Chloro-6-cyclopropylphenoxy)-1H-indazol-1-yl]-3-fluorobenzoic acid;
4-[3-(2-Chloro-6-cyclopropylphenoxy)-7-fluoro-1H-indazol-1-yl]-3-fluorobenzoic acid;
4-{3-[(2-Fluorophenyl)carbonyl]-1H-indol-1-yl}benzoic acid;
4-{3-[(2,6-Dichlorophenyl)carbonyl]-1H-indol-1-yl}benzoic acid;
4-{3-[(2-Chlorophenyl)carbonyl]-1H-indol-1-yl}benzoic acid;
4-{3-[(2,6-Difluorophenyl)carbonyl]-1H-indol-1-yl}benzoic acid;
4-{3-[(2,6-Dichlorophenyl)carbonyl]-1H-indol-1-yl}-3-fluorobenzoic acid;
4-{3-[(2-Chlorophenyl)carbonyl]-1H-indol-1-yl}-3-fluorobenzoic acid;
4-{3-[2-Chloro-6-(trifluoromethyl)benzoyl]-1H-indol-1-yl}-3-fluorobenzoic acid;
4-[3-(2,6-Dichlorobenzoyl)-4-fluoro-1H-indol-1-yl]-3-fluorobenzoic acid;
4-[3-(2,6-Dichlorobenzoyl)-5-fluoro-1H-indol-1-yl]-3-fluorobenzoic acid;
4-[3-(2,6-Dichlorobenzoyl)-6-fluoro-1H-indol-1-yl]-3-fluorobenzoic acid;
4-[3-(2,6-Dichlorobenzoyl)-7-fluoro-1H-indol-1-yl]-3-fluorobenzoic acid;
4-[3-(2,6-Dichloro-benzoyl)-6-dimethylcarbamoyl-indol-1-yl]-3-fluoro-benzoic acid;
4-[3-(2,6-Dichlorobenzoyl)-1H-pyrrolo[2,3-b]pyridin-1-yl]-3-fluorobenzoic acid;
4-[3-(Phenylcarbonyl)-1H-indazol-1-yl]benzoic acid;
4-[3-(2,6-Dichlorobenzoyl)-1H-indazol-1-yl]benzoic acid;
4-(3-Benzoyl-1H-indazol-1-yl)-3-fluorobenzoic acid;
4-[3-(2,6-Dichlorobenzoyl)-1H-indazol-1-yl]-3-fluorobenzoic acid;
4-{3-[(2,6-Dichlorophenyl)carbonyl]-7-fluoro-1H-indazol-1-yl}benzoic acid;
4-(3-{[2-Chloro-6-(trifluoromethyl)phenyl]carbonyl}-1H-indazol-1-yl)-3-fluorobenzoic acid;
4-(3-{[2-Chloro-6-(trifluoromethyl)phenyl]carbonyl}-1H-indazol-1-yl)-benzoic acid;
4-{3-[(2-Chloro-6-cyclopropylphenyl)carbonyl]-7-fluoro-1H-indazol-1-yl}benzoic acid;
4-{3-[(2,6-Dichlorophenyl)carbonyl]-1H-pyrazolo[3,4-b]pyridin-1-yl}benzoic acid;
4-{3-[(2-Chloro-6-cyclopropylphenyl)carbonyl]-1H-pyrazolo[3,4-b]pyridin-1-yl}benzoic acid;
4-(3-{[2-Chloro-6-(trifluoromethyl)phenyl]carbonyl}-1H-pyrazolo[3,4-b]pyridin-1-yl)benzoic acid;
Ethyl 4-{3-[(2, 6-dichlorophenyl)carbonyl]-1H-indol-1-yl}-3-fluorobenzoate;
Propyl 4-{3-[(2,6-dichlorophenyl)carbonyl]-1H-indol-1-yl}-3-fluorobenzoate;
Butyl 4-{3-[(2,6-dichlorophenyl)carbonyl]-1H-indol-1-yl}-3-fluorobenzoate;
Ethyl 4-[3-(2,6-dichloro-benzoyl)-7-fluoro-1H-indol-1-yl]-3-fluorobenzoate;
Propyl 4-[3-(2,6-dichloro-benzoyl)-7-fluoro-1H-indol-1-yl]-3-fluorobenzoate;
Butyl 4-[3-(2,6-dichloro-benzoyl)-7-fluoro-1H-indol-1-yl]-3-fluorobenzoate;
Ethyl 4-{3-[2-chloro-6-(trifluoromethyl)phenoxy]-1H-indazol-1-yl}-3-fluorobenzoate;
Propyl 4-{3-[2-chloro-6-(trifluoromethyl)phenoxy]-1H-indazol-1-yl}-3-fluorobenzoate;
Butyl 4-{3-[2-chloro-6-(trifluoromethyl)phenoxy]-1H-indazol-1-yl}-3-fluorobenzoate;
Isopropyl 4-{3-[2-chloro-6-(trifluoromethyl)phenoxy]-1H-indazol-1-yl}-3-fluorobenzoate;
and pharmaceutically acceptable salt thereof.

It should be understood that formulas (I), (Ia) and (Ib) structurally encompass all geometrical isomers, stereoisomers, enantiomers and diastereomers, N-oxides, and pharmaceutically acceptable salts thereof.

As defined herein, esters of the compounds of present invention refer to a modified version or a precursor of a parent compound that has been esterified and is designed to enhance the delivery properties and be converted to the parent compound in the body.

Esters (e.g., compounds of formula (I), (Ia) or (Ib) in which variable $R^5$ is $C_{1-4}$alkyl) are entities structurally related to parent acidic drug compound (variable $R^5$ is H), which, after administration, release the parent drug in vivo as the result of a metabolic process, such as enzymatic or chemical hydrolysis of a susceptible functionality.

The present application also provides a pharmaceutical composition that includes at least one compound described herein and at least one pharmaceutically acceptable excipient (such as a pharmaceutically acceptable carrier or diluent). Preferably, the pharmaceutical composition comprises a therapeutically effective amount of at least one compound described herein. The compounds described herein may be associated with a pharmaceutically acceptable excipient (such as a carrier or a diluent) or be diluted by a carrier, or enclosed within a carrier which can be in the form of a tablet, capsule, sachet, paper or other container.

The compounds and pharmaceutical compositions of the present invention are useful for inhibiting the activity of RORγt. Thus, the present invention further provides a method of inhibiting RORγt in a subject in need thereof by administering to the subject one or more compounds described herein in the amount effective to cause inhibition of such receptor.

In a further aspect, the present invention relates to a method of treating a disease, disorder or condition modulated by RORγt, such as autoimmune disease, inflammatory disease, respiratory disorders, pain and cancer comprising administering to a subject in need thereof a compound according to any of the embodiments described herein.

In another further aspect, the present invention relates to a method of treating a disease, disorder or condition modulated by RORγt, such as chronic obstructive pulmonary disease (COPD), asthma, cough, pain, inflammatory pain, chronic pain, acute pain, arthritis, osteoarthritis, multiple sclerosis, rheumatoid arthritis, colitis, ulcerative colitis and inflammatory bowel disease, comprising administering to a subject in need thereof a compound according to any of the embodiments described herein.

DETAILED DESCRIPTION OF THE INVENTION

Definitions

The terms "halogen" or "halo" means fluorine (fluoro), chlorine (chloro), bromine (bromo), or iodine (iodo).

The term "alkyl" refers to a hydrocarbon chain radical that includes solely carbon and hydrogen atoms in the backbone, containing no unsaturation, having from one to eight carbon atoms (i.e. $C_{1-8}$alkyl), and which is attached to the rest of the molecule by a single bond, such as, but not limited to, methyl, ethyl, n-propyl, 1-methylethyl (isopropyl), n-butyl, n-pentyl, and 1,1-dimethylethyl (t-butyl). The term "$C_{1-6}$alkyl" refers to an alkyl chain having 1 to 6 carbon atoms. The term "$C_{1-4}$alkyl" refers to an alkyl chain having 1 to 4 carbon atoms. Unless set forth or recited to the contrary, all alkyl groups described or claimed herein may be straight chain or branched.

The term "haloalkyl" refers to at least one halo group (selected from F, Cl, Br or I), linked to an alkyl group as defined above (i.e. halo$C_{1-8}$alkyl). Examples of such haloalkyl moiety include, but are not limited to, trifluoromethyl, difluoromethyl and fluoromethyl groups. The term "halo$C_{1-4}$alkyl" refers to at least one halo group linked an alkyl chain having 1 to 4 carbon atoms. Unless set forth or recited to the contrary, all haloalkyl groups described herein may be straight chain or branched.

The term "hydroxy$C_{1-4}$alkyl" refers to an $C_{1-4}$alkyl group as defined above wherein one to three hydrogen atoms on different carbon atoms is/are replaced by hydroxyl groups (i.e. hydroxy$C_{1-4}$alkyl). Examples of hydroxy$C_{1-4}$alkyl moieties include, but are not limited to —$CH_2OH$ and —$C_2H_4OH$.

The term "cycloalkyl" denotes a non-aromatic mono or multicyclic ring system of 3 to about 12 carbon atoms, (i.e. $C_{3-12}$cycloalkyl). Examples of monocyclic cycloalkyl include but are not limited to cyclopropyl, cyclobutyl, cyclopentyl, and cyclohexyl. Examples of multicyclic cycloalkyl groups include, but are not limited to, perhydronapthyl, adamantyl and norbornyl groups, bridged cyclic groups or spirobicyclic groups, e.g., spiro(4,4)non-2-yl. The term "$C_{3-6}$cycloalkyl" refers to the cyclic ring having 3 to 6 carbon atoms. Examples of "$C_{3-6}$cycloalkyl" include but are not limited to cyclopropyl, cyclobutyl, cyclopentyl, or cyclohexyl.

The term "aryl" refers to an aromatic radical having 6 to 14 carbon atoms (i.e. $C_{6-14}$aryl), including monocyclic, bicyclic and tricyclic aromatic systems, such as phenyl, naphthyl, tetrahydronapthyl, indanyl, and biphenyl.

The term "heteroaryl" unless otherwise specified refers to 5 to 14 membered aromatic heterocyclic ring radical with one or more heteroatom(s) independently selected from N, O or S (i.e. 5 to 14 membered heteroaryl). The heteroaryl may be a mono-, bi- or tricyclic ring system. The heteroaryl ring radical may be attached to the main structure at any heteroatom or carbon atom that results in the creation of a stable structure. Examples of such heteroaryl ring radicals include, but are not limited to oxazolyl, isoxazolyl, imidazolyl, furyl, indolyl, isoindolyl, pyrrolyl, triazolyl, triazinyl, tetrazoyl, thienyl, oxadiazolyl, thiazolyl, isothiazolyl, pyridyl, pyrimidinyl, pyrazinyl, pyridazinyl, pyrazolyl, benzofuranyl, benzothiazolyl, benzoxazolyl, benzimidazolyl, benzothienyl, benzopyranyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl and phthalazinyl.

The term "pharmaceutically acceptable salt" includes salts prepared from pharmaceutically acceptable bases or acids including inorganic or organic bases and inorganic or organic acids. Examples of such salts include, but are not limited to, acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate, diphosphate, polygalacturonate, salicylate, stearate, sulfate, subacetate, succinate, tannate, tartrate, teoclate, tosylate, triethiodide and valerate. Examples of salts derived from inorganic bases include, but are not limited to, aluminum, ammonium, calcium, copper, ferric, ferrous, lithium, magnesium, manganic, mangamous, potassium, sodium, and zinc.

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

Pharmaceutical Compositions

The compounds of the invention are typically administered in the form of a pharmaceutical composition. Such compositions can be prepared using procedures well known in the pharmaceutical art and comprise at least one compound of the invention. The pharmaceutical compositions described herein comprise one or more compounds described herein and one or more pharmaceutically acceptable excipients. Typically, the pharmaceutically acceptable excipients are approved by regulatory authorities or are generally regarded as safe for human or animal use. The pharmaceutically acceptable excipients include, but are not limited to, carriers, diluents, glidants and lubricants, preservatives, buffering agents, chelating agents, polymers, gelling agents, viscosifying agents, solvents and the like.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters, and polyoxyethylene.

The pharmaceutical compositions described herein may also include one or more pharmaceutically acceptable auxiliary agents, wetting agents, suspending agents, preserving agents, buffers, sweetening agents, flavouring agents, colorants or any combination of the foregoing.

The pharmaceutical compositions may be in conventional forms, for example, capsules, tablets, solutions, suspensions, injectables or products for topical application. Further, the pharmaceutical composition of the present invention may be formulated so as to provide desired release profile.

Administration of the compounds of the invention, in pure form or in an appropriate pharmaceutical composition, can be carried out using any of the accepted routes of administration of such compounds or pharmaceutical compositions. The route of administration may be any route which effectively transports the active compound of the patent application to the appropriate or desired site of action. Suitable routes of administration include, but are not limited to, oral, nasal, buccal, dermal, intradermal, transdermal, parenteral, rectal, subcutaneous, intravenous, intraurethral, intramuscular, and topical.

Solid oral formulations include, but are not limited to, tablets, capsules (soft or hard gelatin), dragees (containing the active ingredient in powder or pellet form), troches and lozenges.

Liquid formulations include, but are not limited to, syrups, emulsions, and sterile injectable liquids, such as suspensions or solutions.

Topical dosage forms of the compounds include, but are not limited to, ointments, pastes, creams, lotions, powders, solutions, eye or ear drops, impregnated dressings, and may contain appropriate conventional additives such as preservatives, solvents to assist drug penetration.

The pharmaceutical compositions described herein may be prepared by conventional techniques, e.g., as described in *Remington: The Science and Practice of Pharmacy*, 20$^{th}$ Ed., 2003 (Lippincott Williams & Wilkins).

Suitable doses of the compounds for use in treating the diseases and disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. Mode of administration, dosage forms, and suitable pharmaceutical excipients can also be well used and adjusted by those skilled in the art. All changes and modifications are envisioned within the scope of the present patent application.

Methods of Treatment

The compounds of the present invention are particularly useful because they inhibit the activity of retinoid-related orphan receptor gamma, particularly retinoid-related orphan receptor gamma t (RORγt), i.e., they prevent, inhibit, or suppress the action of RORγt, and/or may elicit a RORγt modulating effect. Compounds of the invention are therefore useful in the treatment of those conditions in which inhibition of ROR gamma activity, and particularly RORγt, is required.

The compounds of the present patent application are modulators of RORγt and can be useful in the treatment of diseases/disorder mediated by RORγt. Accordingly, the compounds and the pharmaceutical compositions of this invention may be useful in the treatment of inflammatory, metabolic and autoimmune diseases mediated by RORγt.

The term "autoimmune diseases" will be understood by those skilled in the art to refer to a condition that occurs when the immune system mistakenly attacks and destroys healthy body tissue. An autoimmune disorder may result in the destruction of one or more types of body tissue, abnormal growth of an organ, and changes in organ function. An autoimmune disorder may affect one or more organ or tissue types which include, but are not limited to, blood vessels, connective tissues, endocrine glands such as the thyroid or pancreas, joints, muscles, red blood cells, and skin. Examples of autoimmune (or autoimmune-related) disorders include multiple sclerosis, arthritis, rheumatoid arthritis, psoriasis, Crohn's disease, gastrointestinal disorder, inflammatory bowel disease, irritable bowel syndrome, colitis, ulcerative colitis, Sjorgen's syndrome, atopic dermatitis, optic neuritis, respiratory disorder, chronic obstructive pulmonary disease (COPD), asthma, type I diabetes, neuromyelitis optica, Myasthenia Gavis, uveitis, Guillain-Barre syndrome, psoriatic arthritis, Gaves' disease, allergy, osteoarthritis, Kawasaki disease, mucosal leishmaniasis, Hashimoto's thyroiditis, Pernicious anemia, Addison's disease, Systemic lupus erythematosus, Dermatomyositis, Sjogren syndrome, Lupus erythematosus, Myasthenia gravis, Reactive arthritis, Celiac disease—sprue (gluten-sensitive enteropathy), Graves's disease, thymopoiesis and Lupus.

Compounds of the present patent application may also be useful in the treatment of inflammation. The term "inflammation" will be understood by those skilled in the art to include any condition characterized by a localized or a systemic protective response, which may be elicited by physical trauma, infection, chronic diseases, and/or chemical and/or physiological reactions to external stimuli (e.g. as part of an allergic response). Any such response, which may serve to destroy, dilute or sequester both the injurious agent and the injured tissue, may be manifest by, for example, heat, swelling, pain, redness, dilation of blood vessels and/or increased blood flow, invasion of the affected area by white.

The term "inflammation" is also understood to include any inflammatory disease, disorder or condition per se, any condition that has an inflammatory component associated with it, and/or any condition characterized by inflammation as a symptom, including inter alia acute, chronic, ulcerative, specific, allergic, infection by pathogens, immune reactions due to hypersensitivity, entering foreign bodies, physical injury, and necrotic inflammation, and other forms of inflammation known to those skilled in the art. The term thus also includes, for the purposes of this present patent application, inflammatory pain, pain generally and/or fever.

The compounds of the present invention may be used for treatment of arthritis, including, but are not limited to, rheumatoid arthritis, osteoarthritis, psoriatic arthritis, septic arthritis, spondyloarthropathies, gouty arthritis, systemic lupus erythematosus and juvenile arthritis, osteoarthritis, collagen-induced arthritis (CIA) and other arthritic conditions.

The compounds of the present invention may be used for treatment of respiratory disorders including, but are not limited to, chronic obstructive pulmonary disease (COPD), asthma, bronchospasm, and cough.

Other respiratory disorders include, but are not limited to, bronchitis, bronchiolitis, bronchiectasis, acute nasoparyngitis, acute and chronic sinusitis, maxillary sinusitis, pharyngitis, tonsillitis, laryngitis, tracheitis, epiglottitis, croup, chronic disease of tonsils and adenoids, hypertrophy of tonsils and adenoids, peritonsillar abscess, rhinitis, abscess or ulcer and nose, pneumonia, viral and bacterial pneumonia, bronchopneumonia, influenza, extrinsic allergic alveolitis, coal workers' pneumoconiosis, asbestosis, pneumoconiosis, pneumonopathy, respiratory conditions due to chemical fumes, vapors and other external agents, emphysema, pleurisy, pneumothorax, abscess of lung and mediastinum, pulmonary congestion and hypostasis, postinflammatory pulmonary fibrosis, other alveolar and parietoalveolar pneumonopathy, idiopathic fibrosing alveolitis, Hamman-Rich syndrome, atelectasis, ARDS, acute respiratory failure, mediastinitis.

The compounds of the present invention may also be used for treatment of pain conditions. The pain can be acute or chronic pain. Thus, the compounds of the present invention may be used for treatment of e.g., inflammatory pain, arthritic pain, neuropathic pain, post-operative pain, surgical pain, visceral pain, dental pain, premenstrual pain, central pain, cancer pain, pain due to burns; migraine or cluster headaches, nerve injury, neuritis, neuralgias, poisoning, ischemic injury, interstitial cystitis, viral, parasitic or bacterial infection, post-traumatic injury, or pain associated with irritable bowel syndrome.

The compounds of the present invention may further be used for treatment of gastrointestinal disorder such as, but not limited to, irritable bowel syndrome, inflammatory bowel disease, colitis, ulcerative colitis, biliary colic and other biliary disorders, renal colic, diarrhea-dominant IBS, and pain associated with gastrointestinal distension.

In addition, the compounds of the present invention may be useful in the treatment of cancer, and pain associated with cancer. Such cancers include, e.g., multiple myeloma and bone disease associated with multiple myeloma, melanoma, medulloblastoma, acute myelogenous leukemia (AML), head and neck squamous cell carcinoma, hepatocellular carcinoma, gastric cancer, bladder carcinoma and colon cancer.

The compounds of the present invention may be useful in a treatment of disease, disorder, syndrome or condition selected from the group consisting of chronic obstructive pulmonary disease (COPD), asthma, cough, pain, inflammatory pain, chronic pain, acute pain, arthritis, osteoarthritis, multiple sclerosis, rheumatoid arthritis, colitis, ulcerative colitis and inflammatory bowel disease.

Any of the methods of treatment described herein comprise administering an effective amount of a compound according to Formula I, (Ia) or (Ib), or a pharmaceutically-acceptable salt thereof, to a subject (particularly a human) in need thereof.

The present inventions further relates to the use of the compounds described herein in the preparation of a medicament for the treatment of diseases mediated by RORγt.

The compounds of the invention are effective both in the therapeutic and/or prophylactic treatment of the above-mentioned conditions. For the above-mentioned therapeutic uses the dosage administered may vary with the compound employed, the mode of administration, the treatment desired and the disorder.

The daily dosage of the compound of the invention administered may be in the range from about 0.05 mg/kg to about 100 mg/kg.

General Methods of Preparation

The compounds, described herein, including compounds of general formula (I), (Ia) and (Ib) and specific examples are prepared through the synthetic methods as depicted in Schemes 1 to 10. Furthermore, in the following schemes, where specific acids, bases, reagents, coupling reagents, solvents, etc. are mentioned, it is understood that other suitable acids, bases, reagents, coupling reagents, solvents etc. may be used and are included within the scope of the present invention. The modifications to reaction conditions, for example, temperature, duration of the reaction or combinations thereof, are envisioned as part of the present invention. The compounds obtained using the general reaction sequences may be of insufficient purity. These compounds can be purified using any of the methods for purification of organic compounds known to persons skilled in the art, for example, crystallization or silica gel or alumina column chromatography using different solvents in suitable ratios. All possible geometrical isomers and stereoisomers are envisioned within the scope of this invention.

The starting materials used herein are commercially available or were prepared by methods known in the art to those of ordinary skill or by methods disclosed herein. In general, the intermediates and compounds of the present invention can be prepared through the reaction schemes as follows.

A general approach for the synthesis of compound of general formula (Ia-A) (wherein $R^2$, $R^3$, $R^4$, 'm', 'n' and 'p' are as defined with respect to a compound of formula (Ia)) is shown in Scheme 1. Thus, ethyl 4-aminobenzoate of formula (1) on reaction with sodium nitrite and tin chloride may give phenylhydrazine compound of formula (2). The compound of formula (2) on coupling reaction with isatoic anhydride of formula (3a) in the presence of a base such as N,N-diisopropylethylamine (DIPEA) forms the corresponding phenylcarbamate in-situ followed by decarboxylation to yield phenylhydrazide of the formula (4). Alternatively, Intermediate compound of formula (4) can also be prepared by reaction of phenylhydrazine derivative (2) with substituted anthranilic acid (3b) in the presence of 1-ethyl-3-(3-dimethylaminopropyl)carbodiimide (EDCI), 1-hydroxybenzotriazole (HOBT) and base such as N-methylmorpholine. The compound of formula (4) on treatment with sodium nitrite and conc. hydrochloric acid may yield the indazole compound of formula (5).

The reaction of compound of formula (5) with phenyl boronic acid compound of formula (6) may yield compound of formula (7). In an embodiment, the compound of formula (5) may be reacted with compound of formula (6) in the presence of catalyst such as copper acetate. In another embodiment, the compound of formula (5) may be reacted with compound of formula (6) in the presence of a suitable base. The suitable base may be triethylamine or pyridine. The reaction may be carried out in a suitable solvent or mixture of solvents. The suitable solvent may be DCM.

In another embodiment, the compound of formula (5) may be reacted with compound of formula (6) in the presence of copper acetate and triethylamine in DCM.

Ester hydrolysis of the compound of formula (7) may yield compound of formula (Ia-A). In an embodiment, ester hydrolysis of the compound of formula (7) may be carried out in the presence of a suitable base. The suitable base may be NaOH, KOH or LiOH. The reaction may be carried out in a suitable solvent or mixture thereof. The suitable solvent may be THF, methanol, water or mixture thereof.

In an embodiment, ester hydrolysis of the compound of formula (7) to yield compound of formula (Ia-A) may be carried out using LiOH in a solvent selected from THF, methanol and water or combination thereof.

In another embodiment, the compound of formula (Ia-A)) may be optionally further converted to pharmaceutically acceptable salt.

Scheme 1

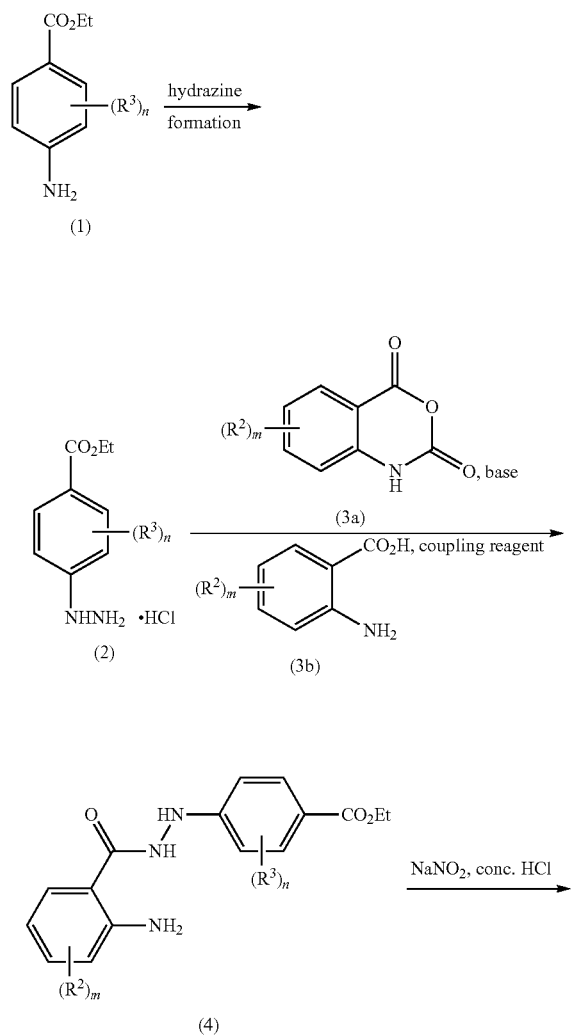

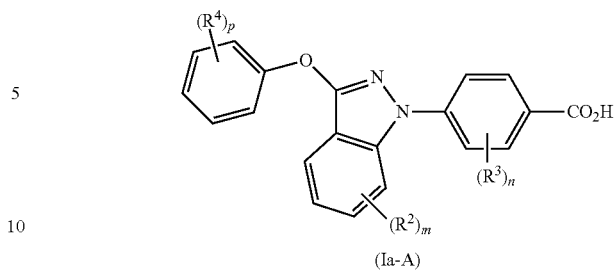

Alternatively, the compounds of formula (Ia-A) can also be prepared from 3-hydroxyindazole compound of formula (5) as described in scheme 2. Thus, Intermediate (5) on reaction with an appropriate halo nitro compound of formula (8) (wherein Z can be F, Cl or Br) may give Intermediate (9). The nitro group of Intermediate (9) may be reduced to give the corresponding amine intermediate which on treatment with tert-butyl nitrite may give the deaminated product (10) via formation of its diazonium salt or can be displaced with chlorine by quenching the diazonium salt with copper (II) chloride.

Ester hydrolysis of the compound of formula (10) may yield compound of formula (Ia-A). In an embodiment, ester hydrolysis of the compound of formula (10) may be carried out in the presence of a suitable base. The suitable base may be NaOH, KOH or LiOH. The reaction may be carried out in a suitable solvent or mixture thereof. The suitable solvent may be THF, methanol, water or combination thereof.

In an embodiment, ester hydrolysis of the compound of formula (10) to yield compound of formula (Ia-A) may be carried out using LiOH in a solvent selected from THF, methanol and water or combination thereof.

In another embodiment, the compound of formula (Ia-A)) may be optionally further converted to pharmaceutically acceptable salt.

Scheme 2

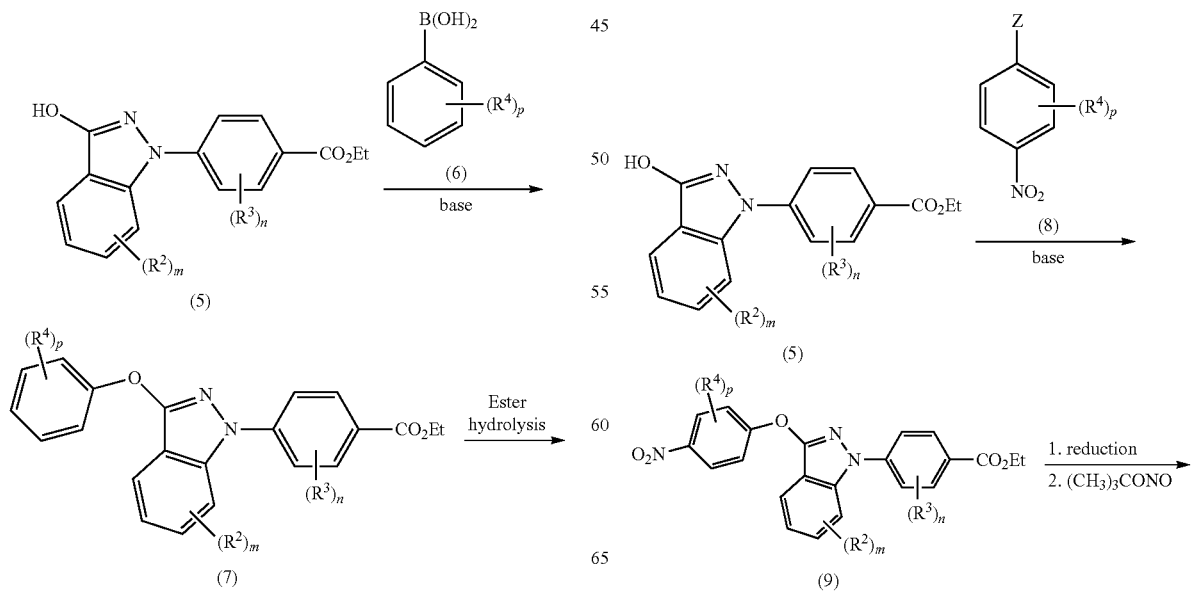

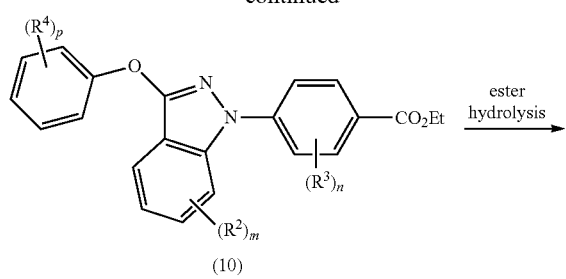

(10)

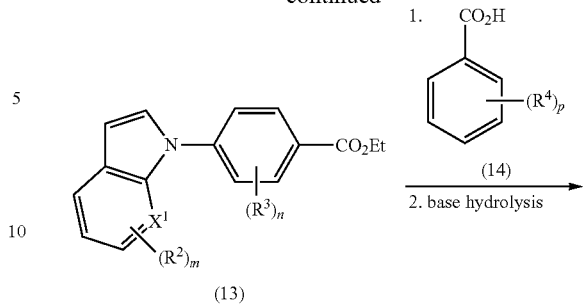

(13)

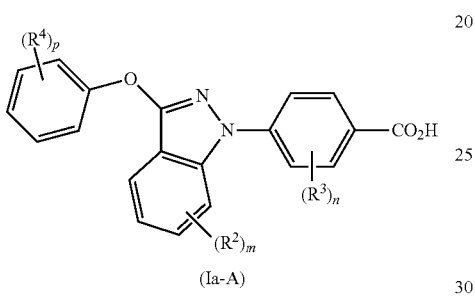

(Ia-A)

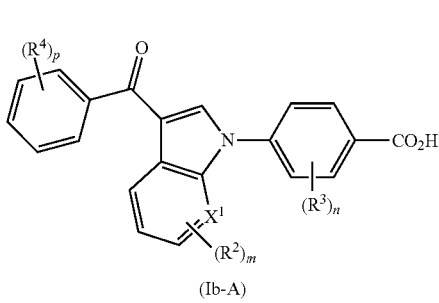

(Ib-A)

An approach for the synthesis of compound of formula (Ib-A) (wherein $X^1$, $R^2$, $R^3$, $R^4$, 'm', 'n' and 'p' are as defined with respect to a compound of formula (Ib)) is shown in Scheme 3. The indole compound of formula (11) on reaction with ethyl 4-iodobenzoate derivative (12) in the presence of a base such as potassium bicarbonate using L-proline and copper iodide may give ester intermediate compound of formula (13). Benzoyl chloride intermediate {formed in situ by reaction of benzoic acid derivative (14) with oxalyl chloride} and aluminum chloride may be reacted with Intermediate (13) to afford the corresponding keto ester intermediate followed by reaction with lithium hydroxide mediated hydrolysis of the ethyl ester Intermediate may give the final compound of general formula (Ib-A).

In an embodiment, the compound of formula (Ib-A)) may be optionally further converted to pharmaceutically acceptable salt.

The compound of formula (Ib-B) (wherein $R^2$, $R^3$, $R^4$, 'm', 'n' and 'p' are as defined with respect to a compound of formula (Ib)) can also be prepared as shown in scheme 4. The reaction of indole compound of formula (11a) with benzoyl chloride compound of formula (15) in the presence of aluminum chloride, ethyl magnesium bromide and zinc chloride may give the keto indole compound of formula (16). N-arylation of compound of formula (16) with ethyl 4-iodobenzoate compound of formula (12) using base such as potassium bicarbonate and L-proline in the presence of copper iodide may give ester intermediate which on lithium hydroxide mediated hydrolysis may afford the final compound of formula (Ib-B).

In an embodiment, the compound of formula (Ib-B)) may be optionally further converted to pharmaceutically acceptable salt.

Scheme 3

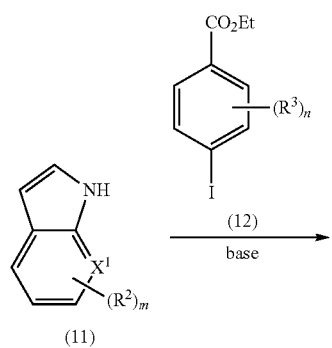

Scheme 4

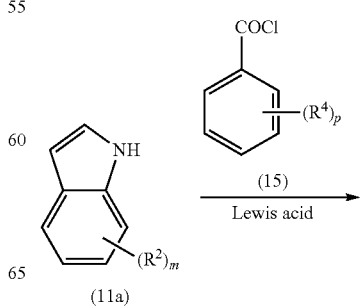

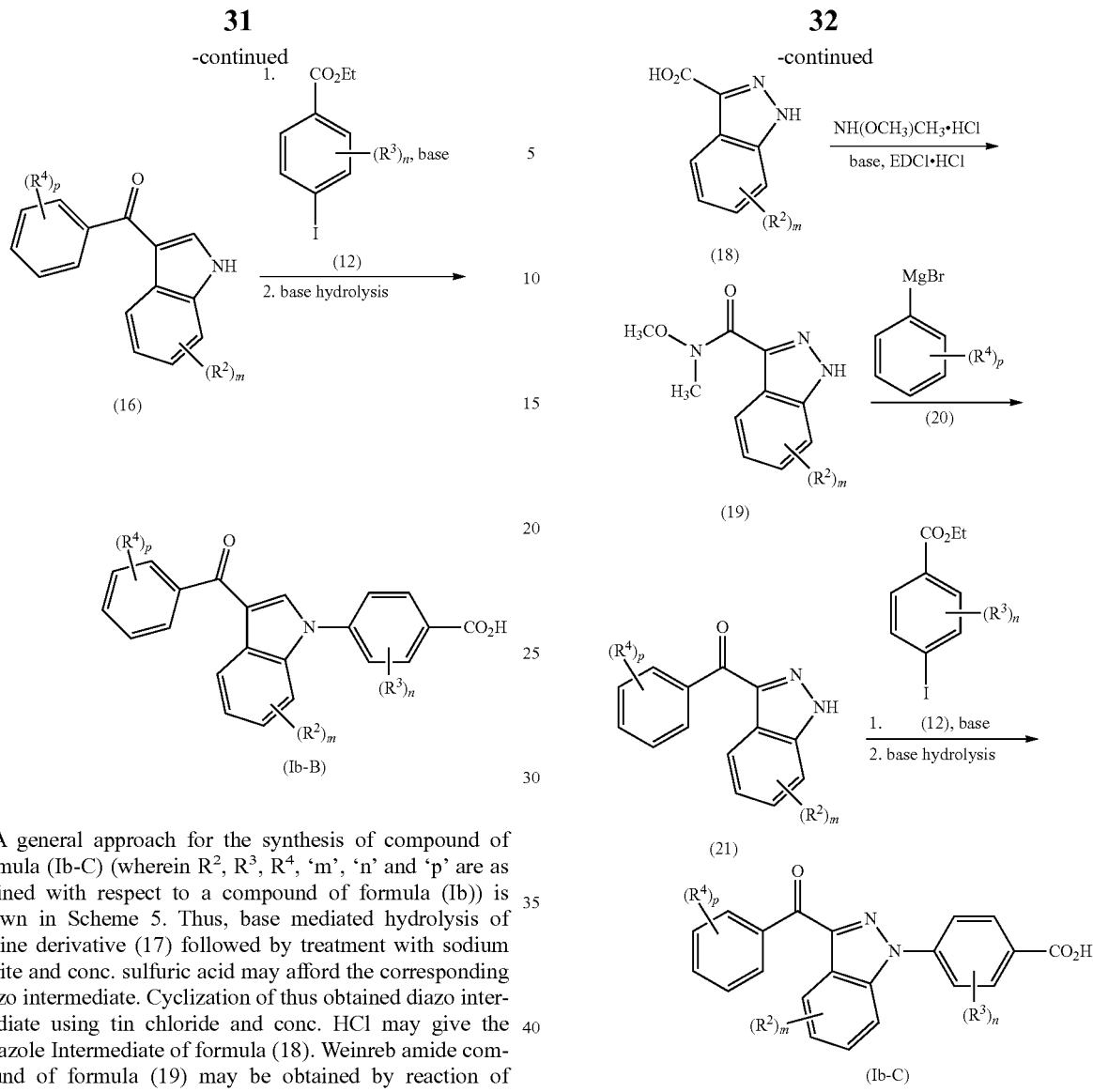

A general approach for the synthesis of compound of formula (Ib-C) (wherein $R^2$, $R^3$, $R^4$, 'm', 'n' and 'p' are as defined with respect to a compound of formula (Ib)) is shown in Scheme 5. Thus, base mediated hydrolysis of isatine derivative (17) followed by treatment with sodium nitrite and conc. sulfuric acid may afford the corresponding diazo intermediate. Cyclization of thus obtained diazo intermediate using tin chloride and conc. HCl may give the indazole Intermediate of formula (18). Weinreb amide compound of formula (19) may be obtained by reaction of Intermediate (18) with N,O-dimethylhydroxylamine hydrochloride using EDCI.HCl and base such as pyridine. Grignard reaction of Intermediate (19) with aryl magnesium bromide of formula (20) may give the keto intermediate of formula (21). N-arylation of Intermediate (21) with ethyl 4-iodobenzoate compound of formula (12) followed by lithium hydroxide mediated hydrolysis may afford the final compound of the formula (Ib-C).

In an embodiment, the compound of formula (Ib-C)) may be optionally further converted to pharmaceutically acceptable salt.

Scheme 5

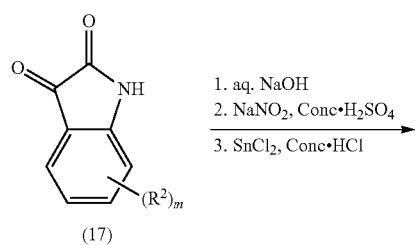

The indazole derivatives of formula (Ib-D) (wherein $X^1$, $R^2$, $R^3$, $R^4$, 'm', 'n' and 'p' are as defined with respect to a compound of formula (Ib)) can also be prepared as shown in Scheme 6. The 3-halo indazole compound of formula (22) (wherein Z can be halogen e.g. F, Cl or Br) on benzylation reaction using 1-halomethyl-4-methoxybenzene of formula (23) (wherein Z can be halogen e.g. F, Cl or Br) and base such as sodium hydride may give N-protected Intermediate compound of formula (24). The nucleophile generated by reaction of Intermediate (24) with isopropyl magnesium chloride further may be reacted with benzaldehyde compound of formula (25) to give the hydroxy indazole compound of formula (26). Oxidation of hydroxy indazole of formula (26) to keto using appropriate oxidizing agent such as Dess-Martin periodinane, manganese oxide, etc. may give the corresponding benzoyl intermediate which on deprotection using triflic acid and trifluoroacetic acid may yield indazole compound of formula (27). N-arylation of Intermediate (27) with ethyl 4-iodobenzoate derivative followed by lithium hydroxide mediated hydrolysis may yield the final compound of general formula (Ib-D).

In an embodiment, the compound of formula (Ib-D)) may be optionally further converted to pharmaceutically acceptable salt.

Scheme 6

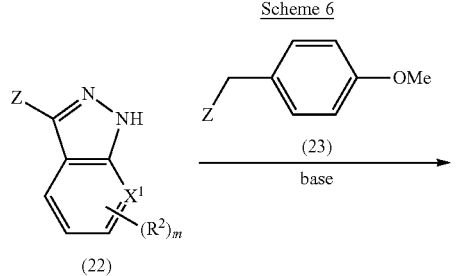

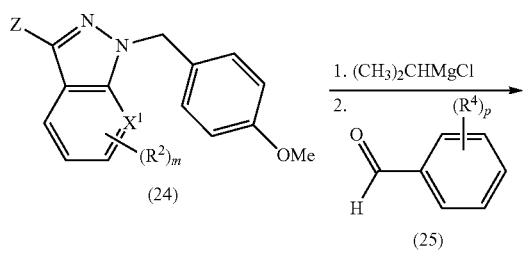

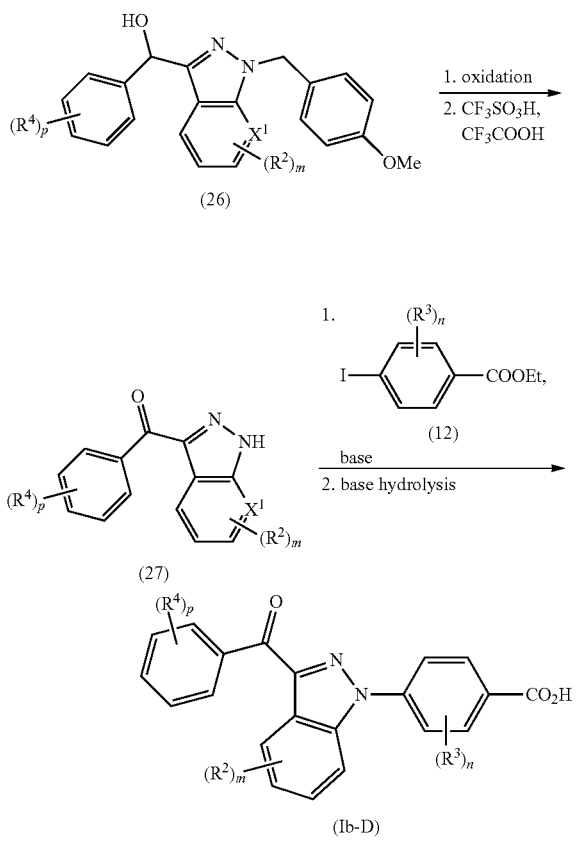

Scheme 7

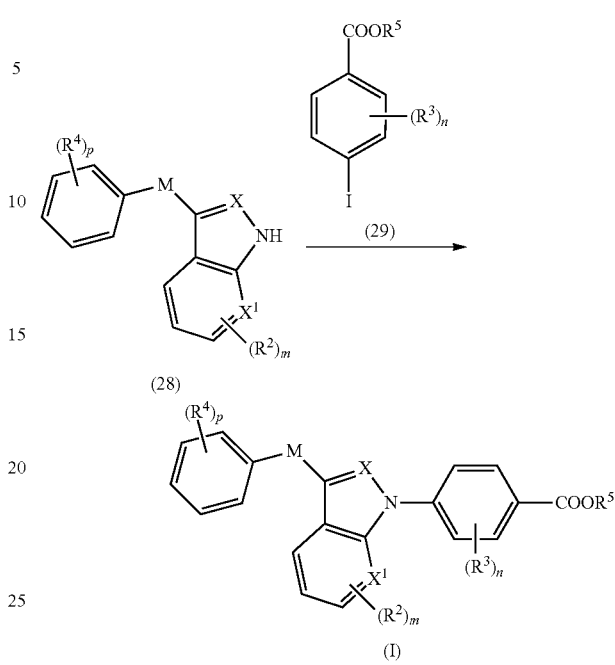

A general approach for the synthesis of compound of general formula (I) (wherein M, X, $X^1$, $R^2$, $R^3$, $R^4$, 'm', 'n' and 'p' as defined with respect to a compound of formula (I)) is shown in scheme 7.

The process for the preparation of compound of formula (I) or a pharmaceutically acceptable salt thereof, the process comprising:

(i) reacting a compound of formula (28) with a compound of formula (29) (wherein $R^5$ is $C_{1-4}$alkyl) to afford a compound of formula (I);

(ii) optionally hydrolysing the compound formula (I) to afford a compound of formula (I) in which $R^5$ is H; and (iii) optionally converting the compound of formula (I) to a pharmaceutically acceptable salt thereof.

In an embodiment, the compound of formula (28) is reacted with compound of formula (29) in the presence of copper iodide and L-proline.

In another embodiment, the compound of formula (28) is reacted with compound of formula (29) in the presence of a suitable base. The suitable base may be potassium bicarbonate.

In yet another embodiment, the compound of formula (28) is reacted with compound of formula (29) in a suitable solvent or mixture thereof. The suitable solvent may be DMSO.

In yet another embodiment, the compound of formula (28) is reacted with compound of formula (29) in the presence copper iodide, potassium bicarbonate and L-proline in DMSO.

In yet another embodiment, hydrolysis of the compound of formula (I) is carried out in the presence of a suitable base. The suitable base may be NaOH, KOH or LiOH.

In yet another embodiment, hydrolysis of the compound of formula (I) is carried out in suitable solvent or mixture of solvents. The suitable solvent may be THF, methanol, water or mixture thereof.

In yet another embodiment, hydrolysis of the compound of formula (I) is carried out in the presence of NaOH, KOH or LiOH in mixture of solvent selected from THF, methanol and water.

In yet another embodiment, hydrolysis of the compound of formula (I) is carried out using LiOH in solvent selected from THF, methanol, water and any combination thereof.

In yet another embodiment, the compound of formula (I) may be optionally further converted to pharmaceutically acceptable salt.

An approach for the synthesis of compound of general formula (I") (wherein M, X, $X^1$, $R^2$, $R^3$, $R^4$, 'm', 'n' and 'p' as defined with respect to a compound of formula (I) and $R^{5*}$ is $C_{1-4}$alkyl) is shown in scheme 8.

Scheme 8

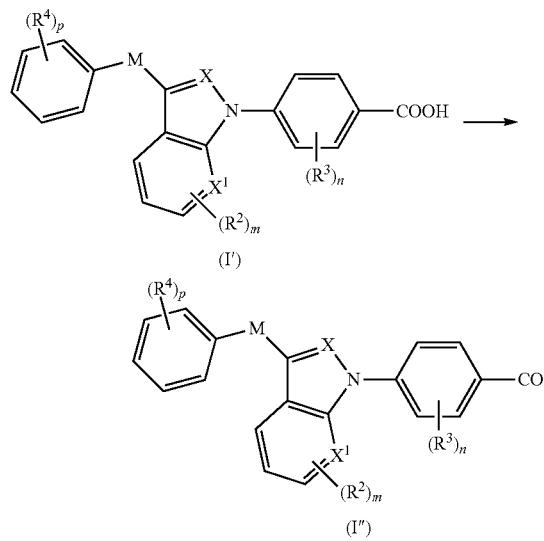

The process for the preparation of compound of formula (I") or a pharmaceutically acceptable salt thereof which comprises:

converting a compound of formula (I') to a compound of formula (I") (wherein $R^{5*}$ is $C_{1-4}$alkyl); and optionally converting the compound of formula (I") to a pharmaceutically acceptable salt thereof.

In an embodiment, the compound of formula (I') may be reacted with halo$C_{1-4}$alkyl in the presence of a suitable base to obtain the compound of formula (I"). The suitable base may be potassium carbonate.

In another embodiment, the compound of formula (I') may be reacted with halo$C_{1-4}$alkyl in suitable solvent or mixture of solvents to obtain the compound of formula (I"). The suitable solvent may be DMF.

In yet another embodiment, the compound of formula (I') may be reacted with halo$C_{1-4}$alkyl (e.g. bromopropane, iodobutane or bromobutane) in the presence of potassium carbonate in DMF to obtain a compound of formula (I").

In yet another embodiment, the compound of formula (I') may be reacted with hydroxy$C_{1-4}$alkyl in the presence of a suitable acid to obtain a compound of formula (I"). The suitable acid may be sulfuric acid.

In yet another embodiment, the compound of formula (I') may be treated with hydroxy$C_{1-4}$alkyl in the presence of sulfuric acid at reflux temperature to obtain a compound of formula (I").

A general approach for the synthesis of compound of general formula (Ia) (wherein $R^2$, $R^3$, $R^4$, 'm', 'n' and 'p' as defined with respect to a compound of formula (Ia)) is shown in scheme 9.

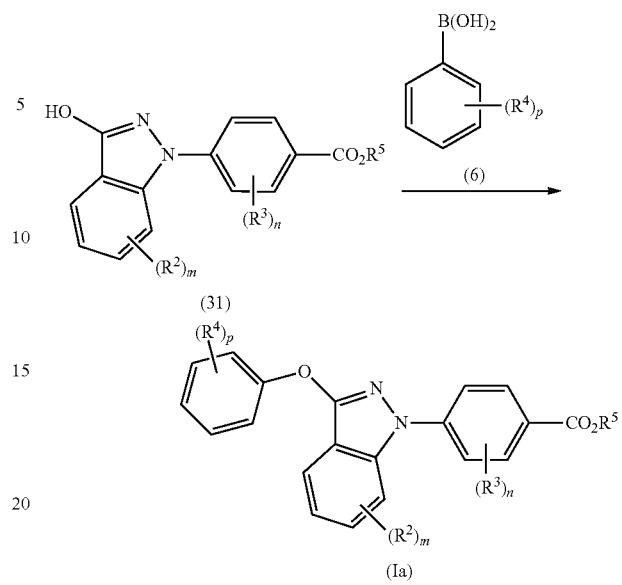

The process for the preparation of compound of formula (Ia) or a pharmaceutically acceptable salt thereof, the process comprising:

(i) reacting a compound of formula (31) (wherein $R^5$ is $C_{1-4}$alkyl) with a compound of formula (6) to afford a compound of formula (Ia);

(ii) optionally hydrolysing the compound of formula (Ia) to afford a compound of formula (Ia) in which $R^5$ is H; and (iii) optionally converting the compound of formula (Ia) to a pharmaceutically acceptable salt thereof.

In an embodiment, the compound of formula (31) is reacted with compound of formula (6) in the presence of copper acetate.

In another embodiment, the compound of formula (31) is reacted with compound of formula (6) in the presence of a suitable base. The suitable base may be triethylamine or pyridine.

In yet another embodiment, the compound of formula (31) is reacted with compound of formula (6) in a suitable solvent or mixture of solvents. The suitable solvent may be DCM.

In yet another embodiment, the compound of formula (31) is reacted with compound of formula (6) in the presence copper acetate and triethylamine in DCM.

In yet another embodiment, hydrolysis of the compound of formula (Ia) is carried out in the presence of a suitable base. The suitable base may be NaOH, KOH or LiOH.

In yet another embodiment, hydrolysis of the compound of formula (Ia) is carried out in suitable solvent or mixture of solvents. The suitable solvent may be THF, methanol, water or combination thereof.

In yet another embodiment, hydrolysis of the compound of formula (Ia) is carried out in the presence of NaOH, KOH or LiOH in mixture of solvent selected from THF, methanol and water.

In yet another embodiment, hydrolysis of the compound of formula (Ia) is carried out using LiOH in solvent selected from THF, methanol, water and any combination thereof.

In yet another embodiment, the compound of formula (Ia) may be optionally further converted to pharmaceutically acceptable salt.

A general approach for the synthesis of compound of general formula (Ib) (wherein X, $X^1$, $R^2$, $R^3$, $R^4$, 'm', 'n' and 'p' as defined with respect to a compound of formula (Ib)) is shown in scheme 10.

Scheme 10

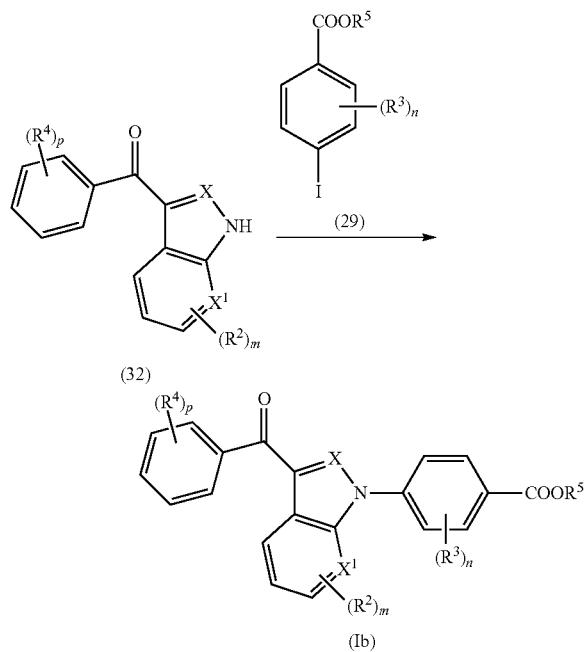

The process for the preparation of compound of formula (Ib) or a pharmaceutically acceptable salt thereof, the process comprising:

(i) reacting a compound of formula (32) with a compound of formula (29) (wherein $R^5$ is $C_{1-4}$alkyl) to afford a compound of formula (Ib);

(ii) optionally hydrolysing the compound formula (Ib) to afford a compound of formula (Ib) in which $R^5$ is H; and (iii) optionally converting the compound of formula (Ib) to a pharmaceutically acceptable salt thereof.

In an embodiment, the compound of formula (32) is reacted with compound of formula (29) in the presence of catalyst such as copper iodide and L-proline.

In another embodiment, the compound of formula (32) is reacted with compound of formula (29) in the presence of a suitable base. The suitable base may be potassium bicarbonate.

In yet another embodiment, the compound of formula (32) is reacted with compound of formula (29) in a suitable solvent or mixture thereof. The suitable solvent may be DMSO.

In yet another embodiment, the compound of formula (32) is reacted with compound of formula (29) in the presence copper iodide, potassium bicarbonate and L-proline in DMSO.

In yet another embodiment, hydrolysis of the compound of formula (Ib) is carried out in the presence of a suitable base. The suitable base may be NaOH, KOH or LiOH.

In yet another embodiment, hydrolysis of the compound of formula (Ib) is carried out in suitable solvent or mixture of solvents. The suitable solvent may be THF, methanol, water or mixture thereof.

In yet another embodiment, hydrolysis of the compound of formula (Ib) is carried out in the presence of NaOH, KOH or LiOH in mixture of solvent selected from THF, methanol and water.

In yet another embodiment, hydrolysis of the compound of formula (Ib) is carried out using LiOH in solvent selected from THF, methanol, water and any combination thereof.

In yet another embodiment, the compound of formula (Ib) may be optionally further converted to pharmaceutically acceptable salt.

EXPERIMENTAL

Unless otherwise stated, work-up includes distribution of the reaction mixture between the organic and aqueous phase indicated within parentheses, separation of layers and drying the organic layer over sodium sulphate, filtration and evaporation of the solvent. Purification, unless otherwise mentioned, includes purification by silica gel chromatographic techniques, generally using ethyl acetate/petroleum ether mixture of a suitable polarity as the mobile phase. Use of a different eluent system is indicated within parentheses.

The abbreviations, symbols and terms used in the examples and assays have the following meanings throughout: DCM: dichloromethane; DMSO-$d_6$: Hexadeuterodimethyl sulfoxide; DMSO dimethyl sulfoxide; $^1$H NMR: Proton Nuclear Magnetic Resonance; DMF: N,N-dimethyl formamide; EDCI.HCl: 1-ethyl-3-(3-dimethylaminopropyl) carbodiimide hydrochloride; HOBT: 1-hydroxybenzotriazole; NaOH: Sodium Hydroxide; KOH: Potassium Hydroxide; LiOH: Lithium Hydroxide; DIPEA: N,N-diisopropylethylamine; THF: Tetrahydofuran; HCl: hydrochloric acid; $Na_2SO_4$: Sodium sulfate; J: Coupling constant in units of Hz; h: hour(s); RT or rt: Room temperature (22-26° C.); APCI-MS: Atmospheric Pressure Chemical Ionization Mass Spectrometry; MHz: Megahertz

INTERMEDIATES

Intermediate 1

Ethyl 4-(3-hydroxy-1H-indazol-1-yl)benzoate

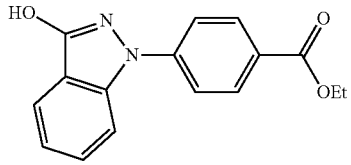 [SMILES: CCOC(=O)c1ccc(-n2nc(O)c3ccccc32)cc1]

Step 1: Ethyl 4-hydrazinylbenzoate.hydrochloride

To a stirred and cooled (−20° C.) solution of ethyl 4-aminobenzoate (2 g, 12.181 mmol) in conc. HCl (22 mL) was added aqueous solution of sodium nitrite (925 mg, 13.40 mmol). This mixture was added very slowly to a precooled (−10° C.) mixture of tin chloride (13.8 g, 60.905 mmol) in conc. HCl (15 mL) and stirred at the same temperature for 30 min. The precipitate obtained was filtered and washed with diethyl ether (2×20 mL) to yield 2.2 g of the title product as off white solid; $^1$H NMR (300 MHz, DMSO-$d_6$) δ 1.29 (t, J=7.2 Hz, 3H), 4.26 (q, J=7.5 Hz, 2H), 6.99 (d, J=7.8 Hz, 2H), 7.87 (d, J=8.4 Hz, 2H), 8.95 (br s, 1H), 10.48 (br s, 2H); APCI-MS (m/z) 181 (M+H)+.

Step 2: Ethyl 4-{2-[(2-aminophenyl)carbonyl]hydrazinyl}benzoate

To a solution of Step 1 intermediate (2 g, 9.25 mmol) in ethanol (30 mL) was added DIPEA (1.4 mL, 0.87 mmol) and stirred for 15 min at RT. Isatoic anhydride (1.5 g, 9.250 mmol) was added to the reaction mixture and refluxed for 16 h. The reaction mixture was concentrated under reduced pressure to yield a sticky residue which was purified by silica gel column chromatography to yield 516 mg of the title product as off white solid; $^1$H NMR (300 MHz, DMSO-$d_6$) δ 1.27 (t, J=6.9 Hz, 3H), 4.22 (q, J=6.9 Hz, 2H), 6.39 (br s, 2H), 6.55 (t, J=6.9 Hz, 1H), 6.71-6.79 (m, 3H), 7.19 (t, J=6.9 Hz, 1H), 7.65 (d, J=7.8 Hz, 1H), 7.76 (d, J=8.4 Hz, 2H), 8.51 (br s, 1H), 10.48 (br s, 1H).

Step 3: Ethyl 4-(3-hydroxy-1H-indazol-1-yl)benzoate

To a well stirred and cooled (0° C.) solution of Step 2 intermediate (200 mg, 0.668 mmol) in 1M HCl (2 mL) was added aqueous solution of sodium nitrite (90 mg, 1.336 mmol) in portions. The reaction mixture was gradually allowed to warm up to room temperature, then added ethanol-water mixture (1:1 ratio, 10 mL) and refluxed for 3 h. The precipitate obtained was filtered and washed with water (10 mL). The product was recrystallized from diethyl ether (15 mL) and n-pentane (15 mL) to yield 130 mg of the title product as off-white solid; $^1$H NMR (300 MHz, DMSO-$d_6$) δ 1.30 (t, J=6.6 Hz, 3H), 4.33 (q, J=6.9 Hz, 2H), 7.23 (t, J=7.5 Hz, 1H), 7.54 (t, J=7.5 Hz, 1H), 7.79 (d, J=7.2 Hz, 1H), 7.87 (d, J=8.4 Hz, 2H), 7.94 (d, J=8.4 Hz, 1H), 8.09 (d, J=8.1 Hz, 2H), 11.58 (br s, 1H); APCI-MS (m/z) 283 (M+H)+.

Intermediate 2

Ethyl 3-fluoro-4-(3-hydroxy-1H-indazol-1-yl)benzoate

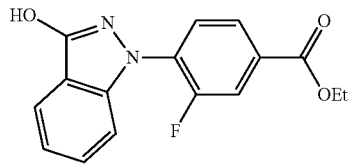 [SMILES: CCOC(=O)c1ccc(-n2nc(O)c3ccccc32)c(F)c1]

Step 1: Ethyl 3-fluoro-4-hydrazinylbenzoate hydrochloride

To a stirred and cooled (−20° C.) solution of ethyl 4-amino-3-fluorobenzoate (18 g, 98.809 mmol) in conc. HCl (200 mL) was added aqueous solution of NaNO$_2$ (7.5 g, 108.69 mmol). This mixture was added very slowly to a precooled (−10° C.) mixture of and tin chloride (100 g, 444.7 mmol) in conc. HCl (80 mL) and stirred at the same temperature for 30 min. The precipitate obtained was filtered and washed with diethyl ether (2×100 mL) to obtain 19.6 g of the title compound as white solid. $^1$H NMR (300 MHz, DMSO-$d_6$) δ 1.30 (t, J=7.2 Hz, 3H), 4.27 (q, J=6.9 Hz, 2H), 7.19 (t, J=8.1 Hz, 1H), 7.67 (d, J=8.1 Hz, 1H), 7.78 (d, J=8.4 Hz, 1H), 8.94 (br s, 1H), 10.50 (br s, 2H); APCI-MS (m/z) 199 (M+H)+.

Step 2: Ethyl 4-{2-[(2-aminophenyl)carbonyl]hydrazinyl}-3-fluorobenzoate

To a stirred solution of 2-aminobenzoic acid (19.5 g, 83.28 mmol) in DMF (400 mL) were added Step 1 intermediate (11.4 g, 83.28 mmol), EDCI (24 g, 124.9 mmol), HOBt (17 g, 124.9 mmol) and N-methylmorpholine (45.8 mL, 416.41 mmol). The reaction mixture was stirred at RT for 16 h. The reaction mixture was quenched with water (500 mL). The precipitate obtained was filtered, washed with water (3×200 mL) and the solid obtained was triturated with diethyl ether (50 mL) and n-pentane (100 mL) to yield 11.9 g of the title product as off white solid. $^1$H NMR (300 MHz, DMSO-$d_6$) δ 1.28 (t, J=7.4 Hz, 3H), 4.24 (q, J=6.9 Hz, 2H), 6.43 (br s, 2H), 6.55 (br s, 1H), 6.73 (d, J=7.8 Hz, 1H), 6.83 (br s, 1H), 7.20 (br s, 1H), 7.56-7.65 (m, 3H), 8.47 (m, 1H), 10.26 (br s, 1H); APCI-MS (m/z) 318 (M+H)+.

Step 3: Ethyl 3-fluoro-4-(3-hydroxy-1H-indazol-1-yl)benzoate

To a stirred and cooled (0° C.) solution of Step 2 intermediate (11.8 g, 37.18 mmol) in 1M HCl (100 mL) was added aqueous solution of sodium nitrite (5.2 g, 74.37 mmol) in portions. The reaction mixture was gradually allowed to warm up to room temperature, then added ethanol-water mixture (1:1 ratio, 100 mL) and refluxed for 3 h. The precipitate obtained was filtered and washed with water (50 mL). The product was recrystallized from diethyl ether (50 mL) and n-pentane (50 mL) to yield 8.9 g of the title product as off white solid. $^1$H NMR (300 MHz, DMSO-$d_6$) δ 1.34 (t, J=7.5 Hz, 3H), 4.36 (q, J=7.2 Hz, 2H), 7.21 (t, J=7.4 Hz, 1H), 7.38 (br s, 1H), 7.49 (br s, 1H), 7.73-7.79 (m, 2H), 7.92-7.98 (m, 2H), 11.55 (br s, 1H); APCI-MS (m/z) 301 (M+H)+.

Intermediate 3

Ethyl 3-fluoro-4-(7-fluoro-3-hydroxy-1H-indazol-1-yl)benzoate

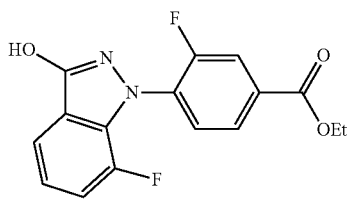 [SMILES: CCOC(=O)c1ccc(-n2nc(O)c3cccc(F)c32)c(F)c1]

Step 1: Ethyl 4-{2-[(2-amino-3-fluorophenyl)carbonyl]hydrazinyl}-3-fluorobenzoate To a stirred and cooled (0° C.) solution of 2-amino-3-fluorobenzoic acid (136 mg, 0.879 mmol) in DMF (8 mL) were added ethyl 3-fluoro-4-hydrazinylbenzoate hydrochloride (206 mg, 0.879 mmol), EDCI (185 mg, 0.966 mmol), HOBt (130 mg, 0.966 mmol) and N-methylmorpholine (0.29 mL, 2.637 mmol). The reaction mixture was stirred at 0° C. for 2 h. The reaction mixture was poured in to water (50 mL). The precipitate obtained was filtered, dried and purified by silica gel column chromatography to yield 116 mg of the title product as off white solid. $^1$H NMR (300 MHz, DMSO-$d_6$) δ 1.28 (t, J=7.5 Hz, 3H), 4.24 (q, J=6.9 Hz, 2H), 6.36 (br s, 2H), 6.54-6.63 (m, 1H), 6.84 (t, J=8.7 Hz, 1H), 7.18-7.27 (m, 1H), 7.53-9.59 (m, 2H), 7.64 (d, J=8.7 Hz, 1H), 8.54 (br s, 1H), 10.40 (br s, 1H).

Step 2: Ethyl 3-fluoro-4-(7-fluoro-3-hydroxy-1H-indazol-1-yl)benzoate

To a stirred and cooled (0° C.) solution of Step 1 intermediate (2 g, 5.964 mmol) in 1M HCl (30 mL) was added aqueous solution of sodium nitrite (823 mg, 11.928 mmol) in portions. The reaction mixture was gradually allowed to warm up to room temperature and allowed to settle. The precipitate obtained was filtered and purified by silica gel column chromatography to yield 346 mg of the title product as off white solid. $^1$H NMR (300 MHz, DMSO-$d_6$) δ 1.34 (t, J=7.2 Hz, 3H), 4.35 (q, J=7.5 Hz, 2H), 7.13-7.20 (m, 1H), 7.30-7.37 (m, 1H), 7.60 (d, J=7.8 Hz, 1H), 7.76 (t, J=7.8 Hz, 1H), 7.92 (d, J=9.3 Hz, 2H), 11.70 (br s, 1H).

Intermediate 4

Ethyl 4-(1H-indol-1-yl)benzoate

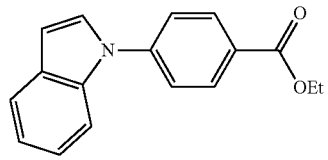 [SMILES: CCOC(=O)c1ccc(-n2ccc3ccccc32)cc1]

To the stirred solution of indole (700 mg, 5.975 mmol) in DMSO (7 mL) were added ethyl 4-iodobenzoate (2.47 g, 8.692 mmol), potassium carbonate (3.3 g, 23.9 mmol), L-proline (275 mg, 2.390 mmol) and copper iodide (227 mg, 1.195 mmol) and the reaction was stirred at 100° C. for 16 h. The reaction mixture was diluted with water (50 mL) and extracted with ethyl acetate (3×100 mL). The combined organic layers were washed with water (2×100 mL), brine (50 mL) and dried over anhydrous sodium sulfate. The solvent was distilled off under reduced pressure and residue thus obtained was purified by silica gel column chromatography to yield 900 mg of the title product as off white solid. $^1$H NMR (300 MHz, CDCl$_3$) δ 1.43 (t, J=6.9 Hz, 3H), 4.42 (q, J=6.9 Hz, 2H), 6.72 (s, 1H), 7.17-7.22 (m, 2H), 7.37 (s, 1H), 7.58-7.65 (m, 3H), 7.69 (d, J=7.2 Hz, 1H), 8.20 (d, J=8.4 Hz, 2H); APCI-MS (m/z) 266 (M+H)$^+$.

Intermediate 5

Ethyl 3-fluoro-4-(1H-indol-1-yl)benzoate

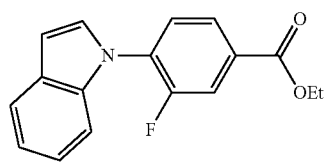 [SMILES: CCOC(=O)c1ccc(-n2ccc3ccccc32)c(F)c1]

To the stirred solution of indole (300 mg, 2.560 mmol) in DMSO (5 mL) were added ethyl 3-fluoro-4-iodobenzoate (1.13 mg, 3.84 mmol), potassium carbonate (1.41 g, 10.242 mmol), L-proline (300 mg, 2.560 mmol) and copper iodide (96 mg, 0.516 mmol) and the reaction was stirred at 100° C. for 16 h. The reaction mixture was diluted with water (50 mL) and extracted with ethyl acetate (3×100 mL). The combined organic layers were washed with water (2×100 mL), brine (50 mL) and dried over anhydrous sodium sulfate. The solvent was distilled off under reduced pressure and residue thus obtained was purified by silica gel column chromatography to yield 305 mg of the title product as colorless liquid. $^1$H NMR (300 MHz, DMSO-$d_6$) δ 1.35 (t, J=6.9 Hz, 3H), 4.37 (q, J=7.5 Hz, 2H), 6.78 (br s, 1H), 7.16-7.22 (m, 2H), 7.31 (br s, 1H), 7.63 (br s, 1H), 7.68 (d, J=7.8 Hz, 1H), 7.82 (t, J=8.4 Hz, 1H), 7.95-8.02 (m, 2H); APCI-MS (m/z) 284 (M+H)$^+$.

Intermediate 6

[2-Chloro-6-(trifluoromethyl)phenyl](1H-indol-3-yl)methanone

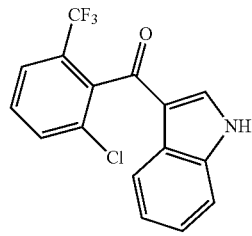 [SMILES: O=C(c1c(Cl)cccc1C(F)(F)F)c1c[nH]c2ccccc12]

To a stirred solution of indole (300 mg, 2.560 mmol) in DCM (10 mL) was added zinc chloride (767 mg, 5.633 mmol) followed by ethyl magnesium bromide (1.02 ml, 3.072 mmol) and stirred at RT for 1 h. 2-chloro-6-(trifluoromethyl)benzoyl chloride (933 mg, 3.841 mmol) was added to the reaction mixture and continued to stir at the same temperature. After 1 h, aluminium chloride (170 mg, 1.280 mmol) was added to the reaction mixture and further stirred at RT for 20 h. The reaction mixture was quenched with aqueous solution of ammonium chloride (50 mL) and the layers were separated. The aqueous layer was extracted with ethyl acetate (2×100 mL) and the combined organic extracts were washed with water (2×50 mL) and brine (50 mL). The organic layer was dried over anhydrous sodium sulfate and concentrated under reduced pressure to yield the 170 mg of the title product as off white solid. $^1$H NMR (300 MHz, DMSO-$d_6$) δ 7.28 (br s, 2H), 7.51 (d, J=8.4 Hz, 1H), 7.65 (br s, 1H), 7.74 (t, J=7.8 Hz, 1H), 7.87-7.93 (m, 2H), 8.24 (br s, 1H), 12.16 (br s, 1H); APCI-MS (m/z) 324 (M+H)$^+$.

Intermediate 7

Ethyl 3-fluoro-4-(4-fluoro-1H-indol-1-yl)benzoate

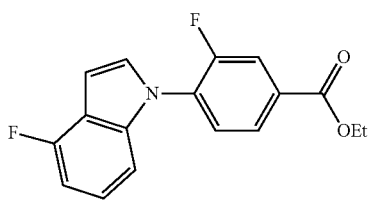 [SMILES: CCOC(=O)c1ccc(-n2ccc3c(F)cccc32)c(F)c1]

The title compound was prepared by the reaction of 4-fluoroindole (500 mg, 3.699 mmol) with ethyl 3-fluoro-4-iodobenzoate (1.30 mg, 4.439 mmol) in the presence of potassium carbonate (2.04 g, 14.799 mmol), L-proline (170 mg, 1.479 mmol) and copper iodide (140 mg, 0.739 mmol) in DMSO (10 mL) as per the process described in Intermediate 4 to yield 410 mg of product as off white solid. $^1$H NMR (300 MHz, CDCl$_3$) δ 1.43 (t, J=7.5 Hz, 3H), 4.43 (q, J=7.5 Hz, 2H), 6.83 (br s, 1H), 6.89 (d, J=9.3 Hz, 1H), 7.11-7.17 (m, 2H), 7.27 (d, J=7.5 Hz, 1H), 7.60 (t, J=7.8 Hz, 1H), 7.98 (d, J=9.6 Hz, 2H); APCI-MS (m/z) 302 (M)$^+$.

Intermediate 8

Ethyl 3-fluoro-4-(5-fluoro-1H-indol-1-yl)benzoate

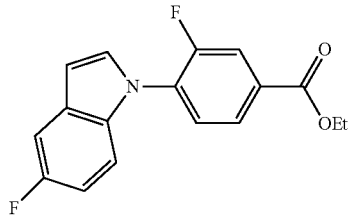 [SMILES: CCOC(=O)c1ccc(-n2ccc3cc(F)ccc32)c(F)c1]

The title compound was prepared by the reaction of 5-fluoroindole (500 mg, 3.699 mmol) with ethyl 3-fluoro-4-iodobenzoate (1.63 g, 5.549 mmol) using potassium carbonate (2.04 g, 14.799 mmol), L-proline (170 mg, 1.479 mmol) and copper iodide (140 mg, 0.739 mmol) in DMSO (10 mL) as per the process described in Intermediate 4 to yield 300 mg of product as off white solid. $^1$H NMR (300 MHz, DMSO-d$_6$) δ 1.35 (t, J=6.9 Hz, 3H), 4.37 (q, J=7.5 Hz, 2H), 6.78 (s, 1H), 7.07 (t, J=8.7 Hz, 1H), 7.31 (br s, 1H), 7.46 (t, J=9.3 Hz, 1H), 7.71 (s, 1H), 7.81 (t, J=7.8 Hz, 1H), 7.94-8.01 (m, 2H); APCI-MS (m/z) 302 (M+H)$^+$.

Intermediate 9

Ethyl 3-fluoro-4-(6-fluoro-1H-indol-1-yl)benzoate

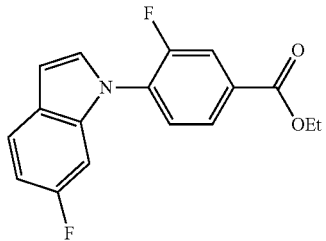 [SMILES: CCOC(=O)c1ccc(-n2ccc3ccc(F)cc32)c(F)c1]

The title compound was prepared by the reaction of 6-fluoroindole (500 mg, 3.699 mmol) with ethyl 3-fluoro-4-iodobenzoate (1.30 mg, 4.439 mmol) using potassium carbonate (2.04 g, 14.799 mmol), L-proline (170 mg, 1.479 mmol) and copper iodide (140 mg, 0.739 mmol) in DMSO (10 mL) as per the process described in Intermediate 4 to yield 314 mg of product as off white solid. $^1$H NMR (300 MHz, CDCl$_3$) δ 1.35 (br s, 3H), 4.35 (br s, 2H), 6.79 (br s, 1H), 7.04 (t, J=7.4 Hz, 1H), 7.13 (br s, 1H), 7.64 (br s, 2H), 7.82 (br s, 1H), 7.97 (br s, 2H); APCI-MS (m/z) 302 (M+H)$^+$.

Intermediate 10

Ethyl 3-fluoro-4-(7-fluoro-1H-indol-1-yl)benzoate

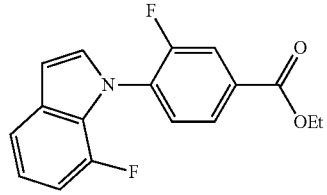 [SMILES: CCOC(=O)c1ccc(-n2ccc3cccc(F)c32)c(F)c1]

The title compound was prepared by the reaction of 7-fluoroindole (500 mg, 3.699 mmol) with ethyl 3-fluoro-4-iodobenzoate (1.30 g, 4.439 mmol) using potassium carbonate (2.04 g, 14.799 mmol), L-proline (170 mg, 1.479 mmol) and copper iodide (140 mg, 0.739 mmol) in DMSO (10 mL) as per the process described in Intermediate 4 to yield 351 mg of product as off white solid. $^1$H NMR (300 MHz, DMSO-d$_6$) δ 1.35 (t, J=6.9 Hz, 3H), 4.37 (q, J=6.9 Hz, 2H), 6.84 (br s, 1H), 6.92-7.06 (m, 1H), 7.11 (br s, 1H), 7.39 (br s, 1H), 7.50 (d, J=7.2 Hz, 1H), 7.61 (s, 1H), 7.79 (t, J=8.4 Hz, 1H), 7.93 (d, J=9.3 Hz, 1H); APCI-MS (m/z) 302 (M+H)$^+$.

Intermediate 11

Ethyl 4-[6-(dimethylcarbamoyl)-1H-indol-1-yl]-3-fluorobenzoate

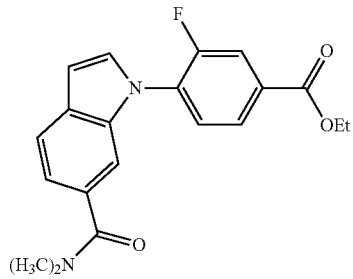

Step 1: N,N-dimethyl-1H-indole-6-carboxamide

To a stirred suspension of indole-6-carboxylic acid (1.5 g, 9.307 mmol) in acetonitrile (15 mL) were added EDCI.HCl (3.55 g, 18.61 mmol), HOBt (2.51 g, 18.6 mmol), triethylamine (4.03 mL, 27.9 mmol) and stirred at RT for 15 min. To the reaction mixture was added dimethylamine hydrochloride (2.27 g, 27.92 mmol) and continued to stir at RT for 3 hours. The reaction mixture was concentrated and the residue was diluted with water (10 mL). The aqueous mixture was extracted with ethyl acetate (2×15 mL). The combined organic layers were washed with brine (20 mL) and dried over anhydrous sodium sulfate. The solvents were removed under reduced pressure and residue obtained was purified by column chromatography to yield 1.22 g of the title product as white solid. $^1$H NMR (300 MHz, CDCl$_3$) δ 3.07 (br s, 6H), 6.53 (s, 1H), 7.12 (d, J=8.4 Hz, 1H), 7.27 (d, J=3.9 Hz, 1H), 7.50 (s, 1H), 7.61 (d, J=8.1 Hz, 1H), 9.21 (br s, 1H); APCI-MS (m/z) 189 (M+H)$^+$.

Step 2: Ethyl 4-[6-(dimethylcarbamoyl)-1H-indol-1-yl]-3-fluorobenzoate

The title compound was prepared by the reaction of step 1 intermediate (500 mg, 2.65 mmol) with ethyl 3-fluoro-4-iodobenzoate (859 mg, 2.92 mmol) using potassium carbonate (1.47 g, 10.6 mmol), L-proline (122 mg, 1.065 mmol) and copper iodide (100 mg, 0.531 mmol) in DMSO (5 mL) as per the process described in Intermediate 4 to yield 475 mg of product as glassy liquid. $^1$H NMR (300 MHz, DMSO-$d_6$) δ 1.35 (t, J=7.2 Hz, 3H), 2.94 (s, 6H), 4.36 (q, J=7.5 Hz, 2H), 6.84 (d, J=3.6 Hz, 1H), 7.21 (d, J=7.8 Hz, 1H), 7.33 (br s, 1H), 7.70-7.73 (m, 2H), 7.83 (t, J=8.4 Hz, 1H), 7.99 (t, J=9.3 Hz, 2H); APCI-MS (m/z) 355 (M+H)$^+$.

Intermediate 12

Ethyl 3-fluoro-4-(1H-pyrrolo[2,3-b]pyridin-1-yl)benzoate

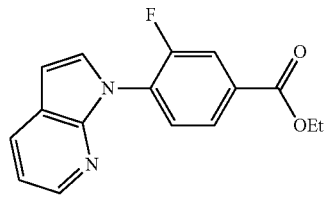 [SMILES: CCOC(=O)c1ccc(-n2ccc3cccnc32)c(F)c1]

The title compound was prepared by the reaction of 7-azaindole (500 mg, 4.232 mmol) with ethyl 3-fluoro-4-iodobenzoate (1.493 mg, 5.078 mmol) using potassium carbonate (2.33 g, 16.928 mmol), L-proline (194 mg, 1.692 mmol) and copper iodide (161 mg, 0.846 mmol) in DMSO (5 mL) as per the process described in Intermediate 4 to yield 311 mg of product as off white solid. $^1$H NMR (300 MHz, CDCl$_3$) δ 1.35 (t, J=6.9 Hz, 3H), 4.37 (q, J=7.5 Hz, 2H), 6.79 (br s, 1H), 7.24 (br s, 1H), 7.82 (br s, 1H), 7.97 (br s, 3H), 8.11 (d, J=7.2 Hz, 1H), 8.30 (br s, 1H); APCI-MS (m/z) 285 (M+H)$^+$.

Intermediate 13

1H-Indazol-3-yl(phenyl)methanone

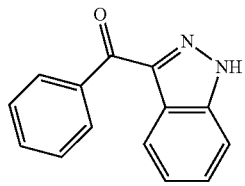 [SMILES: O=C(c1ccccc1)c1n[nH]c2ccccc12]

Step 1: 1H-Indazole-3-carboxylic acid

To a stirred aqueous solution of sodium hydroxide (35 mL, NaOH) was added isatine (5 g, 33.98 mmol) and the mixture was heated to 50° C. After 10 min, the reaction mixture was cooled down to 0° C. A precooled (0° C.) aqueous mixture of sodium nitrite (2.34 g, 33.98 mmol) and conc. H$_2$SO$_4$ (3.5 mL) were added to the reaction mass and stirred for 1 h at the same temperature. To the reaction mass were slowly added conc. HCl (30 mL) and tin chloride (14.8 g, 78.16 mmol). The reaction mixture was further stirred at RT for 16 h. The precipitate obtained was filtered and washed with water to yield 2.3 g of the title product as yellow solid. $^1$H NMR (300 MHz, DMSO-$d_6$) δ 7.27 (t, J=7.5 Hz, 1H), 7.43 (t, J=7.2 Hz, 1H), 7.64 (d, J=7.8 Hz, 1H), 8.07 (d, J=8.1 Hz, 1H), 12.85 (br s, 1H), 13.79 (br s, 1H).

Step 2: N-Methoxy-N-methyl-1H-indazole-3-carboxamide

To a stirred solution of step 1 intermediate (500 mg, 3.083 mmol) in THF (20 mL) was added N,O-dimethylhydroxylamine hydrochloride (360 mg, 3.70 mmol). The reaction mixture was cooled to 0° C. and added pyridine (2.5 mL). The reaction mixture was stirred at the same temperature for 2 h and then at room temperature for 1 h. To the reaction mixture was added some more pyridine (2 mL) followed by EDCI.HCl (1.18 g, 6.167 mmol) and further stirred at RT for 16 h. The reaction mixture was diluted with water (10 mL) and extracted with ethyl acetate (3×15 mL). The combined organic layers were washed with water (2×15 mL), brine (20 mL) and dried over anhydrous sodium sulfate. The solution was concentrated under reduced pressure and the residue thus obtained was purified by silica gel column chromatography to yield 361 mg of the title product as off white solid. $^1$H NMR (300 MHz, DMSO-$d_6$) δ 3.55 (s, 3H), 3.82 (s, 3H), 7.32 (t, J=7.5 Hz, 1H), 7.49 (t, J=6.9 Hz, 1H), 7.64 (d, J=8.4 Hz, 1H), 8.23 (d, J=8.4 Hz, 1H), 13.62 (br s, 1H).

Step 3: 1H-Indazol-3-yl(phenyl)methanone

To a stirred solution of Step 2 intermediate (350 mg, 1.705 mmol) in dry THF (2 mL) was added solution of phenyl magnesium bromide (1.55 g, 8.527 mmol) and the mixture was stirred at 80° C. for 15 min. The reaction mass was cooled to room temperature and stirred for 1 h. Aqueous ammonium chloride solution (35 mL) was added slowly to the reaction mass and extracted with ethyl acetate (3×50 mL). The combined organic layers were washed with water (2×50 mL), brine (50 mL) and dried over anhydrous sodium sulfate. The solvents were distilled off under reduced pressure and the residue thus obtained was purified by silica gel column chromatography to yield 303 mg of the title product as off white solid. $^1$H NMR (300 MHz, CDCl$_3$) δ 7.39 (br s, 1H), 7.50-7.62 (m, 5H), 8.29 (d, J=7.2 Hz, 2H), 8.48 (d, J=7.8 Hz, 1H); APCI-MS (m/z) 223 (M+H)$^+$.

Intermediate 14

(2,6-Dichlorophenyl)(1H-indazol-3-yl)methanone

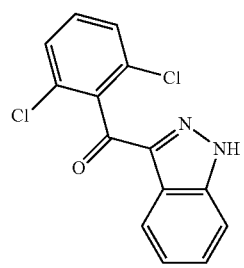 [SMILES: O=C(c1c(Cl)cccc1Cl)c1n[nH]c2ccccc12]

Step 1: 3-Iodo-1-(4-methoxybenzyl)-1H-indazole

To a stirred solution of 3-iodo-1H-indazole (10 g, 40.978 mmol) in DMF (50 mL) was added sodium hydride (60% w/w, 2.45 g, 61.250 mmol) in portions and the mixture was stirred at RT for 45 min. To this mixture was slowly added a solution of 1-(chloromethyl)-4-methoxybenzene (8.37 mL, 51.464 mmol) in DMF (50 mL) and further stirred for 18 h at RT. The reaction mixture was quenched with aqueous ammonium chloride solution (200 mL) and extracted with ethyl acetate (3×350 mL). The combined organic layers were washed with water (3×200 mL), brine (200 mL) and dried over anhydrous sodium sulfate. The solvents were removed under reduced pressure and residue obtained was purified by silica gel column chromatography to yield 10.2 g of the title product as off white solid. $^1$H NMR (300 MHz, DMSO-$d_6$) δ 3.70 (s, 3H), 5.59 (s, 2H), 6.86 (d, J=8.4 Hz, 2H), 7.18-7.26 (m, 3H), 7.41-7.49 (m, 2H), 7.76 (d, J=8.1 Hz, 1H); APCI-MS (m/z) 364 (M+H)$^+$.

Step 2: (2,6-Dichlorophenyl)[1-(4-methoxybenzyl)-1H-indazol-3-yl]methanol

To a stirred solution of step 1 intermediate (5 g, 13.729 mmol) in THF (30 mL) was slowly added isopropyl magnesium chloride (10.3 mL, 20.594 mmol) at −10° C. and stirred at the same temperature for 1 h. A solution of 2,6-dichlorobenzaldehyde (3.6 g, 20.594 mmol) in THF (10 mL) was added to the reaction mixture at −10° C. The reaction mixture was gradually warmed up to RT and stirred for 18 h. The reaction mixture was quenched with aqueous ammonium chloride (200 mL) and extracted with ethyl acetate (3×250 mL). The combined organic layers were washed with water (2×200 mL), brine (150 mL). The solution was dried over anhydrous sodium sulfate and concentrated under reduced pressure. The residue thus obtained was purified by silica gel column chromatography to yield 2.1 g of the title product as off white solid. $^1$H NMR (300 MHz, DMSO-$d_6$) δ 3.67 (s, 3H), 5.46 (s, 2H), 6.35 (br s, 1H), 6.78-6.84 (m, 3H), 7.07 (d, J=7.8 Hz, 3H), 7.28-7.37 (m, 2H), 7.46 (d, J=7.8 Hz, 2H), 7.54 (d, J=8.1 Hz, 1H), 7.84 (d, J=7.2 Hz, 1H); APCI-MS (m/z) 413 (M+H)$^+$.

Step 3: (2,6-Dichlorophenyl)[1-(4-methoxybenzyl)-1H-indazol-3-yl]methanone

To a stirred solution of Step 2 intermediate (2 g, 4.839 mmol) in DCM (20 mL) was added 1,1,1-triacetoxy-1,1-dihydro-1,2-benziodoxol-3(1H)-one (2.46 g, 5.805 mmol) and stirred at RT for 18 h. The reaction mixture was diluted with water (100 mL) and layers separated. The aqueous layer was extracted with ethyl acetate (3×150 mL). The combined organic extracts were washed with water (3×100 mL), aqueous solution of sodium bicarbonate (100 mL) and brine (100 mL). The solution was dried and the solvents were distilled off completely under reduced pressure to yield the 1.9 g of the title product as off white solid. $^1$H NMR (300 MHz, DMSO-$d_6$) δ 3.67 (s, 3H), 5.70 (s, 2H), 6.84 (d, J=8.4 Hz, 2H), 7.17 (d, J=7.8 Hz, 2H), 7.44 (t, J=7.2 Hz, 1H), 7.54-7.64 (m, 4H), 7.86 (d, J=8.1 Hz, 1H), 8.24 (d, J=8.4 Hz, 1H); APCI-MS (m/z) 411 (M+H)$^+$.

Step 4: (2,6-Dichlorophenyl)(1H-indazol-3-yl)methanone

To a well stirred solution of Step 3 intermediate (1.9 g, 4.619 mmol) in DCM (20 mL) was added trifluoroacetic acid (11 mL, 144.4 mmol) followed by trifluoromethane sulfonic acid (4 mL, 46.175 mmol) stirred at RT for 18 h. The reaction mixture was diluted with water (100 mL) and the layers were separated. The aqueous layer was extracted with ethyl acetate (3×100 mL) and the combined organic extracts were washed with water (2×100 mL), aqueous solution of sodium bicarbonate (100 mL) and brine (100 mL). The organic layer was dried (Na$_2$SO$_4$) and concentrated to dryness under reduced pressure to yield 750 mg of title product as off white solid. $^1$H NMR (300 MHz, DMSO-$d_6$) δ 7.41 (t, J=7.5 Hz, 1H), 7.49-7.59 (m, 4H), 7.73 (d, J=8.4 Hz, 1H), 8.23 (d, J=7.8 Hz, 1H), 14.07 (s, 1H); APCI-MS (m/z) 291 (M)+.

Intermediate 15 (2,6-dichlorophenyl)(7-fluoro-1H-indazol-3-yl)methanone

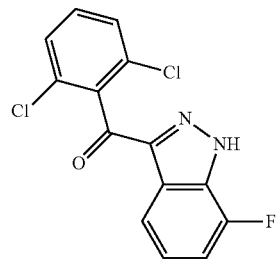 [SMILES: O=C(c1c(Cl)cccc1Cl)c1n[nH]c2c(F)cccc12]

Step 1:
7-Fluoro-3-iodo-1-(4-methoxybenzyl)-1H-indazole

The title compound was prepared by the reaction of 7-fluoro-3-iodo-1H-indazole (12.5 g, 47.70 mmol) with 1-(chloromethyl)-4-methoxybenzene (9.74 ml, 71.51 mmol) in the presence of sodium hydride (60% w/w, 3.06 g, 71.07 mmol) in DMF (50 mL) as per the process described in step 1 of Intermediate 14 to yield 10.1 g of the product as off white solid. $^1$H NMR (300 MHz, DMSO-d6) δ 3.69 (s, 3H), 5.61 (s, 2H), 6.87 (d, J=8.7 Hz, 2H), 7.14-7.21 (m, 3H), 7.26-7.36 (m, 2H); APCI-MS (m/z) 382 (M+H)$^+$.

Step 2: (2,6-Dichlorophenyl) [7-fluoro-1-(4-methoxybenzyl)-1H-indazol-3-yl]methanol The title compound was prepared by the reaction of Step 1 intermediate (5 g, 13.08 mmol) with 2,6-dichlorobenzaldehyde (3.43 g, 19.62 mmol) and isopropyl magnesium chloride (9.8 mL, 19.62 mmol) in THF (30 mL) as per the process described in step 2 of Intermediate 14 to yield 1.30 g of the product as yellow solid. $^1$H NMR (300 MHz, DMSO-$d_6$) δ 3.68 (s, 3H), 5.48 (s, 2H), 6.42-6.43 (m, 1H), 6.79-6.85 (m, 3H), 6.99-7.07 (m, 3H), 7.11-7.18 (m, 1H), 7.33-7.38 (m, 1H), 7.47 (d, J=7.8 Hz, 2H), 7.54 (d, J=8.1 Hz, 1H); APCI-MS (m/z) 430 (M+H)$^+$.

Step 3: (2,6-Dichlorophenyl) [7-fluoro-1-(4-methoxybenzyl)-1H-indazol-3-yl]methanone The title compound was prepared by oxidation of Step 2 intermediate (1.25 g, 2.89 mmol) with 1,1,1-triacetoxy-1,1-dihydro-1,2-benziodoxol-3(1H)-one (1.47 g, 3.47 mmol) in DCM (15 mL) as per the process described in step 3 of Intermediate 14 to yield the 1.10 g of the product as off white solid. $^1$H NMR (300 MHz, DMSO-$d_6$) δ 3.68 (s, 3H), 5.70

(s, 2H), 6.84 (d, J=8.1 Hz, 2H), 7.06 (d, J=8.1 Hz, 2H), 7.28-7.42 (m, 2H), 7.58-7.66 (m, 3H), 8.07 (d, J=7.2 Hz, 1H); APCI-MS (m/z) 430 (M+H)+.

Step 4: (2,6-Dichlorophenyl)(7-fluoro-1H-indazol-3-yl)methanone

The title compound was obtained by deprotection of Step 3 intermediate (1.10 g, 2.56 mmol) in the presence of trifluoroacetic acid (6 mL, 80.06 mmol) and trifluoromethane sulfonic acid (3.39 mL, 38.37 mmol) in DCM (15 mL) as per the process described in step 4 of Intermediate 14 to yield 600 mg of the product as yellow solid. $^1$H NMR (300 MHz, DMSO-d$_6$) δ 7.39-7.43 (m, 2H), 7.54-7.64 (m, 3H), 8.06 (d, J=5.4 Hz, 1H), 14.73 (s, 1H); APCI-MS (m/z) 308 (M)+.

Intermediate 16

[2-Chloro-6-(trifluoromethyl)phenyl](1H-indazol-3-yl)methanone

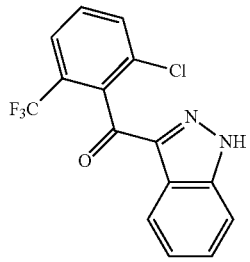 [SMILES: O=C(c1c(Cl)cccc1C(F)(F)F)c1n[nH]c2ccccc12]

Step 1: [2-Chloro-6-(trifluoromethyl)phenyl][1-(4-methoxybenzyl)-1H-indazol-3-yl]methanol The title compound was prepared by the Grignard reaction of 3-iodo-1-(4-methoxybenzyl)-1H-indazole (1.30 g, 3.56 mmol) with 2-chloro-6-(trifluoromethyl)benzaldehyde (0.93 g, 5.35 mmol) and isopropyl magnesium chloride (2.0 M in THF) (2.67 mL, 5.35 mmol) in THF (15 mL) as per the process described in step 2 of Intermediate 14 to yield 610 mg of the product as off white solid. $^1$H NMR (300 MHz, DMSO-d$_6$) δ 3.66 (s, 3H), 5.43 (s, 2H), 6.51 (d, J=6.0 Hz, 1H), 6.62 (d, J=5.7 Hz, 1H), 6.78 (d, J=9.0 Hz, 2H), 7.03-7.09 (m, 3H), 7.29-7.31 (m, 1H), 7.52-7.59 (m, 2H), 7.76-7.85 (m, 3H); APCI-MS (m/z) 446 (M+H)+.

Step 2: [2-Chloro-6-(trifluoromethyl)phenyl][1-(4-methoxybenzyl)-1H-indazol-3-yl]methanone The title compound was prepared by oxidation of Step 1 intermediate (0.6 g, 2.89 mmol) with 1,1,1-triacetoxy-1,1-dihydro-1,2-benziodoxol-3(1H)-one (0.68 g, 1.51 mmol) in DCM (10 mL) as per the process described in step 3 of Intermediate 14 to yield the 0.55 g of the product as off white solid. $^1$H NMR (300 MHz, DMSO-d$_6$) δ 3.67 (s, 3H), 5.68 (s, 2H), 6.83 (d, J=8.7 Hz, 2H), 7.14 (d, J=8.1 Hz, 2H), 7.44 (t, J=7.2 Hz, 1H), 7.54 (t, J=7.8 Hz, 1H), 7.76-7.98 (m, 4H), 8.24 (br s, 1H); APCI-MS (m/z) 489 (M+H)+.

Step 3: [2-Chloro-6-(trifluoromethyl)phenyl](1H-indazol-3-yl)methanone

The title compound was prepared by deprotection of Step 2 intermediate (0.55 g, 1.23 mmol) by using trifluoroacetic acid (2.95 mL, 38.58 mmol) and trifluoromethane sulfonic acid (1 mL, 12.32 mmol) in DCM (10 mL) as per the process described in step 4 Intermediate 14 to yield 250 mg of the product as off white solid. $^1$H NMR (300 MHz, DMSO-d$_6$) δ 7.43 (t, J=7.2 Hz, 1H), 7.54 (t, J=7.8 Hz, 1H), 7.73-7.7.80 (m, 2H), 7.89-7.95 (m, 2H), 8.24 (d, J=7.8 Hz, 1H), 14.06 (s, 1H); APCI-MS (m/z) 324 (M+H)+.

Intermediate 17

(2-Chloro-6-cyclopropylphenyl)(7-fluoro-1H-indazol-3-yl)methanone

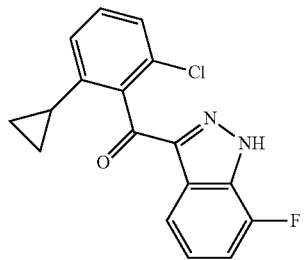 [SMILES: O=C(c1c(Cl)cccc1C1CC1)c1n[nH]c2c(F)cccc12]

Step 1: (2-Chloro-6-cyclopropylphenyl)[7-fluoro-1-(4-methoxybenzyl)-1H-indazol-3-yl]methanol To a stirred solution of 7-fluoro-3-iodo-1-(4-methoxybenzyl)-1H-indazole (1.2 g, 3.13 mmol) in THF (30 mL) was slowly added isopropyl magnesium chloride (2.35 mL, 4.71 mmol) at −10° C. and stirred at the same temperature for 1 h. A solution 2-chloro-6-cyclopropylbenzaldehyde (0.6 g, 3.76 mmol) in THF (15 mL) was added to the reaction mixture at −10° C. The reaction mixture was gradually warmed up to RT and stirred for 18 h. The reaction mixture was quenched with aqueous ammonium chloride (200 mL) and extracted with ethyl acetate (3×250 mL). The combined organic layers were washed with water (2×200 mL), brine (150 mL). The solution was dried over anhydrous sodium sulfate and concentrated under reduced pressure. The residue thus obtained was purified by silica gel column chromatography to yield 320 mg of the title product as yellow solid. $^1$H NMR (300 MHz, DMSO-d$_6$) δ 0.20-0.35 (m, 2H), 0.64-0.77 (m, 2H), 2.32-2.40 (m, 1H), 3.68 (s, 3H), 5.49 (s, 2H), 6.37 (d, J=4.2 Hz, 1H), 6.80-6.84 (m, 4H), 6.93-7.13 (m, 3H), 7.15-7.28 (m, 3H), 7.53 (d, J=7.8 Hz, 1H); APCI-MS (m/z) 436 (M+H)+.

Step 2: (2-Chloro-6-cyclopropylphenyl)[7-fluoro-1-(4-methoxybenzyl)-1H-indazol-3-yl]methanone To a stirred solution of Step 1 intermediate (1.20 g, 2.74 mmol) in DCM (15 mL) was added 1,1,1-triacetoxy-1,1-dihydro-1,2-benziodoxol-3(1H)-one (1.39 g, 3.29 mmol) and stirred at RT for 18 h. The reaction mixture was diluted with water (100 mL) and layers separated. The aqueous layer was extracted with ethyl acetate (3×150 mL). The combined organic extracts were washed with water (3×100 mL), aqueous solution of sodium bicarbonate (100 mL) and brine (100 mL). The solution was dried and the solvents were distilled off completely under reduced pressure to yield the 1.10 g of the title product as yellow solid. $^1$H NMR (300 MHz, DMSO-d$_6$) δ 0.58-1.00 (m, 4H), 1.62-1.78 (m, 1H), 3.68 (s, 3H), 5.69 (s, 2H), 6.84 (d, J=8.1 Hz, 2H), 7.02-7.09 (m, 3H), 7.36-7.41 (m, 4H), 8.08 (d, J=7.8 Hz, 1H)

Step 3: (2-Chloro-6-cyclopropylphenyl)(7-fluoro-1H-indazol-3-yl)methanone

Step 2 intermediate (1.0 g, 2.29 mmol) and trifluoroacetic acid (10 mL) were stirred at 75° C. for 1.5 hours. The excess reagent was removed under reduced pressure and the residue obtained was dissolved in water (10 mL). The aqueous mixture was basified with saturated sodium bicarbonate solution and extracted with ethyl acetate (2×15 mL). The combined organic extracts were washed with water (15 mL), brine (15 mL) and dried over anhydrous sodium sulfate. The solution was filtered and concentrated under reduced pressure. The residue thus obtained was purified by column chromatography to yield 490 mg of the title product as yellow solid. $^1$H NMR (300 MHz, DMSO-$d_6$) δ 0.65-0.84 (m, 4H), 1.59-1.64 (m, 1H), 7.01 (d, J=7.5 Hz, 1H), 7.34-7.41 (m, 4H), 8.03-8.06 (m, 1H), 14.60 (s, 1H).

Intermediate 18 (2,6-Dichlorophenyl)(1H-pyrazolo[3,4-b]pyridin-3-yl)methanone

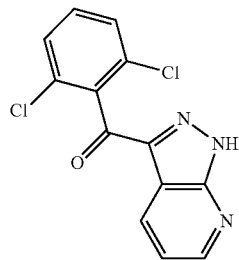 [SMILES: O=C(c1c(Cl)cccc1Cl)c1n[nH]c2ncccc12]

Step 1: 3-odo-1-(4-methoxybenzyl)-1H-pyrazolo[3,4-b]pyridine

The title compound was prepared by the reaction of 3-iodo-1H-pyrazolo[3,4-b]pyridine (4.90 g, 19.99 mmol) with 1-(chloromethyl)-4-methoxybenzene (4 mL, 29.9 mmol) in the presence of sodium hydride (60% w/w) (1.19 g, 29.5 mmol) in DMF (50 mL) as per the process described in step 1 of Intermediate 14 to yield 5.10 g of the product as off white solid. $^1$H NMR (300 MHz, DMSO-d6) δ 3.69 (s, 3H), 5.60 (s, 2H), 6.85 (d, J=8.7 Hz, 2H), 7.23 (d, J=8.7 Hz, 2H), 7.28-7.32 (m, 1H), 7.94 (d, J=8.4 Hz, 1H), 6.85 (d, J=8.7 Hz, 1H), 8.60-8.66 (m, 1H); APCI-MS (m/z) 366 (M+H)$^+$.

Step 2: (2,6-Dichlorophenyl)[1-(4-methoxybenzyl)-1H-pyrazolo[3,4-b]pyridin-3-yl]methanol The title compound was prepared by the Grignard reaction of Step 1 intermediate (5.00 g, 13.69 mmol) with 2,6-dichlorobenzaldehyde (3.50 g, 20.53 mmol) and isopropyl magnesium chloride (10 mL, 20.53 mmol) in THF (50 mL) as per the process described in step 2 of Intermediate 14 to yield 3.15 g of the product as off white solid. $^1$H NMR (300 MHz, DMSO-$d_6$) δ 3.67 (s, 3H), 5.50 (s, 2H), 6.50 (d, J=5.4 Hz, 1H), 6.78-6.84 (m, 3H), 7.05 (d, J=8.7 Hz, 2H), 7.17-7.22 (m, 1H), 7.33-7.38 (m, 1H), 7.45-7.47 (m, 2H), 8.30-8.32 (m, 1H), 8.52 (d, J=4.5 Hz, 1H); APCI-MS (m/z) 414 (M)$^+$.

Step 3: (2,6-Dichlorophenyl)[1-(4-methoxybenzyl)-1H-pyrazolo[3,4-b]pyridin-3-yl]methanone The title compound was prepared by oxidation reaction of Step 2 intermediate (3.10 g, 7.48 mmol) with 1,1,1-triacetoxy-1,1-dihydro-1,2-benziodoxol-3(1H)-one (3.80 g, 8.97 mmol) in DCM (30 mL) as per the process described in step 3 of Intermediate 14 to yield the 2.68 g of the product as off white solid. $^1$H NMR (300 MHz, DMSO-$d_6$) δ 3.68 (s, 3H), 5.72 (s, 2H), 6.82 (d, J=8.1 Hz, 2H), 7.16 (d, J=8.1 Hz, 2H), 7.54-7.65 (m, 4H), 8.63 (d, J=7.8 Hz, 1H), 8.76 (d, J=4.5 Hz, 1H); APCI-MS (m/z) 412 (M+H)$^+$.

Step 4: (2,6-Dichlorophenyl)(1H-pyrazolo[3,4-b]pyridin-3-yl)methanone

The title compound was prepared by the deprotection reaction of Step 3 intermediate (2.65 g, 6.42 mmol) by using trifluoroacetic acid (25 mL) as per the process described in step 3 of Intermediate 17 to yield 1.05 g of the product as brown solid. $^1$H NMR (300 MHz, DMSO-$d_6$) δ 7.48-7.45 (m, 1H), 7.56-7.64 (m, 3H), 8.62 (d, J=8.1 Hz, 1H), 8.72 (d, J=3.9 Hz, 1H), 14.74 (s, 1H); APCI-MS (m/z) 292 (M+H)$^+$.

Intermediate 19

(2-Chloro-6-cyclopropylphenyl)(1H-pyrazolo[3,4-b]pyridin-3-yl)methanone

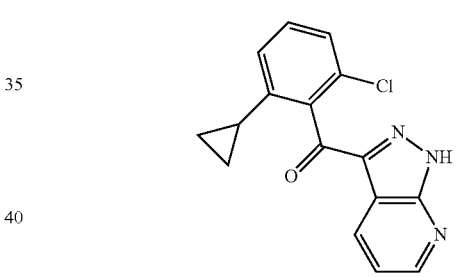

Step 1: (2-Chloro-6-cyclopropyl-phenyl)-[1-(4-methoxy-benzyl)-1H-pyrazolo[3,4-b]pyridin-3-yl]-methanol To a stirred solution of 3-iodo-1-(4-methoxybenzyl)-1H-pyrazolo[3,4-b]pyridine (3.50 g, 9.584 mmol) in THF (35 mL) was slowly added isopropyl magnesium chloride (2M in THF, 7.18 mL, 14.376 mmol) at −10° C. and stirred at the same temperature for 1 h. A solution of 2-chloro-6-cyclopropylbenzaldehyde (2.50 g, 14.376 mmol) in THF (10 mL) was added to the reaction mixture at −10° C. The reaction mixture was gradually warmed up to RT and stirred for 18 h. The reaction mixture was quenched with aqueous ammonium chloride (200 mL) and extracted with ethyl acetate (3×250 mL). The combined organic layers were washed with water (2×200 mL), brine (150 mL). The solution was dried over anhydrous sodium sulfate and concentrated under reduced pressure. The residue thus obtained was purified by silica gel column chromatography to yield 1.65 g of the title product as yellow solid. $^1$H NMR (300 MHz, DMSO-$d_6$) δ 0.12-0.13 (m, 2H), 0.67-0.72 (m, 2H), 2.28-2.31 (m, 1H), 3.67 (s, 3H), 5.42-5.56 (m, 2H), 6.43 (d, J=5.1 Hz, 1H), 6.78-6.84 (m, 3H), 6.92 (d, J=4.8 Hz, 1H), 7.09-7.27 (m, 5H), 8.13 (d, J=7.8 Hz, 1H), 8.50-8.51 (m, 1H); APCI-MS (m/z) 420 (M+H)+.

Step 2: (2-Chloro-6-cyclopropylphenyl)[1-(4-methoxybenzyl)-1H-pyrazolo[3,4-b]pyridin-3-yl]methanone To a stirred solution of step 1 intermediate (1.62 g, 3.858 mmol) in DCM (20 mL) was added 1,1,1-triacetoxy-1,1-dihydro-1,2-benziodoxol-3(1H)-one (1.96 g, 4.629 mmol) and stirred at RT for 18 h. The reaction mixture was diluted with water (100 mL) and layers separated. The aqueous layer was extracted with ethyl acetate (3×150 mL). The combined organic extracts were washed with water (3×100 mL), aqueous solution of sodium bicarbonate (100 mL) and brine (100 mL). The solution was dried and the solvents were distilled off completely under reduced pressure to yield the 1.56 g of the title product as off white solid. $^1$H NMR (300 MHz, DMSO-$d_6$) δ 0.58-0.62 (m, 2H), 0.63-0.85 (m, 2H), 1.59-1.62 (m, 1H), 3.68 (s, 3H), 5.71-5.73 (m, 2H), 6.82 (d, J=9.0 Hz, 2H), 7.04 (d, J=7.5 Hz, 1H), 7.15 (d, J=8.4 Hz, 2H), 7.40 (d, J=7.8 Hz, 2H), 7.51-7.55 (m, 1H), 8.63 (d, J=8.1 Hz, 1H), 8.74 (d, J=4.5 Hz, 1H); APCI-MS (m/z) 418 (M+H)+.

Step 3: (2-Chloro-6-cyclopropylphenyl)(1H-pyrazolo[3,4-b]pyridin-3-yl)methanone Step 2 intermediate (1.50 g, 3.589 mmol) and trifluoroacetic acid (20 mL) were stirred at 75° C. for 1.5 hours. The excess reagent was removed under reduced pressure and the residue obtained was dissolved in water (10 mL). The aqueous mixture was basified with saturated sodium bicarbonate solution and extracted with ethyl acetate (2×15 mL). The combined organic extracts were washed with water (15 mL), brine (15 mL) and dried over anhydrous sodium sulfate. The solution was filtered and concentrated under reduced pressure. The residue thus obtained was purified by column chromatography to yield 650 mg of the title product as brown solid. $^1$H NMR (300 MHz, DMSO-$d_6$) δ 0.66-0.67 (m, 2H), 0.68-0.83 (m, 2H), 1.62-1.64 (m, 1H), 7.04 (d, J=6.9 Hz, 1H), 7.34-7.50 (m, 3H), 8.62 (d, J=7.8 Hz, 1H), 8.68 (d, J=4.5 Hz, 1H), 14.59 (s, 1H); APCI-MS (m/z) 298 (M+H)+.

Intermediate 20

[2-Chloro-6-(trifluoromethyl)phenyl](1H-pyrazolo[3,4-b]pyridin-3-yl)methanone

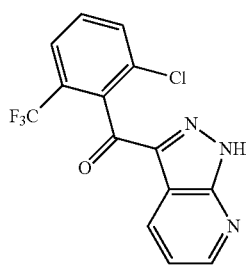 [SMILES: O=C(c1c(Cl)cccc1C(F)(F)F)c1n[nH]c2ncccc12]

Step 1: (2-Chloro-6-trifluoromethyl-phenyl)-[1-(4-methoxy-benzyl)-1H-pyrazolo[3,4-b]pyridin-3-yl]-methanol The title compound was prepared by the reaction of 3-iodo-1-(4-methoxybenzyl)-1H-pyrazolo[3,4-b]pyridine (1 g, 5.713 mmol) with 2-chloro-6-(trifluoromethyl)benzaldehyde (3.12 g, 18.570 mmol) and isopropyl magnesium chloride (2M in THF, 5.71 mL, 11.427 mmol) in THF (15 mL) as per the process described in step 2 of Intermediate 14 to yield 1.4 g of the product as off white solid. $^1$H NMR (300 MHz, DMSO-$d_6$) δ 3.67 (s, 3H), 5.48 (s, 2H), 6.63 (dd, J=5.4, 16.2 Hz, 2H), 6.78 (d, J=8.7 Hz, 2H), 7.03 (d, J=8.1 Hz, 2H), 7.18-7.23 (m, 1H), 7.57 (t, J=7.8 Hz, 1H), 7.75-7.82 (m, 2H), 8.28 (d, J=7.8 Hz, 1H), 8.52 (br s, 1H); APCI-MS (m/z) 448 (M+H)+.

Step 2: (2-Chloro-6-trifluoromethylphenyl) [1-(4-methoxybenzyl)-1H-pyrazolo[3,4-b]pyridin-3-yl]methanone The title compound was synthesized by the reaction of f Step 1 intermediate (1.4 g, 3.1261 mmol) with 1,1,1-triacetoxy-1,1-dihydro-1,2-benziodoxol-3(1H)-one (1.59 g, 3.751 mmol) in DCM (15 mL) as per the process described in step 3 of Intermediate 14 to yield the 1.52 g of the title product as off white solid. $^1$H NMR (300 MHz, DMSO-$d_6$) δ 3.67 (s, 3H), 5.70 (s, 2H), 6.82 (d, J=8.4 Hz, 2H), 7.13 (d, J=8.1 Hz, 2H), 7.53-7.58 (m, 1H), 7.80 (t, J=7.8 Hz, 1H), 7.92-7.99 (m, 2H), 8.63-8.67 (m, 1H), 8.75 (br s, 1H).

Step 3: [2-Chloro-6-(trifluoromethyl)phenyl](1H-pyrazolo[3,4-b]pyridin-3-yl)methanone The title compound was prepared by the N-deprotection reaction of Step 2 intermediate (1.5 g, 3.364 mmol) by using trifluoroacetic acid (20 mL) as per the process described in step 3 of Intermediate 17 to yield 650 mg of the product as brown solid. $^1$H NMR (300 MHz, DMSO-$d_6$) δ 7.48-7.53 (m, 1H), 7.79-7.83 (m, 1H), 7.94 (t, J=10.5 Hz, 2H), 8.62-8.72 (m, 2H), 14.72 (s, 1H); APCI-MS (m/z) 326 (M+H)+.

Examples

Example 1

4-[3-(2-Methylphenoxy)-1H-indazol-1-yl]benzoic acid

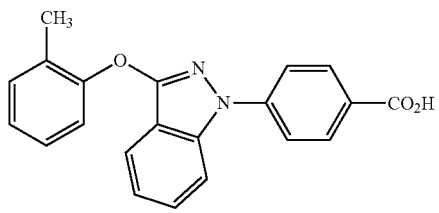 [SMILES: Cc1ccccc1Oc1nn(-c2ccc(C(=O)O)cc2)c2ccccc12]

Step 1: Ethyl 4-[3-(2-methylphenoxy)-1H-indazol-1-yl]benzoate

To a well stirred solution of Intermediate 1 (150 mg, 0.530 mmol) in DCM (6 mL) were added copper acetate (96 mg, 0.530 mmol), 2-methylphenyl boronic acid (144 mg, 1.06 mmol) followed by molecular sieves (120 mg) and the reaction mixture was degassed for 10 minutes. Triethylamine (0.36 mL, 2.65 mmol) was added to the reaction mixture and stirred at RT for 16 h. The reaction mixture was diluted with DCM (2 mL) and filtered. The filtration bed was washed with ethyl acetate (2×10 mL). The filtrate was concentrated under reduced pressure to yield a sticky residue which was purified by silica gel column chromatography to yield 86 mg of the desired product as off white solid; $^1$H NMR (300 MHz, DMSO-$d_6$) δ 1.33 (t, J=6.6 Hz, 3H), 2.30 (s, 3H), 4.33 (q, J=6.9 Hz, 2H), 7.18 (br s, 1H), 7.24-7.30 (m, 3H), 7.37 (br s, 1H), 7.62 (d, J=7.2 Hz, 2H), 7.84 (d, J=8.4 Hz, 2H), 8.00 (d, J=8.4 Hz, 1H), 8.09 (d, J=7.8 Hz, 2H); APCI-MS (m/z) 373 (M+H)$^+$.

Step 2: 4-[3-(2-Methylphenoxy)-1H-indazol-1-yl]benzoic acid

To a stirred and cooled (0° C.) solution of Step 1 intermediate (80 mg, 0.214 mmol) in a mixture of THF (3 mL), methanol (2 mL) and water (1 mL) was added lithium hydroxide (27 mg, 0.644 mmol). The reaction mixture was stirred at RT for 5 h. The solvents were distilled out under reduced pressure to afford the sticky residue which was diluted with water and acidified with 1N HCl. The precipitate thus obtained was filtered and washed with water. The obtained solid was purified by silica gel column chromatography to yield 23 mg of the title product as off white solid; $^1$H NMR (300 MHz, DMSO-$d_6$) δ 2.30 (s, 3H), 7.18 (br s, 1H), 7.24-7.32 (m, 3H), 7.37 (d, J=7.2 Hz, 1H), 7.61 (br s, 2H), 7.81 (d, J=7.8 Hz, 2H), 8.00 (d, J=8.1 Hz, 1H), 8.07 (d, J=7.8 Hz, 2H), 13.04 (br s, 1H); APCI-MS (m/z) 345 (M+H)$^+$.

Example 2

4-{3-[2-(Trifluoromethyl)phenoxy]-1H-indazol-1-yl}benzoic acid

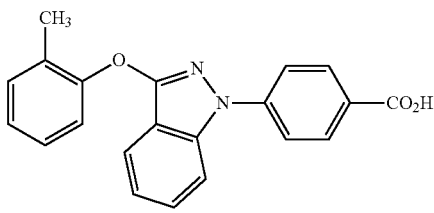 [SMILES: Cc1ccccc1Oc1nn(-c2ccc(C(=O)O)cc2)c2ccccc12]

Step 1: Ethyl 4-{3-[2-(trifluoromethyl)phenoxy]-1H-indazol-1-yl}benzoate

The title compound was prepared by the reaction of Intermediate 1 (200 mg, 0.707 mmol) with 2-(trifluoromethylphenyl)boronic acid (268 mg, 1.415 mmol) using copper acetate (130 mg, 0.707 mmol) and triethylamine (0.49 mL, 3.535 mmol) in DCM (10 mL) as per the process described in step 1 of Example 1 to yield 26 mg of the product as off white solid. $^1$H NMR (300 MHz, DMSO-$d_6$) δ 1.34 (t, J=6.9 Hz, 3H), 4.34 (q, J=6.9 Hz, 2H), 7.33 (t, J=7.2 Hz, 1H), 7.44 (t, J=7.8 Hz, 1H), 7.59-7.67 (m, 3H), 7.70 (t, J=7.8 Hz, 1H), 7.89 (d, J=7.8 Hz, 3H), 8.03 (d, J=8.7 Hz, 1H), 8.12 (d, J=8.1 Hz, 2H); ESI-MS (m/z) 427 (M+H)$^+$.

Step 2: 4-{3-[2-(Trifluoromethyl)phenoxy]-1H-indazol-1-yl}benzoic acid

The title compound was prepared by the hydrolysis of step 1 intermediate (60 mg, 0.140 mmol) using lithium hydroxide (18 mg, 0.422 mmol) in THF (3 mL), methanol (2 mL) and water (1 mL) as per the process described in step 2 of Example 1 to yield 19 mg of the product as off white solid; $^1$H NMR (300 MHz, DMSO-$d_6$) δ 7.33 (t, J=7.8 Hz, 1H), 7.44 (t, J=7.5 Hz, 1H), 7.59-7.66 (m, 3H), 7.71 (t, J=7.8 Hz, 1H), 7.87 (d, J=7.8 Hz, 3H), 8.03 (d, J=8.1 Hz, 1H), 8.10 (d, J=8.1 Hz, 2H), 13.07 (br s, 1H); APCI-MS (m/z) 397 (M−H)$^+$.

Example 3

4-[3-(3-Methylphenoxy)-1H-indazol-1-yl]benzoic acid

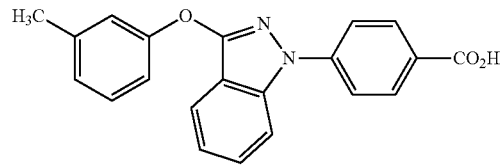 [SMILES: Cc1cccc(Oc2nn(-c3ccc(C(=O)O)cc3)c3ccccc23)c1]

Step 1: Ethyl 4-[3-(3-methylphenoxy)-1H-indazol-1-yl]benzoate

The title compound was prepared by the reaction of Intermediate 1 (200 mg, 0.707 mmol) with 3-(methylphenyl)boronic acid (105 mg, 0.778 mmol) using copper acetate (128 mg, 0.707 mmol) and triethylamine (0.49 mL, 3.535 mmol) in DCM (10 mL) as per the process described in step 1 of Example 1 to give 80 mg of the product as off white solid. $^1$H NMR (300 MHz, DMSO-$d_6$) δ 1.27 (t, J=7.2 Hz, 3H), 2.28 (s, 3H), 4.27 (q, J=7.2 Hz, 2H), 7.04 (br s, 1H), 7.30 (br s, 2H), 7.37-7.46 (m, 3H), 7.58 (d, J=7.8 Hz, 2H), 7.63-7.69 (m, 1H), 7.89 (d, J=7.5 Hz, 1H), 7.97 (d, J=8.4 Hz, 2H).

Step 2: 4-[3-(3-Methylphenoxy)-1H-indazol-1-yl]benzoic acid

The title compound was prepared by the hydrolysis of step 1 intermediate (80 mg, 0.214 mmol) using lithium hydroxide (36 mg, 0.856 mmol) in THF (3 mL), methanol (2 mL) and water (1 mL) as per the process described in step 2 of Example 1 to give 26 mg of the product as off white solid; $^1$H NMR (300 MHz, DMSO-$d_6$) δ 2.29 (s, 3H), 7.04 (br s, 1H), 7.30 (br s, 3H), 7.37-7.43 (m, 2H), 7.56 (d, J=7.8 Hz, 2H), 7.68 (br s, 1H), 7.89 (d, J=7.2 Hz, 1H), 7.95 (d, J=7.8 Hz, 2H), 12.96 (br s, 1H); APCI-MS (m/z) 345 (M+H)$^+$.

Example 4

4-(3-Phenoxy-1H-indazol-1-yl)benzoic acid

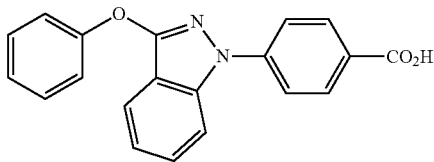 [SMILES: O=C(O)c1ccc(-n2nc(Oc3ccccc3)c3ccccc32)cc1]

Step 1: Ethyl 4-(3-phenoxy-1H-indazol-1-yl)benzoate

The title compound was prepared by the reaction of Intermediate 1 (200 mg, 0.707 mmol) with phenyl boronic acid (95 mg, 0.778 mmol) using copper acetate (130 mg, 0.707 mmol) and triethylamine (0.49 mL, 3.535 mmol) in DCM (10 mL) as per the process described in step 1 of Example 1 to give 115 mg of the product as brown solid. $^1$H NMR (300 MHz, DMSO-$d_6$) δ 1.27 (t, J=6.9 Hz, 3H), 4.27 (q, J=6.9 Hz, 2H), 7.21 (t, J=7.5 Hz, 1H), 7.38-7.48 (m, 4H), 7.58 (t, J=8.7 Hz, 4H), 7.70 (t, J=7.2 Hz, 1H), 7.86-7.98 (m, 3H); APCI-MS (m/z) 359 (M+H)$^+$.

Step 2: 4-(3-Phenoxy-1H-indazol-1-yl)benzoic acid

The title compound was synthesized by the hydrolysis of step 1 intermediate (110 mg, 0.307 mmol) using lithium hydroxide (51 mg, 1.229 mmol) in THF (3 mL), methanol (2 mL) and water (1 mL) as per the process described in step 2 of Example 1 to yield 55 mg of the product as off white solid; $^1$H NMR (300 MHz, DMSO-$d_6$) δ 7.21 (t, J=6.6 Hz, 1H), 7.38-7.47 (m, 4H), 7.56 (d, J=7.8 Hz, 4H), 7.69 (t, J=7.8 Hz, 1H), 7.89-7.96 (m, 3H), 13.07 (br s, 1H); APCI-MS (m/z) 331 (M+H)$^+$.

Example 5

4-[3-(2,6-Dichlorophenoxy)-1H-indazol-1-yl]benzoic acid

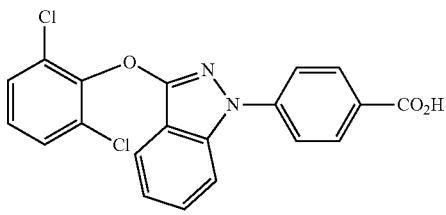 [SMILES: O=C(O)c1ccc(-n2nc(Oc3c(Cl)cccc3Cl)c3ccccc32)cc1]

Step 1: Ethyl 4-[3-(2,6-dichloro-4-nitrophenoxy)-1H-indazol-1-yl]benzoate

To a well stirred solution of Intermediate 1 (200 mg, 0.707 mmol) in DMF (3 mL) was added sodium hydride (60% w/w) (34 mg, 0.848 mmol) in small portions and the mixture was stirred at RT for 30 minutes. To the mixture was slowly added a solution of 3,5-dichloro-4-fluoronitrobenzene (165 mg, 0.778 mmol) in DMF (3 mL) and further stirred at RT for 16 h. The reaction mixture was quenched with aqueous solution of ammonium chloride (50 mL) and was extracted with ethyl acetate (2×100 mL). The combined organic layers were washed with water (2×50 mL), brine (50 mL), dried (Na$_2$SO$_4$) and concentrated under reduced pressure. The residue thus obtained was purified by silica gel column chromatography to yield 206 mg of the title product as off white solid; $^1$H NMR (300 MHz, DMSO-$d_6$) δ 1.31 (t, J=6.9 Hz, 3H), 4.31 (q, J=6.9 Hz, 2H), 7.41 (t, J=7.8 Hz, 1H), 7.68 (t, J=8.1 Hz, 1H), 7.74 (d, J=8.4 Hz, 2H), 7.95 (d, J=8.1 Hz, 1H), 8.01 (d, J=9.0 Hz, 1H), 8.07 (d, J=8.4 Hz, 2H), 8.60 (br s, 2H); APCI-MS (m/z) 472 (M)$^+$.

Step 2: Ethyl 4-[3-(4-amino-2,6-dichlorophenoxy)-1H-indazol-1-yl]benzoate

To a stirred solution of Step 1 intermediate (200 mg, 0.423 mmol) in a mixture of ethanol (5 mL) and water (1 mL) was added ammonium chloride (225 mg, 4.234 mmol) and the reaction was heated to 90° C. Iron powder (70 mg, 1.269 mmol) was added to the reaction mixture at 90° C. and the reaction was further stirred at same temperature for 2 h. The reaction mixture was filtered and solvents were distilled out under reduced pressure. The sticky residue obtained was diluted with ethyl acetate (250 mL). The layers were separated and the organic layer was washed with aqueous solution of sodium bicarbonate (50 mL) followed by brine (50 mL). The solvent was distilled off completely under reduced pressure to yield 160 mg of the title product as off white solid; $^1$H NMR (300 MHz, DMSO-$d_6$) δ 1.32 (t, J=6.6 Hz, 3H), 4.32 (q, J=7.2 Hz, 2H), 5.72 (s, 2H), 6.73 (s, 2H), 7.33 (t, J=7.5 Hz, 1H), 7.62 (t, J=7.4 Hz, 1H), 7.72-7.77 (m, 3H), 7.97 (d, J=8.7 Hz, 1H), 8.08 (d, J=8.4 Hz, 2H); APCI-MS (m/z) 442 (M)$^+$.

Step 3: Ethyl 4-[3-(2,6-dichlorophenoxy)-1H-indazol-1-yl]benzoate

To a stirred solution of tert butyl nitrite (0.05 mL, 0.395 mmol) in DMF (3 mL) was added a solution of step 2 intermediate (100 mg, 0.226 mmol) in DMF (3 mL) at 50° C. The reaction mixture was stirred at the same temperature for 30 minutes. The reaction mixture was quenched with 1N HCl (50 mL) and extracted with ethyl acetate (2×100 mL). The combined organic extracts were washed with water (2×50 mL) followed by brine (50 mL). The solution was dried over anhydrous sodium sulfate and concentrated under reduced pressure to yield 77 mg of the title product as off white solid; APCI-MS (m/z) 427 (M)$^+$.

Step 4: 4-[3-(2,6-Dichlorophenoxy)-1H-indazol-1-yl]benzoic acid

The title compound was prepared by the hydrolysis of Step 3 intermediate (70 mg, 0.163 mmol) using lithium hydroxide (16 mg, 0.655 mmol) in methanol (2 mL) and water (1 mL) as per the process described in step 2 of Example 1 to yield 26 mg of the product as off white solid; $^1$H NMR (300 MHz, DMSO-$d_6$) δ 7.37-7.46 (m, 2H), 7.64-7.71 (m, 5H), 7.88 (d, J=8.4 Hz, 1H), 7.99 (d, J=8.1 Hz, 1H), 8.06 (d, J=8.4 Hz, 2H), 13.02 (br s, 1H); APCI-MS (m/z) 399 (M+H)+.

Example 6

4-[3-(2,6-Dichlorophenoxy)-1H-indazol-1-yl]-3-fluorobenzoic acid

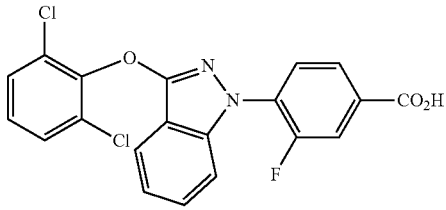 [SMILES: O=C(O)c1ccc(-n2nc(Oc3c(Cl)cccc3Cl)c3ccccc32)c(F)c1]

Step 1: Ethyl 4-[3-(4-amino-2,6-dichlorophenoxy)-1H-indazol-1-yl]-3-fluorobenzoate The title compound was prepared by the reaction of Intermediate 2 (200 mg, 0.665 mmol) with 3,5-dichloro-4-fluoronitrobenzene (155 mg, 0.731 mmol) in the presence of sodium hydride (60% w/w) (32 mg, 0.798 mmol) in DMF (6 mL) to give corresponding nitro intermediate (230 mg, 0.469 mmol) which was reduced by using ammonium chloride (250 mg, 4.691 mmol) and iron powder (79 mg, 1.407 mmol) in a mixture of ethanol (5 mL) and water (1 mL) as per the process described in step 1 and 2 of Example 5 to yield 190 mg of the product as off white solid. $^1$H NMR (300 MHz, CDCl$_3$) δ 1.37 (t, J=6.9 Hz, 3H), 4.38 (q, J=6.6 Hz, 2H), 7.19-7.34 (m, 4H), 7.35-7.36 (m, 2H), 7.51-7.53 (m, 2H), 7.82-7.91 (m, 3H); APCI-MS (m/z) 460 (M+H)+.

Step 2: Ethyl 4-[3-(2,6-dichlorophenoxy)-1H-indazol-1-yl]-3-fluorobenzoate

The title compound was prepared by the reaction of step 1 intermediate (150 mg, 0.325 mmol) with tert butyl nitrite (0.07 mL, 0.570 mmol) in DMF (6 mL) as per the process described in step 3 of Example 5 to yield 90 mg of the product. $^1$H NMR (300 MHz, CDCl$_3$) δ 1.40 (t, J=7.5 Hz, 3H), 4.34 (q, J=7.0 Hz, 2H), 7.18-7.21 (m, 1H), 7.26-7.36 (m, 1H), 7.41-7.44 (m, 2H), 7.50-7.53 (m, 2H), 7.83-8.02 (m, 3H).

Step 3: 4-[3-(2,6-Dichlorophenoxy)-1H-indazol-1-yl]-3-fluorobenzoic acid

The title compound was prepared by the hydrolysis of step 2 intermediate (90 mg, 0.202 mmol) using lithium hydroxide (34 mg, 0.808 mmol) in methanol (2 mL) and water (1 mL) as per the process described in step 2 of Example 1 to yield 15 mg of the product as off white solid; $^1$H NMR (300 MHz, CDCl$_3$) δ 7.16 (t, J=7.8 Hz, 1H), 7.28-7.32 (m, 2H), 7.40-7.46 (m, 2H), 7.50-7.57 (m, 2H), 7.86 (d, J=8.4 Hz, 1H), 7.93-7.99 (m, 2H); APCI-MS (m/z) 417 (M+H)+.

Example 7

4-{3-[2-Chloro-6-(trifluoromethyl)phenoxy]-1H-indazol-1-yl}-3-fluorobenzoic acid

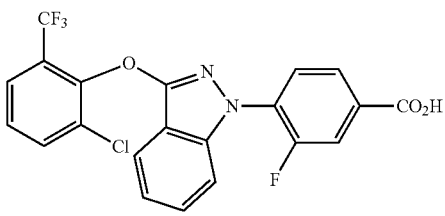 [SMILES: O=C(O)c1ccc(-n2nc(Oc3c(Cl)cccc3C(F)(F)F)c3ccccc32)c(F)c1]

Step 1: Ethyl 3-fluoro-4-{3-[2-nitro-6-(trifluoromethyl)phenoxy]-1H-indazol-1-yl}benzoate To a stirred solution of Intermediate 2 (900 mg, 2.994 mmol) in DMF (50 mL) was added sodium hydride (60% w/w) (143 mg, 3.593 mmol) and the reaction mixture was stirred for 30 min at RT. To the reaction mixture was added a solution of 2-fluoro-1-nitro-3-(trifluoromethyl)benzene (626 mg, 2.994 mmol) at RT and continued to stir for 16 hours. The reaction mixture was quenched with aqueous ammonium chloride solution (20 mL) and extracted with ethyl acetate (3×20 mL). The combined organic layers were washed with brine (50 mL) and dried over anhydrous sodium sulfate. The solvent was removed under reduced pressure and residue thus obtained was purified by silica gel column chromatography to obtain 665 mg of the title compound as brown oil. $^1$H NMR (300 MHz, CDCl$_3$) δ 1.40 (t, J=7.2 Hz, 3H), 4.39 (q, J=6.9 Hz, 2H), 7.32-7.41 (m, 2H), 7.46 (t, J=7.2 Hz, 1H), 7.51-7.59 (m, 2H), 7.90 (d, J=9.0 Hz, 3H), 8.02 (d, J=8.4 Hz, 1H), 8.27 (d, J=7.5 Hz, 1H).

Step 2: Ethyl 4-{3-[2-amino-6-(trifluoromethyl)phenoxy]-1H-indazol-1-yl}-3-fluorobenzoate A stirred suspension of step 1 intermediate (660 mg, 1.349 mmol) and catalytic amount of palladium on carbon in methanol (40 mL) was stirred under hydrogen pressure for 2 hours. The reaction mixture was filtered and the filtrate was concentrated to yield 510 mg of the title product as brown oil. $^1$H NMR (300 MHz, DMSO-d$_6$) δ 1.33 (t, J=6.9 Hz, 3H), 4.35 (q, J=6.6 Hz, 2H), 5.47 (s, 2H), 6.91 (d, J=7.2 Hz, 1H), 7.10 (d, J=7.8 Hz, 1H), 7.15-7.20 (m, 1H), 7.29 (t, J=7.4 Hz, 1H), 7.44 (br s, 1H), 7.56-7.68 (m, 3H), 7.92-7.98 (m, 2H).

Step 3: Ethyl 4-{3-[2-chloro-6-(trifluoromethyl)phenoxy]-1H-indazol-1-yl}-3-fluorobenzoate To a stirred suspension of tert butyl nitrite (0.19 mL, 1.625 mmol) and copper (II) chloride (218 mg, 1.625 mmol) in acetonitrile (5 mL) was added a solution of step 2 intermediate (500 mg, 1.083 mmol) in acetonitrile (5 mL) very slowly and heated to 50° C. for 1 hour. The reaction mixture was quenched with 1N HCl (100 mL) and extracted with ethyl acetate (3×100 mL). The combined organic extracts were washed with water (2×100 mL) followed by brine (100 mL). The solution was dried over anhydrous sodium sulfate and concentrated under reduced pressure to yield 500 mg of the title product as brown oil. $^1$H NMR (300 MHz, DMSO-d$_6$) δ 1.33 (t, J=6.6 Hz, 3H), 4.34 (q, J=6.6 Hz, 2H), 7.36 (t, J=7.5 Hz, 1H), 7.49 (br s, 1H), 7.61 (br s, 3H), 7.83 (d, J=7.8 Hz, 1H), 7.90-8.03 (m, 4H).

Step 4: 4-{3-[2-Chloro-6-(trifluoromethyl)phenoxy]-1H-indazol-1-yl}-3-fluorobenzoic acid Method A To a stirred cooled (0° C.) solution of step 3 intermediate (500 mg, 1.049 mmol) in a mixture of THF (6 mL), methanol (4 mL) and water (2 mL) was added lithium hydroxide (175 mg, 4.176 mmol) and the reaction mixture was stirred for 16 hours at RT. The reaction mixture was concentrated and acidified with 1 N HCl to give a thick precipitate. The solid was filtered, dried and purified by silica gel column chromatography to yield 285 mg of the title product as off white solid.

Method B

To a stirred cooled (0° C.) solution of step 3 intermediate (54 mg, 0.112 mmol) in methanol (3 mL) was added 2N aqueous solution of sodium hydroxide (281 µL, 0.563 mmol) and the reaction mixture was stirred for 4 hours at RT. The reaction mixture was concentrated and acidified with 1 N HCl to give a thick precipitate. The precipitate was stirred for 30 minutes and allowed to settle down. The solid was filtered, washed with water, dried at 100° C. for 30 minutes to yield 32 mg of the title product as white solid. $^1$H NMR (300 MHz, CDCl$_3$) δ 7.36 (t, J=7.4 Hz, 1H), 7.49 (br s, 1H), 7.61 (br s, 3H), 7.83-7.90 (m, 4H), 8.01 (d, J=8.4 Hz, 1H), 13.46 (br s, 1H); APCI-MS (m/z) 451 (M+H)$^+$.

Example 8

3-Fluoro-4-{3-[2-(trifluoromethyl)phenoxy]-1H-indazol-1-yl}benzoic acid

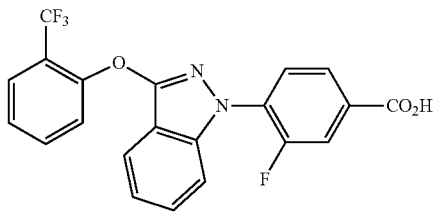 [SMILES: O=C(O)c1ccc(-n2nc(Oc3ccccc3C(F)(F)F)c3ccccc32)c(F)c1]

Step 1: Ethyl 4-{3-[4-amino-2-(trifluoromethyl)phenoxy]-1H-indazol-1-yl}-3-fluorobenzoate The title compound was prepared by the reaction of Intermediate 2 (250 mg, 0.831 mmol) with 1-fluoro-4-nitro-2-(trifluoromethyl)benzene (173 mg, 0.831 mmol) in the presence of sodium hydride (60% w/w) (40 mg, 0.997 mmol) in DMF (5 mL) to give the corresponding nitro intermediate which on palladium catalyzed hydrogenation to yield 200 mg of the product as off white solid. $^1$H NMR (300 MHz, DMSO-d$_6$) δ 1.34 (t, J=6.9 Hz, 3H), 4.36 (q, J=6.6 Hz, 2H), 5.55 (s, 2H), 6.81 (d, J=8.4 Hz, 1H), 6.95 (s, 1H), 7.24-7.27 (m, 2H), 7.48-7.55 (m, 3H), 7.74-7.77 (m, 1H), 7.95 (t, J=10.8 Hz, 2H); APCI-MS (m/z) 460 (M+H)$^+$.

Step 2: Ethyl 3-fluoro-4-{3-[2-(trifluoromethyl)phenoxy]-1H-indazol-1-yl}benzoate The title compound was prepared by the reaction of step 1 intermediate (150 mg, 0.325 mmol) with tert butyl nitrite (0.07 mL, 0.569 mmol) in DMF (6 mL) as per the process described in step 3 of Example 5 to yield 130 mg of the title product as brown oil. $^1$H NMR (300 MHz, DMSO-d$_6$) δ 1.33 (t, J=6.6 Hz, 3H), 4.34 (q, J=6.9 Hz, 2H), 7.30 (t, J=7.5 Hz, 1H), 7.30 (t, J=7.5 Hz, 1H), 7.57-7.59 (m, 4H), 7.70-7.72 (m, 1H), 7.80-7.83 (m, 2H), 7.93-8.00 (m, 2H); APCI-MS (m/z) 445 (M+H)$^+$.

Step 3: 3-Fluoro-4-{3-[2-(trifluoromethyl)phenoxy]-1H-indazol-1-yl}benzoic acid

The title compound was prepared by the hydrolysis of step 2 intermediate (130 mg, 0.291 mmol) using lithium hydroxide (37 mg, 0.873 mmol) in methanol (2 mL) and water (1 mL) as per the process described in step 2 of Example 1 to yield 60 mg of the product as off white solid; $^1$H NMR (300 MHz, DMSO-d$_6$) δ 7.31 (t, J=7.2 Hz, 1H), 7.43 (t, J=7.2 Hz, 1H), 7.54-7.60 (m, 4H), 7.70-7.82 (m, 2H), 7.86 (d, J=7.8 Hz, 1H), 7.95-8.01 (m, 2H), 13.51 (br s, 1H); APCI-MS (m/z) 417 (M+H)$^+$.

Example 9

4-{3-[4-Chloro-2-(trifluoromethyl)phenoxy]-1H-indazol-1-yl}-3-fluorobenzoic acid

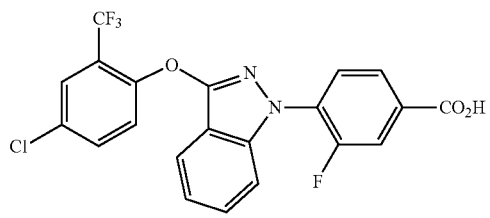 [SMILES: O=C(O)c1ccc(-n2nc(Oc3ccc(Cl)cc3C(F)(F)F)c3ccccc32)c(F)c1]

Step 1: Ethyl 4-{3-[4-chloro-2-(trifluoromethyl)phenoxy]-1H-indazol-1-yl}-3-fluorobenzoate The reaction of ethyl 4-{3-[4-amino-2-(trifluoromethyl)phenoxy]-1H-indazol-1-yl}-3-fluorobenzoate (60 mg, 0.130 mmol) with tert butyl nitrite (0.23 mL, 1.461 mmol) and copper (II) chloride (26 mg, 0.195 mmol) in acetonitrile (6 mL) as per the process described in Step 3 of Example 7 yielded 45 mg of the product as off white solid. APCI-MS (m/z) 479 (M+H)$^+$.

Step 2: 4-{3-[4-Chloro-2-(trifluoromethyl)phenoxy]-1H-indazol-1-yl}-3-fluorobenzoic acid The title compound was prepared by the hydrolysis of step 1 intermediate (45 mg, 0.0939 mmol) using lithium hydroxide (15 mg, 0.375 mmol) in THF (2 mL), methanol (2 mL) and water (1 mL) as per the process described in step 2 of Example 1 to yield 10 mg of the title product as off white solid; $^1$H NMR (300 MHz, CDCl$_3$) δ 7.33-7.45 (m, 1H), 7.52-7.57 (m, 3H), 7.71 (br s, 3H), 8.02-8.06 (m, 2H), 13.35 (br s, 1H); APCI-MS (m/z) 451 (M+H)$^+$.

Example 10

4-{3-[2-Chloro-6-(difluoromethyl)phenoxy]-1H-indazol-1-yl}-3-fluorobenzoic acid

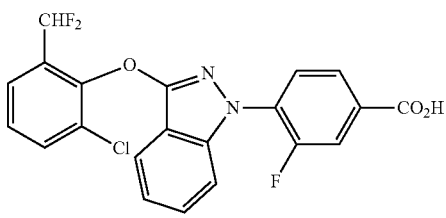 [SMILES: O=C(O)c1ccc(-n2nc(Oc3c(Cl)cccc3C(F)F)c3ccccc32)c(F)c1]

Step 1: Ethyl 4-{3-[2-amino-6-(difluoromethyl)phenoxy]-1H-indazol-1-yl}-3-fluorobenzoate The title compound was prepared from the reaction of Intermediate 2 (500 mg, 1.663 mmol) with 1-(difluoromethyl)-2-fluoro-3-nitrobenzene (302 mg, 1.579 mmol) in the presence of sodium hydride (60% w/w) (79 mg, 1.995 mmol) in DMF (5 mL) to give corresponding nitro derivative which on palladium catalyzed hydrogenation yielded 430 mg of the product as brown oil. $^1$H NMR (300 MHz, DMSO-$d_6$) δ 1.34 (t, J=7.5 Hz, 3H), 4.36 (q, J=7.2 Hz, 2H), 5.31 (s, 2H), 6.81 (d, J=8.4 Hz, 1H), 7.00 (t, J=7.8 Hz, 2H), 7.15 (t, J=7.8 Hz, 1H), 7.28 (t, J=7.2 Hz, 1H), 7.42-7.44 (m, 1H), 7.56 (t, J=7.5 Hz, 1H), 7.64 (t, J=8.4 Hz, 1H), 7.72 (d, J=7.8 Hz, 1H), 7.94 (t, J=8.7 Hz, 2H); APCI-MS (m/z) 442 (M+H)$^+$.

Step 2: Ethyl 4-{3-[2-chloro-6-(trifluoromethyl)phenoxy]-1H-indazol-1-yl}-3-fluorobenzoate The reaction of step 1 intermediate (430 mg, 0.974 mmol) with tert butyl nitrite (0.17 ml, 1.461 mmol) and copper (II) chloride (196 mg, 1.461 mmol) in acetonitrile (15 mL) as per the process described in step 3 of Example 7 yielded 365 mg of the title product as yellow semi-solid. $^1$H NMR (300 MHz, DMSO-$d_6$) δ 1.33 (t, J=6.9 Hz, 3H), 4.36 (q, J=6.9 Hz, 2H), 7.26 (br s, 1H), 7.36 (t, J=7.5 Hz, 1H), 7.48-7.64 (m, 4H), 7.75 (d, J=6.9 Hz, 1H), 7.82-7.97 (m, 4H); APCI-MS (m/z) 461 (M+H)$^+$.

Step 3: 4-{3-[2-Chloro-6-(trifluoromethyl)phenoxy]-1H-indazol-1-yl}-3-fluorobenzoic acid The title compound was prepared by the hydrolysis of step 2 intermediate (365 mg, 0.792 mmol) using lithium hydroxide (132 mg, 3.168 mmol) in methanol (2 mL) and water (1 mL) as per the process described in step 2 of Example 1 to yield 70 mg of the product as off white solid; $^1$H NMR (300 MHz, DMSO-$d_6$) δ 7.25 (t, J=54 Hz, 1H), 7.35 (br s, 1H), 7.48 (br s, 1H), 7.53-7.60 (m, 3H), 7.38 (d, J=6.9 Hz, 1H), 7.83-7.93 (m, 4H), 13.45 (br s, 1H); APCI-MS (m/z) 433 (M+H)$^+$.

Example 11

4-[3-(2,6-Dichlorophenoxy)-7-fluoro-1H-indazol-1-yl]-3-fluorobenzoic acid

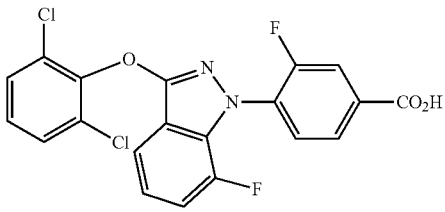 [SMILES: O=C(O)c1ccc(-n2nc(Oc3c(Cl)cccc3Cl)c3cccc(F)c32)c(F)c1]

Step 1: Ethyl 4-[3-(2,6-dichloro-4-nitrophenoxy)-7-fluoro-1H-indazol-1-yl]-3-fluorobenzoate To a well stirred solution of Intermediate 3 (108 mg, 0.339 mmol) in DMF (8 mL) was added sodium hydride (60% w/w) (16 mg, 0.406 mmol) in small portions and the mixture was stirred at RT for 30 minutes. To the mixture was slowly added a solution of 1,3-dichloro-2-fluoro-5-nitrobenzene (64 mg, 0.305 mmol) in DMF (3 mL) and further stirred at RT for 16 h. The reaction mixture was quenched with aqueous solution of ammonium chloride (50 mL) and was extracted with ethyl acetate (2×100 mL). The combined organic layers were washed with water (2×50 mL), brine (50 mL), dried (Na$_2$SO$_4$) and concentrated under reduced pressure. The residue thus obtained was purified by silica gel column chromatography to yield 123 mg of the title product as light yellow solid; $^1$H NMR (300 MHz, DMSO-$d_6$) δ 1.33 (t, J=7.5 Hz, 3H), 4.34 (q, J=6.9 Hz, 2H), 7.35 (br s, 1H), 7.45-7.60 (m, 1H), 7.72 (t, J=8.4 Hz, 1H), 7.80 (d, J=7.8 Hz, 1H), 7.85-7.95 (m, 2H), 8.57 (s, 2H).

Step 2: Ethyl 4-[3-(4-amino-2,6-dichlorophenoxy)-7-fluoro-1H-indazol-1-yl]-3-fluorobenzoate To a stirred solution of Step 1 intermediate (116 mg, 0.228 mmol) in a mixture of ethanol (5 mL) and water (1 mL) was added (122 mg, 2.282 mmol) and the reaction was heated to 90° C. Iron powder (38 mg, 0.684 mmol) was added to the reaction mixture at 90° C. and the reaction was further stirred at same temperature for 2 h. The reaction mixture was filtered and solvents were distilled out under reduced pressure. The sticky residue obtained was diluted with ethyl acetate (250 mL). The layers were separated and the organic layer was washed with aqueous solution of sodium bicarbonate (50 mL) followed by brine (50 mL). The solvent was distilled off completely under reduced pressure to yield 112 mg of the title product as off white solid. $^1$H NMR (300 MHz, DMSO-$d_6$) δ 1.33 (t, J=6.9 Hz, 3H), 4.35 (q, J=6.9 Hz, 2H), 5.71 (s, 2H), 7.27-7.40 (m, 1H), 7.41-7.47 (m, 1H), 7.59 (d, J=7.8 Hz, 1H), 7.72 (t, J=7.4 Hz, 1H), 7.90-7.92 (m, 2H).

Step 3: Ethyl 4-[3-(2,6-dichlorophenoxy)-7-fluoro-1H-indazol-1-yl]-3-fluorobenzoate To a stirred solution of tert butyl nitrite (0.05 ml, 0.468 mmol) in DMF (6 mL) was added a solution of step 2 intermediate (112 mg, 0.234 mmol) in DMF (6 mL) at 55-60° C. over a period of 20 min. The reaction mixture was stirred at 55° C. for 1 hour. The reaction mixture was cooled to RT and quenched with 1N HCl (10 mL). The solution was poured into water (20 mL) and extracted with ethyl acetate (3×30 mL). The combined organic layers were washed with brine (30 mL) and dried over anhydrous sodium sulfate. The solvents were removed under reduced pressure and residue thus obtained was purified by silica gel column chromatography to yield 88 mg of the title product as light yellow oil. $^1$H NMR (300 MHz, DMSO-$d_6$) δ 1.33 (t, J=7.5 Hz, 3H), 4.34 (q, J=6.9 Hz, 2H), 7.32-7.49 (m, 3H), 7.65-7.74 (m, 4H), 7.88-7.94 (m, 2H).

Step 4: 4-[3-(2,6-Dichlorophenoxy)-7-fluoro-1H-indazol-1-yl]-3-fluorobenzoic acid To a stirred and cooled (0° C.) solution of step 3 intermediate (81 mg, 0.175 mmol) in THF (3 mL), methanol (2 mL) and water (1 mL) was added lithium hydroxide (22 mg, 0.525 mmol) and the reaction mixture was stirred at RT for 18 hours. The reaction mixture was concentrated under reduced pressure and the residue obtained was acidified with 1 N HCl to obtain a thick precipitate. The solid obtained was filtered, washed with diethyl ether (10 mL) and dried to obtain 43 mg of the product as off white solid; $^1$H NMR (300 MHz, DMSO-$d_6$) δ 7.31-7.37 (m, 1H), 7.40-7.51 (m, 2H), 7.66 (d, J=7.8 Hz, 3H), 7.72 (d, J=8.1 Hz, 1H), 7.87 (d, J=9.0 Hz, 2H), 13.50 (br s, 1H); APCI-MS (m/z) 435 (M+H)$^+$.

Example 12

4-{3-[2-Chloro-6-(difluoromethyl)phenoxy]-7-fluoro-1H-indazol-1-yl}-3-fluorobenzoic acid

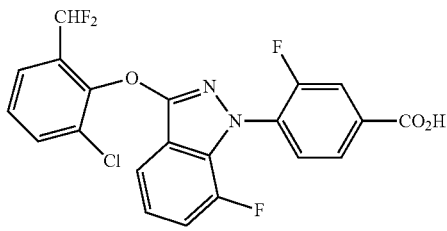 [SMILES: O=C(O)c1ccc(-n2nc(Oc3c(Cl)cccc3C(F)F)c3cccc(F)c32)c(F)c1]

Step 1: Ethyl 4-{3-[2-amino-6-(difluoromethyl)phenoxy]-7-fluoro-1H-indazol-1-yl}-3-fluorobenzoate The title compound was prepared by the reaction of Intermediate 3 (196 mg, 0.616 mmol) with 1-(difluoromethyl)-2-fluoro-3-nitrobenzene (118 mg, 0.616 mmol) in the presence of sodium hydride (60% w/w) (29 mg, 0.739 mmol) in DMF (6 mL) to give corresponding nitro intermediate (130 mg, 0.265 mmol) which was reduced by using ammonium chloride (142 mg, 2.65 mmol) and iron powder (45 mg, 0.795 mmol) in a mixture of ethanol (5 mL) and water (1 mL) as per the process described in step 1 and 2 of Example 5 to yield 116 mg of the product as light yellow oil; $^1$H NMR (300 MHz, DMSO-$d_6$) δ 1.35 (t, J=6.6 Hz, 3H), 4.34 (q, J=6.9 Hz, 2H), 6.79 (s, 2H), 6.80 (d, J=7.2 Hz, 1H), 6.81-6.96 (m, 1H), 7.10-7.19 (m, 1H), 7.24-7.28 (m, 1H), 7.36-7.45 (m, 1H), 7.55-7.90 (m, 2H), 7.91 (d, J=9.3 Hz, 2H), 8.53 (d, J=9.3 Hz, 1H); APCI-MS (m/z) 439 (M)$^+$.

Step 2: Ethyl 4-{3-[2-chloro-6-(difluoromethyl)phenoxy]-7-fluoro-1H-indazol-1-yl}-3-fluorobenzoate The title compound was prepared by the reaction of step 1 intermediate (110 mg, 0.239 mmol) with tert butyl nitrite (0.057 ml, 0.478 mmol) and copper (II) chloride (65 mg, 0.478 mmol) in acetonitrile (3 mL) as per the process described in step 3 of Example 7 to yield 106 mg of the product as brown solid; $^1$H NMR (300 MHz, DMSO-$d_6$) δ 1.33 (t, J=7.2 Hz, 3H), 4.35 (q, J=6.9 Hz, 2H), 7.31-7.32 (m, 1H), 7.44-7.56 (m, 3H), 7.67-7.74 (m, 3H), 7.86-7.93 (m, 3H); APCI-MS (m/z) 458 (M)$^+$.

Step 3: 4-{3-[2-Chloro-6-(difluoromethyl)phenoxy]-7-fluoro-1H-indazol-1-yl}-3-fluorobenzoic acid The title compound was prepared by the hydrolysis of Step 2 intermediate (101 mg, 0.210 mmol) using lithium hydroxide (27 mg, 0.632 mmol) in THF (3 mL), methanol (2 mL) and water (1 mL) as per the process described in step 2 of Example 1 to yield 41 mg of the product as light grey solid; $^1$H NMR (300 MHz, DMSO-$d_6$) δ 7.30-7.35 (m, 2H), 7.43-7.56 (m, 2H), 7.62-7.74 (m, 3H), 7.84-7.89 (m, 3H); APCI-MS (m/z) 450 (M)$^+$.

Example 13

4-[3-(2-Chloro-6-cyclopropylphenoxy)-1H-indazol-1-yl]-3-fluorobenzoic acid

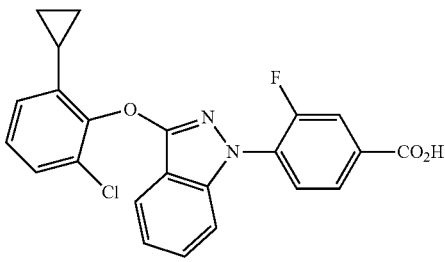 [SMILES: O=C(O)c1ccc(-n2nc(Oc3c(Cl)cccc3C3CC3)c3ccccc32)c(F)c1]

Step 1: Ethyl 4-[3-(4-amino-2-chloro-6-cyclopropylphenoxy)-1H-indazol-1-yl]-3-fluorobenzoate The title compound was prepared by the reaction of Intermediate 2 (100 mg, 0.333 mmol) with 1,2-dichloro-3-cyclopropyl-5-nitrobenzene (76 mg, 0.333 mmol) in the presence of sodium hydride (60% w/w) (16 mg, 0.399 mmol) in DMSO (3 ml) to give corresponding nitro compound (304 mg, 0.591 mmol) which was reduced by using ammonium chloride (316 mg, 5.91 mmol) and iron powder (100 mg, 1.773 mmol) in ethanol (5 mL) and water (1 mL) as per the process described in step 1 and 2 of Example 5 to yield 281 mg of the product as off white solid; $^1$H NMR (300 MHz, DMSO-$d_6$) δ 0.54-0.55 (m, 2H), 0.75-0.77 (m, 2H), 1.34 (t, J=6.9 Hz, 3H), 1.86-1.90 (m, 1H), 4.34 (q, J=6.9 Hz, 2H), 5.27 (s, 2H), 6.14 (d, J=1.8 Hz, 1H), 6.53 (d, J=2.4 Hz, 1H), 7.27 (t, J=6.9 Hz, 1H), 7.43-6.46 (m, 1H), 7.52-7.55 (m, 1H), 7.263-7.69 (m, 2H), 7.92-7.97 (m, 2H); APCI-MS (m/z) 466 (M+H)$^+$.

Step 2: Ethyl 4-[3-(2-chloro-6-cyclopropylphenoxy)-1H-indazol-1-yl]-3-fluorobenzoate The title compound was synthesized by de-amination reaction of step 1 intermediate (273 mg, 0.585 mmol) with tert butyl nitrite (0.14 ml, 1.17 mmol) in DMF (5 mL) as per the process described in step 3 of Example 5 to yield 211 mg of the product as brown oil; $^1$H NMR (300 MHz, DMSO-$d_6$)

δ 0.67-0.69 (m, 2H), 0.80-0.83 (m, 2H), 1.31 (t, J=6.9 Hz, 3H), 1.96-2.01 (m, 1H), 4.34 (q, J=6.9 Hz, 2H), 7.02 (d, J=8.1 Hz, 1H), 7.21-7.33 (m, 2H), 7.39-7.44 (m, 2H), 7.54-7.64 (m, 2H), 7.76 (d, J=7.8 Hz, 1H), 7.89-7.95 (m, 2H); APCI-MS (m/z) 451 (M+H)+.

Step 3: 4-[3-(2-Chloro-6-cyclopropylphenoxy)-1H-indazol-1-yl]-3-fluorobenzoic acid The title compound was prepared by the hydrolysis of Step 2 intermediate (203 mg, 0.45 mmol) using lithium hydroxide (76 mg, 1.80 mmol) in methanol (2 mL) and water (1 mL) as per the process described in step 2 of Example 1 to yield 151 mg of the product as light yellow solid; $^1$H NMR (300 MHz, DMSO-$d_6$) δ 0.69-0.70 (m, 2H), 0.81-0.84 (m, 2H), 1.96-2.02 (m, 1H), 7.02 (d, J=8.1 Hz, 1H), 7.22-7.34 (m, 2H), 7.40-7.46 (m, 2H), 7.55-7.63 (m, 2H), 7.76 (d, J=7.8 Hz, 1H), 7.89-7.93 (m, 2H), 13.4 (br s, 1H); APCI-MS (m/z) 423 (M+H)+.

Example 14

4-[3-(2-Chloro-6-cyclopropylphenoxy)-7-fluoro-1H-indazol-1-yl]-3-fluorobenzoic acid

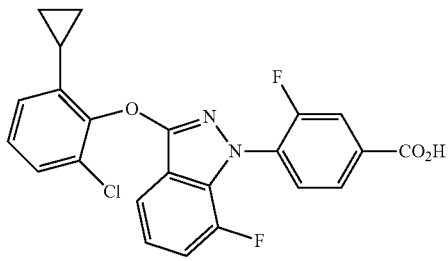 [SMILES: O=C(O)c1ccc(-n2nc(Oc3c(Cl)cccc3C3CC3)c3cccc(F)c32)c(F)c1]

Step 1: Ethyl 4-[3-(4-amino-2-chloro-6-cyclopropylphenoxy)-7-fluoro-1H-indazol-1-yl]-3-fluorobenzoate The title compound was prepared by the reaction of Intermediate 3 (150 mg, 0.470 mmol) with 1,2-dichloro-3-cyclopropyl-5-nitrobenzene (110 mg, 0.470 mmol) in the presence of sodium hydride (60% w/w) (22.5 mg, 0.564 mmol) in DMSO (5 mL) to give corresponding nitro intermediate (358 mg, 0.696 mmol) which on reduction using ammonium chloride (372 mg, 6.96 mmol) and iron powder (117 mg, 2.08 mmol) in ethanol (4 mL) and water (1 mL) as per the process described in step 1 and 2 of Example 5 yielded 318 mg of the product as light yellow solid; $^1$H NMR (300 MHz, DMSO-$d_6$) δ 0.50-0.51 (m, 2H), 0.72-0.74 (m, 2H), 1.29 (t, J=7.5 Hz, 3H), 1.82-1.85 (m, 1H), 4.34 (q, J=7.2 Hz, 2H), 5.24 (s, 2H), 6.13 (d, J=1.8 Hz, 1H), 6.50 (d, J=2.4 Hz, 1H), 7.20-7.24 (m, 1H), 7.35-6.41 (m, 1H), 7.46 (d, J=7.8 Hz, 1H), 7.69 (t, J=7.8 Hz, 1H), 7.89 (d, J=9.0 Hz, 2H); APCI-MS (m/z) 484 (M+H)+.

Step 2: Ethyl 4-[3-(2-chloro-6-cyclopropylphenoxy)-7-fluoro-1H-indazol-1-yl]-3-fluorobenzoate The title compound was synthesized by de-amination reaction of step 1 intermediate (312 mg, 0.644 mmol) with tert butyl nitrite (0.16 mL, 1.289 mmol) in DMF (5 mL) as per the process described in step 3 of Example 5 to yield 219 mg of product as light yellow oil; $^1$H NMR (300 MHz, DMSO-$d_6$) δ 0.62-0.69 (m, 2H), 0.79-0.83 (m, 2H), 1.33 (t, J=6.9 Hz, 3H), 1.97-2.01 (m, 1H), 4.35 (q, J=7.2 Hz, 2H), 7.02 (d, J=8.1 Hz, 1H), 7.22-7.29 (m, 2H), 7.40-7.48 (m, 2H), 7.64-7.73 (m, 2H), 7.89 (d, J=10.8 Hz, 2H); APCI-MS (m/z) 469 (M+H)+.

Step 3: 4-[3-(2-Chloro-6-cyclopropylphenoxy)-7-fluoro-1H-indazol-1-yl]-3-fluorobenzoic acid The title compound was prepared by the hydrolysis of step 2 intermediate (211 mg, 0.45 mmol) using lithium hydroxide (76 mg, 1.80 mmol) in methanol (2 mL) and water (1 mL) as per the process described in step 2 of Example 1 to yield 153 mg of the product as off white solid; $^1$H NMR (300 MHz, DMSO-$d_6$) δ 0.67-0.69 (m, 2H), 0.81-0.84 (m, 2H), 1.96-2.01 (m, 1H), 7.02 (d, J=7.8 Hz, 1H), 7.22-7.31 (m, 2H), 7.40-7.47 (m, 2H), 7.64-7.69 (m, 2H), 7.86-7.89 (m, 2H) 13.5 (br s, 1H); APCI-MS (m/z) 441 (M+H)+.

Example 15

4-{3-[(2-Fluorophenyl)carbonyl]-1H-indol-1-yl}benzoic acid

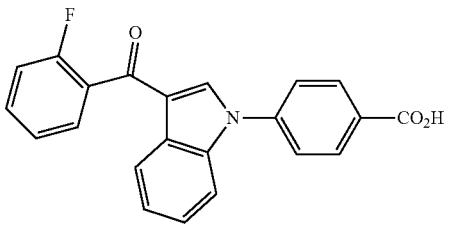 [SMILES: O=C(O)c1ccc(-n2cc(C(=O)c3ccccc3F)c3ccccc32)cc1]

Step 1: Ethyl 4-{3-[(2-fluorophenyl)carbonyl]-1H-indol-1-yl}benzoate

To a stirred suspension of aluminum chloride (301 mg, 2.261 mmol) in DCM (7 mL) was added 2-fluorobenzoyl chloride (0.14 mL, 1.130 mmol) and the mixture was stirred at RT for 15 min. A solution of Intermediate 4 (100 mg, 0.377 mmol) in DCM (7 mL) was added drop wise to the reaction mixture was and it was stirred for 2 h at RT. Reaction mixture was diluted with water (50 mL) and the layers were separated. The aqueous layer was extracted with ethyl acetate (2×100 mL). The combined organic extracts were washed with aqueous sodium bicarbonate (100 mL), water (50 mL), brine (25 mL) and dried ($Na_2SO_4$). The solvent was distilled under reduced pressure and the residue obtained was purified by silica gel column chromatography to yield 45 mg of the title product as off white solid. $^1$H NMR (300 MHz, DMSO-$d_6$) δ 1.34 (t, J=7.2 Hz, 3H), 4.35 (q, J=6.9 Hz, 2H), 7.35-7.40 (m, 4H), 7.363-7.69 (m, 3H), 7.83 (d, J=7.8 Hz, 2H), 8.14 (d, J=6.9 Hz, 3H), 8.19 (s, 1H).

Step 2: 4-{3-[(2-Fluorophenyl)carbonyl]-1H-indol-1-yl}benzoic acid

The title compound was prepared by the hydrolysis of Step 1 intermediate (40 mg, 0.103 mmol) using lithium hydroxide (17 mg, 0.413 mmol) in methanol (2 mL) and water (1 mL) as per the process described in step 2 of Example 1 to yield 30 mg of the product as off white solid; ¹H NMR (300 MHz, DMSO-d₆) δ 7.34-7.39 (m, 4H), 7.62-7.68 (m, 3H), 7.80 (d, J=8.4 Hz, 2H), 8.12 (d, J=8.4 Hz, 2H), 8.15 (s, 1H), 8.34 (br s, 1H), 13.22 (br s, 1H); APCI-MS (m/z) 360 (M+H)⁺.

Example 16

4-{3-[(2,6-Dichlorophenyl)carbonyl]-1H-indol-1-yl}benzoic acid

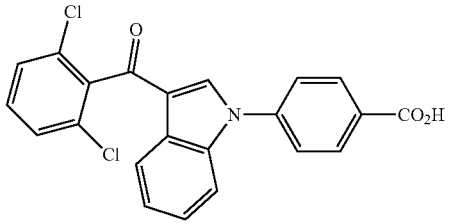 [SMILES: O=C(O)c1ccc(-n2cc(C(=O)c3c(Cl)cccc3Cl)c3ccccc32)cc1]

Step 1: Ethyl 4-{3-[(2,6-dichlorophenyl)carbonyl]-1H-indol-1-yl}benzoate

The title compound was prepared by reaction of Intermediate 4 (100 mg, 0.377 mmol) with 2,6-dichlorobenzoyl chloride {prepared in situ from 2,6-dichlorobenzoic acid (216 mg, 1.130 mmol) and oxalyl chloride (286 mg, 2.261 mmol)} in the presence of aluminium trichloride (302 mg, 2.261 mmol) in DCM (5 mL) as per the process described in step 1 of Example 15 to yield to give 65 mg of the product as white solid. ¹H NMR (300 MHz, DMSO-d₆) δ 1.34 (t, J=7.2 Hz, 3H), 4.35 (q, J=7.2 Hz, 2H), 7.43 (br s, 2H), 7.53-7.65 (m, 4H), 7.80 (d, J=7.8 Hz, 2H), 8.13 (d, J=8.1 Hz, 2H), 8.28 (br s, 1H).

Step 2: 4-{3-[(2,6-Dichlorophenyl)carbonyl]-1H-indol-1-yl}benzoic acid

The title compound was prepared by the hydrolysis of step 1 intermediate (60 mg, 0.1369 mmol) using lithium hydroxide (28 mg, 0.6845 mmol) in THF (5 mL) and water (1 mL) as per the process described in step 2 of Example 1 to yield 35 mg of the product as off white solid. ¹H NMR (300 MHz, DMSO-d₆) δ 7.42 (br s, 3H), 7.54-7.65 (m, 4H), 7.77 (d, J=7.8 Hz, 2H), 8.12 (d, J=7.8 Hz, 2H), 8.27 (br s, 1H), 13.22 (br s, 1H); APCI-MS (m/z) 410 (M)⁺.

Example 17

4-{3-[(2-Chlorophenyl)carbonyl]-1H-indol-1-yl}benzoic acid

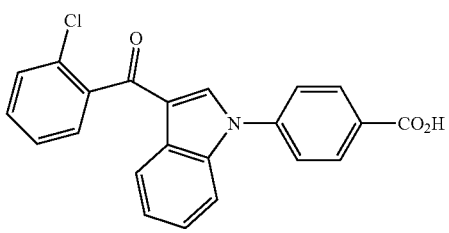 [SMILES: O=C(O)c1ccc(-n2cc(C(=O)c3ccccc3Cl)c3ccccc32)cc1]

Step 1: Ethyl 4-{3-[(2-chlorophenyl)carbonyl]-1H-indol-1-yl}benzoate

The title compound was prepared by reaction of Intermediate 4 (100 mg, 0.377 mmol) with 2-chlorobenzoyl chloride {prepared in situ from 2-chlorobenzoic acid (177 mg, 1.130 mmol) and oxalyl chloride (0.2 mL, 2.261 mmol)} in the presence of aluminium trichloride (300 mg, 2.261 mmol) in DCM (5 mL) as per the process described in step 1 of Example 15 to give 75 mg of the product as off white solid. ¹H NMR (300 MHz, DMSO-d₆) δ 1.32 (t, J=7.2 Hz, 3H), 4.33 (q, J=7.2 Hz, 2H), 7.40-7.49 (m, 3H), 7.50-7.62 (m, 4H), 7.80 (d, J=8.1 Hz, 2H), 8.01 (s, 1H), 8.12 (d, J=8.1 Hz, 2H), 8.28 (br s, 1H); APCI-MS (m/z) 404 (M+H)⁺.

Step 2: 4-{3-[(2-Chlorophenyl)carbonyl]-1H-indol-1-yl}benzoic acid

The title compound was prepared by the hydrolysis of the step 1 intermediate (70 mg, 0.1733 mmol) using lithium hydroxide (29 mg, 0.6933 mmol) in THF (3 mL) and water (1 mL) as per the process described in step 2 of Example 1 to yield 50 mg of the product as off white solid. ¹H NMR (300 MHz, DMSO-d₆) δ 7.42-7.49 (m, 4H), 7.54-7.60 (m, 3H), 7.77 (d, J=7.8 Hz, 2H), 8.01 (s, 1H), 8.11 (d, J=7.8 Hz, 2H), 8.28 (br s, 1H), 13.34 (br s, 1H); APCI-MS (m/z) 376 (M+H)⁺.

Example 18

4-{3-[(2,6-Difluorophenyl)carbonyl]-1H-indol-1-yl}benzoic acid

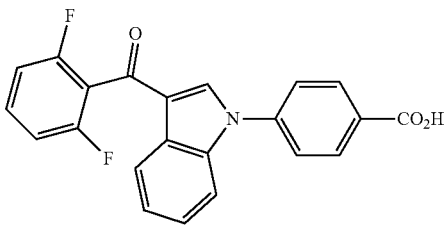 [SMILES: O=C(O)c1ccc(-n2cc(C(=O)c3c(F)cccc3F)c3ccccc32)cc1]

Step 1: Ethyl 4-{3-[(2,6-difluorophenyl)carbonyl]-1H-indol-1-yl}benzoate

The title compound was prepared by acylation of Intermediate 4 (100 mg, 0.377 mmol) with 2,6-difluorobenzoyl chloride (0.14 mL, 1.130 mmol) in the presence of aluminium trichloride (302 mg, 2.261 mmol) in DCM (5 mL) as per the process described in step 1 of Example 15 to obtain 75 mg of the product as off white solid. ¹H NMR (300 MHz, DMSO-d₆) δ 1.34 (t, J=7.2 Hz, 3H), 4.33 (q, J=7.2 Hz, 2H), 7.26 (t, J=7.8 Hz, 2H), 7.44 (br s, 2H), 7.59-7.66 (m, 2H), 7.82 (d, J=8.1 Hz, 2H), 8.13 (d, J=8.4 Hz, 2H), 8.33 (br s, 2H).

Step 2: 4-{3-[(2,6-Difluorophenyl)carbonyl]-1H-indol-1-yl}benzoic acid

The title compound was prepared by the hydrolysis reaction of step 1 intermediate (70 mg, 0.1726 mmol) using lithium hydroxide (28 mg, 0.6906 mmol) in THF (4 mL) and water (1 mL) as per the process described in step 2 of Example 1 to yield 50 mg of the product as off white solid. ¹H NMR (300 MHz, DMSO-d₆) δ 7.21 (d, J=7.8 Hz, 2H), 7.44 (br s, 2H), 7.60-7.66 (m, 3H), 7.79 (d, J=8.1 Hz, 2H), 8.11 (d, J=7.8 Hz, 2H), 8.35 (br s, 1H) 13.44 (br s, 1H); APCI-MS (m/z) 378 (M+H)⁺.

Example 19

4-{3-[(2,6-Dichlorophenyl)carbonyl]-1H-indol-1-yl}-3-fluorobenzoic acid

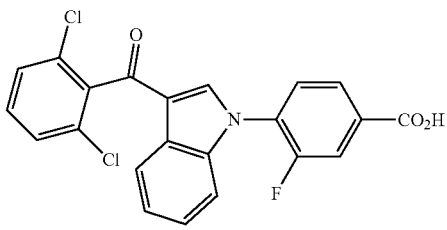 [SMILES: O=C(O)c1ccc(-n2cc(C(=O)c3c(Cl)cccc3Cl)c3ccccc32)c(F)c1]

Step 1: Ethyl 4-{3-[(2,6-dichlorophenyl)carbonyl]-1H-indol-1-yl}-3-fluorobenzoate To a stirred suspension of aluminum chloride (424 mg, 3.176 mmol) in DCM (5 mL) was added 2,6-dichlorobenzoyl chloride {prepared in situ from 2,6-dichlorobenzoic acid (304 mg, 1.588 mmol) and oxalyl chloride (403 mg, 3.176 mmol)} and the mixture was stirred at RT for 15 min. A solution of Intermediate 5 (150 mg, 0.529 mmol) in DCM (5 mL) was added drop wise to the reaction mixture was and it was stirred for 2 h at RT. Reaction mixture was diluted with water (50 mL) and the layers were separated. The aqueous layer was extracted with ethyl acetate (2×100 mL). The combined organic extracts were washed with aqueous sodium bicarbonate (100 mL), water (50 mL), brine (25 mL) and dried (Na₂SO₄). The solvent was distilled under reduced pressure and the residue obtained was purified by silica gel column chromatography to yield 90 mg of the title product as off white solid. ¹H NMR (300 MHz, DMSO-d₆) δ 1.34 (t, J=6.9 Hz, 3H), 4.37 (q, J=6.9 Hz, 2H), 7.39 (br s, 3H), 7.54-7.62 (m, 3H), 7.86-8.01 (m, 3H), 8.23 (br s, 2H); APCI-MS (m/z) 456 (M+H)⁺.

Step 2: 4-{3-[(2,6-Dichlorophenyl)carbonyl]-1H-indol-1-yl}-3-fluorobenzoic acid

To a stirred and cooled (0° C.) solution of Step 1 intermediate (80 mg, 0.1753 mmol) in a mixture of THF (3 mL) and water (1 mL) was added lithium hydroxide (29 mg, 0.7014 mmol). The reaction mixture was stirred at RT for 7 h. The solvents were distilled out under reduced pressure to afford the sticky residue which was diluted with water and acidified with 1N HCl. The precipitate thus obtained was filtered and washed with water. The solid dried well to yield 60 mg of the title product as off white solid. ¹H NMR (300 MHz, DMSO-d₆) δ 7.39 (br s, 3H), 7.54-7.59 (m, 3H), 7.95 (d, J=9.3 Hz, 2H), 8.23 (s, 2H), 13.59 (br s, 1H); APCI-MS (m/z) 428 (M)⁺.

Example 20

4-{3-[(2-Chlorophenyl)carbonyl]-1H-indol-1-yl}-3-fluorobenzoic acid

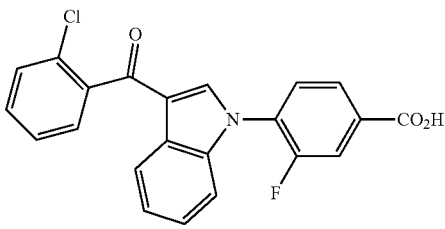 [SMILES: O=C(O)c1ccc(-n2cc(C(=O)c3ccccc3Cl)c3ccccc32)c(F)c1]

Step 1: Ethyl 4-{3-[(2-chlorophenyl)carbonyl]-1H-indol-1-yl}-3-fluorobenzoate

The title compound was prepared by coupling Intermediate 5 (100 mg, 0.352 mmol) with 2-chlorobenzoyl chloride {prepared in situ from 2-chlorobenzoic acid (165 mg, 1.058 mmol) and oxalyl chloride (0.2 mL, 2.117 mmol)} in the presence of aluminium trichloride (282 mg, 2.117 mmol) in DCM (5 mL) as per the process described in step 1 of Example 15 to give 75 mg of the product as off white solid. ¹H NMR (300 MHz, DMSO-d₆) δ 1.34 (t, J=6.9 Hz, 3H), 4.37 (q, J=6.9 Hz, 2H), 7.39 (br s, 3H), 7.47-7.61 (br s, 4H), 7.88 (t, J=7.2 Hz, 1H), 7.90-8.02 (m, 3H), 8.28 (br s, 1H); APCI-MS (m/z) 422 (M+H)⁺.

Step 2: 4-{3-[(2-Chlorophenyl)carbonyl]-1H-indol-1-yl}-3-fluorobenzoic acid

The title compound was prepared by the hydrolysis of step 1 intermediate (70 mg, 0.1659 mmol) using lithium hydroxide (27 mg, 0.6637 mmol) in THF (3 mL) and water (2 mL) as per the process described in step 2 of Example 1 to yield 62 mg of the product as off white solid. ¹H NMR (300 MHz, DMSO-d₆) δ 7.38 (br s, 3H), 7.49 (br s, 1H), 7.47-7.61 (br s, 3H), 7.84 (t, J=7.2 Hz, 1H), 7.92-7.98 (m, 2H), 8.02 (s, 1H), 8.30 (br s, 1H), 13.21 (br s, 1H); APCI-MS (m/z) 394 (M+H)⁺.

Example 21

4-{3-[2-Chloro-6-(trifluoromethyl)benzoyl]-1H-indol-1-yl}-3-fluorobenzoic acid

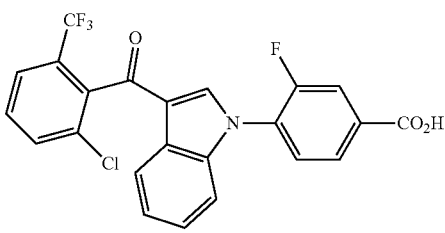 [SMILES: O=C(O)c1ccc(-n2cc(C(=O)c3c(Cl)cccc3C(F)(F)F)c3ccccc32)c(F)c1]

Step 1: Ethyl 4-(3-{[2-chloro-6-(trifluoromethyl)phenyl]carbonyl}-1H-indol-1-yl)-3-fluorobenzoate A mixture of Intermediate 6 (150 mg, 0.463 mmol), ethyl 3-fluoro-4-iodobenzoate (163 mg, 0.556 mmol), potassium carbonate (256 mg, 1.853 mmol), L-proline (21 mg, 0.185 mmol) and copper iodide (17 mg, 0.092 mmol) in DMSO (5 mL) was heated to 110° C. for 16 hours. The reaction mixture was cooled to RT and diluted with water (20 mL). The aqueous mixture was extracted with ethyl acetate (3×20 mL). The combined organic extracts were washed with brine (20 mL) and dried over anhydrous sodium sulphate. The solvent was removed under reduced pressure and residue thus obtained was purified by silica gel column chromatography to yield 30 mg of the title product as off white solid. APCI-MS (m/z) 490 (M+H)$^+$.

Step 2: 4-{3-[2-Chloro-6-(trifluoromethyl)benzoyl]-1H-indol-1-yl}-3-fluoro benzoic acid The title compound was prepared by the hydrolysis of Step 1 intermediate (25 mg, 0.051 mmol) using lithium hydroxide (8 mg, 0.204 mmol) in methanol (2 mL) and water (1 mL) as per the process described in step 2 of Example 1 to yield 19 mg of the product as off white solid. $^1$H NMR (300 MHz, DMSO-d$_6$) δ 7.39 (br s, 3H), 7.73-7.78 (m, 2H), 7.82-7.92 (m, 4H), 8.18 (br s, 1H), 8.21 (br s, 1H), 13.57 (br s, 1H); APCI-MS (m/z) 462 (M+H)$^+$.

Example 22

4-[3-(2,6-Dichlorobenzoyl)-4-fluoro-1H-indol-1-yl]-3-fluorobenzoic acid

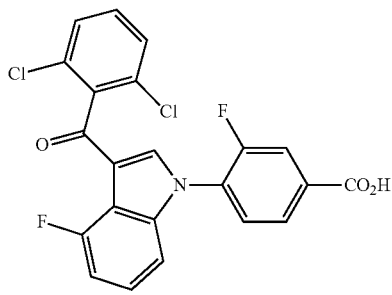 [SMILES: O=C(O)c1ccc(-n2cc(C(=O)c3c(Cl)cccc3Cl)c3c(F)cccc32)c(F)c1]

Step 1: Ethyl 4-[3-(2,6-dichlorobenzoyl)-4-fluoro-1H-indol-1-yl]-3-fluorobenzoate The title compound was prepared by acylation reaction of Intermediate 7 (300 mg, 0.992 mmol) with 2,6-dichlorobenzoyl chloride (0.43 ml, 2.907 mmol) using aluminium trichloride (797 mg, 5.974 mmol) in DCM (5 mL) as per the process described in step 1 of Example 15 to give 310 mg of the product as off white solid. $^1$H NMR (300 MHz, DMSO-d$_6$) δ 1.34 (t, J=6.9 Hz, 3H), 4.37 (q, J=6.9 Hz, 2H), 7.19 (br s, 2H), 7.38 (br s, 1H), 7.52-7.60 (m, 3H), 7.85-7.90 (m, 1H), 7.91-8.02 (m, 2H), 8.29 (s, 1H); APCI-MS (m/z) 474 (M+H)$^+$.

Step 2: 4-[3-(2,6-Dichlorobenzoyl)-4-fluoro-1H-indol-1-yl]-3-fluorobenzoic acid

The title compound was prepared by the hydrolysis of the step 1 intermediate (300 mg, 0.6325 mmol) using lithium hydroxide (106 mg, 2.530 mmol) in THF (10 mL) and water (2 mL) as per the process described in step 2 of Example 1 to yield 260 mg of the product as off white solid. $^1$H NMR (300 MHz, DMSO-d$_6$) δ 7.18 (d, J=6.3 Hz, 2H), 7.38 (br s, 1H), 7.51-7.59 (m, 3H), 7.84 (t, J=7.2 Hz, 1H), 7.95 (br s, 2H), 8.28 (s, 1H), 13.61 (br s, 1H); APCI-MS (m/z) 446 (M+H)$^+$.

Example 23

4-[3-(2,6-Dichlorobenzoyl)-5-fluoro-1H-indol-1-yl]-3-fluorobenzoic acid

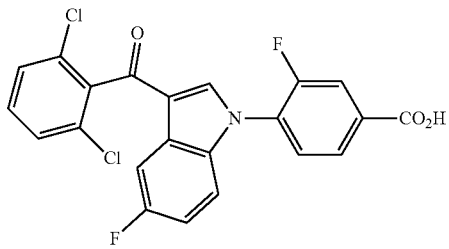 [SMILES: O=C(O)c1ccc(-n2cc(C(=O)c3c(Cl)cccc3Cl)c3cc(F)ccc32)c(F)c1]

Step 1: Ethyl 4-[3-(2,6-dichlorobenzoyl)-5-fluoro-1H-indol-1-yl]-3-fluorobenzoate The title compound was prepared by acylation reaction of Intermediate 8 (200 mg, 0.663 mmol) with 2,6-dichlorobenzoyl chloride (0.28 mL, 1.991 mmol) using aluminium trichloride (531 mg, 3.982 mmol) in DCM (5 mL) as per the process described in step 1 of Example 15 to obtain 155 mg of the product as yellow solid. $^1$H NMR (300 MHz, DMSO-d$_6$) δ 1.34 (t, J=6.9 Hz, 3H), 4.37 (q, J=6.9 Hz, 2H), 7.27 (t, J=6.9 Hz, 1H), 7.44-7.62 (m, 5H), 7.88-8.00 (m, 3H), 8.33 (s, 1H); APCI-MS (m/z) 474 (M+H)$^+$.

Step 2: 4-[3-(2,6-Dichlorobenzoyl)-5-fluoro-1H-indol-1-yl]-3-fluorobenzoic acid

The title compound was prepared by the hydrolysis of step 1 intermediate (150 mg, 0.3162 mmol) using lithium hydroxide (53 mg, 1.265 mmol) in THF (5 mL) and water (2 mL) as per the process described in step 2 of Example 1 to yield 100 mg of the product as off white solid. $^1$H NMR (300 MHz, DMSO-d$_6$) δ 7.27 (t, J=6.9 Hz, 1H), 7.41 (br s, 1H), 7.54-7.62 (m, 3H), 7.82-7.89 (m, 1H), 7.93-7.98 (m, 3H), 8.33 (s, 1H), 13.45 (br s, 1H); APCI-MS (m/z) 446 (M+H)$^+$.

Example 24

4-[3-(2,6-Dichlorobenzoyl)-6-fluoro-1H-indol-1-yl]-3-fluorobenzoic acid

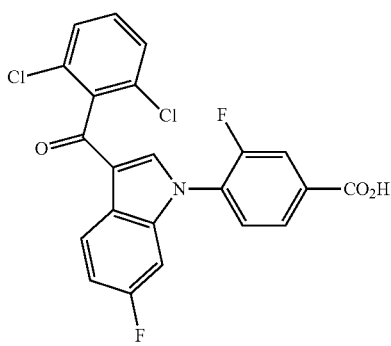 [SMILES: O=C(O)c1ccc(-n2cc(C(=O)c3c(Cl)cccc3Cl)c3ccc(F)cc32)c(F)c1]

Step 1: Ethyl 4-[3-(2,6-dichlorobenzoyl)-6-fluoro-1H-indol-1-yl]-3-fluorobenzoate The title compound was prepared by acylation reaction of Intermediate 9 (300 mg, 0.995 mmol) with 2,6-dichlorobenzoyl chloride (0.43 mL, 2.907 mmol) using aluminium trichloride (797 mg, 5.974 mmol) in DCM (5 mL) as per the process described in step 1 of Example 15 to give 310 mg of the product as off white solid. $^1$H NMR (300 MHz, DMSO-$d_6$) δ 1.34 (t, J=6.9 Hz, 3H), 4.37 (q, J=6.9 Hz, 2H), 7.25-7.31 (m, 2H), 7.53-7.60 (m, 3H), 7.88-7.99 (m, 3H), 8.27 (s, 2H); APCI-MS (m/z) 474 (M+H)$^+$.

Step 2: 4-[3-(2,6-Dichlorobenzoyl)-6-fluoro-1H-indol-1-yl]-3-fluorobenzoic acid The title compound was prepared by the hydrolysis of step 1 intermediate (300 mg, 0.6325 mmol) using lithium hydroxide (106 mg, 2.530 mmol) in THF (10 mL) and water (2 mL) as per the process described in step 2 of Example 1 to yield 265 mg of the product as off white solid. $^1$H NMR (300 MHz, DMSO-$d_6$) δ 7.25-7.31 (m, 2H), 7.53-7.60 (m, 3H), 7.85 (br s, 1H), 7.93 (d, J=7.8 Hz, 2H), 8.26 (s, 2H); APCI-MS (m/z) 446 (M)$^+$.

Example 25

4-[3-(2,6-Dichlorobenzoyl)-7-fluoro-1H-indol-1-yl]-3-fluorobenzoic acid

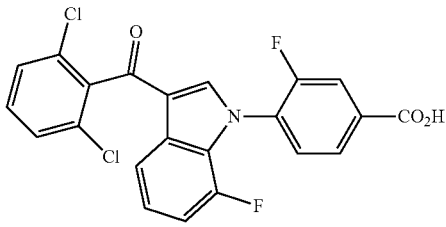 [SMILES: O=C(O)c1ccc(-n2cc(C(=O)c3c(Cl)cccc3Cl)c3cccc(F)c32)c(F)c1]

Step 1: Ethyl 4-[3-(2,6-dichlorobenzoyl)-7-fluoro-1H-indol-1-yl]-3-fluorobenzoate The title compound was prepared from acylation reaction of Intermediate 10 (200 mg, 0.663 mmol) with 2,6-dichlorobenzoyl chloride (0.28 mL, 1.991 mmol) using aluminium trichloride (531 mg, 3.982 mmol) in DCM (5 mL) as per the process described in step 1 of Example 15 to yield 205 mg of the product as sticky solid. $^1$H NMR (300 MHz, DMSO-$d_6$) δ 1.34 (t, J=6.9 Hz, 3H), 4.37 (q, J=6.9 Hz, 2H), 7.20-7.28 (m, 1H), 7.38 (br s, 1H), 7.53-7.62 (m, 3H), 7.90-7.96 (m, 3H), 8.06 (br s, 1H), 8.27 (s, 1H); APCI-MS (m/z) 474 (M)$^+$.

Step 2: 4-[3-(2,6-Dichlorobenzoyl)-7-fluoro-1H-indol-1-yl]-3-fluorobenzoic acid The title compound was prepared by the hydrolysis of step 1 intermediate (200 mg, 0.4216 mmol) using lithium hydroxide (70 mg, 1.6867 mmol) in THF (10 mL) and water (2 mL) as per the process described in step 2 of Example 1 to yield 180 mg of the product as white solid. $^1$H NMR (300 MHz, DMSO-$d_6$) δ 7.20-7.27 (m, 1H), 7.40 (br s, 1H), 7.53-7.61 (m, 3H), 7.83-7.92 (m, 3H), 8.06 (br s, 1H), 8.26 (s, 1H), 13.57 (br s, 1H); ESI-MS (m/z) 446 (M)$^+$.

Example 26

4-[3-(2,6-Dichloro-benzoyl)-6-dimethylcarbamoyl-indol-1-yl]-3-fluoro-benzoic acid

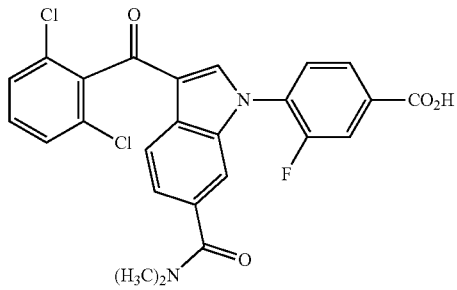

Step 1: Ethyl 4-[3-(2,6-dichloro-benzoyl)-6-dimethylcarbamoyl-indol-1-yl]-3-fluorobenzoate The title compound was prepared by the acylation reaction of intermediate 11 (100 mg, 0.282 mmol) with 2,6-dichlorobenzoyl chloride (0.121 mL, 0.846 mmol) in the presence of aluminium trichloride (226 mg, 1.69 mmol) in DCM (10 mL) as per the process described step 1 of Example 15 to yield 100 mg of the product as off white solid. $^1$H NMR (300 MHz, DMSO-$d_6$) δ 1.34 (t, J=6.9 Hz, 3H), 2.94 (br s, 6H), 4.37 (q, J=6.9 Hz, 2H), 7.39-7.47 (m, 2H), 7.56-7.61 (m, 3H), 7.85-8.01 (m, 3H), 8.25-8.35 (m, 2H).

Step 2: 4-[3-(2,6-Dichloro-benzoyl)-6-dimethylcarbamoyl-indol-1-yl]-3-fluoro-benzoic acid The title compound was prepared by the hydrolysis of step 1 (100 mg, 0.1896 mmol) using lithium hydroxide (31 mg, 0.7584 mmol) in THF (5 mL) and water (1 mL) as per the process described in step 2 of Example 1 to yield 81 mg of the product as off white solid. $^1$H NMR (300 MHz, DMSO-$d_6$) δ 2.95 (br s, 6H), 7.39-7.47 (m, 2H), 7.56-7.59 (m, 3H), 7.85-7.96 (m, 3H), 8.27-8.34 (m, 2H), 13.60 (br s, 1H); APCI-MS (m/z) 499 (M)$^+$.

Example 27

4-[3-(2,6-Dichlorobenzoyl)-1H-pyrrolo[2,3-b]pyridin-1-yl]-3-fluorobenzoic acid

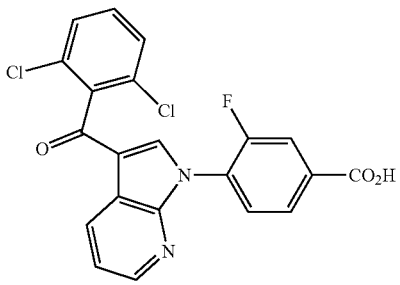 [SMILES: O=C(O)c1ccc(-n2cc(C(=O)c3c(Cl)cccc3Cl)c3cccnc32)c(F)c1]

Step 1: Ethyl 4-[3-(2,6-dichlorobenzoyl)-1H-pyrrolo[2,3-b]pyridin-1-yl]-3-fluorobenzoate The title compound was prepared by the acylation of Intermediate 12 (300 mg, 1.055 mmol) with 2,6-dichlorobenzoyl chloride (0.45 mL, 3.165 mmol) using aluminium trichloride (845 mg, 6.331 mmol) in DCM (5 mL) as per the process described in step 1 of Example 15 to yield 310 mg of the product as off white solid. $^1$H NMR (300 MHz, DMSO-$d_6$) δ 1.34 (t, J=6.9 Hz, 3H), 4.35 (q, J=6.9 Hz, 2H), 7.48-7.56 (m, 1H), 7.57-7.63 (m, 3H), 7.89-7.97 (m, 3H), 8.44-8.50 (m, 3H); APCI-MS (m/z) 457 (M+H)$^+$.

Step 2: 4-[3-(2,6-Dichlorobenzoyl)-1H-pyrrolo[2,3-b]pyridin-1-yl]-3-fluorobenzoic acid The title compound was prepared by the hydrolysis of step 1 intermediate (300 mg, 0.656 mmol) using lithium hydroxide (110 mg, 2.6242 mmol) in THF (10 mL) and water (2 mL) as per the process described in step 2 of Example 1 to yield 250 mg of the product as off white solid. $^1$H NMR (300 MHz, DMSO-$d_6$) δ 7.48-7.52 (m, 1H), 7.56-7.63 (m, 3H), 7.89-7.94 (m, 3H), 8.44-8.50 (m, 3H); APCI-MS (m/z) 429 (M+H)$^+$.

Example 28

4-[3-(Phenylcarbonyl)-1H-indazol-1-yl]benzoic acid

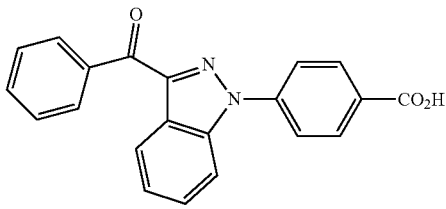 [SMILES: O=C(O)c1ccc(-n2nc(C(=O)c3ccccc3)c3ccccc32)cc1]

Step 1: Ethyl 4-[3-(phenylcarbonyl)-1H-indazol-1-yl]benzoate

The title compound was prepared by the reaction of Intermediate 13 (100 mg, 0.450 mmol) with ethyl 4-iodobenzoate (186 mg, 0.675 mmol) using L-proline (20 mg, 0.180 mmol), potassium carbonate (248 g, 1.801 mmol) and copper iodide (17 mg, 0.090 mmol) in DMSO (5 mL) as per the process described in step 1 of Example 21 to yield 85 mg of the product as off white solid. $^1$H NMR (300 MHz, CDCl$_3$) δ 1.44 (t, J=7.5 Hz, 3H), 4.44 (q, J=7.5 Hz, 2H), 7.47-7.64 (m, 5H), 7.84-7.93 (m, 3H), 8.27 (d, J=8.1 Hz, 2H), 8.41 (d, J=6.9 Hz, 2H), 8.57 (d, J=7.8 Hz, 1H); APCI-MS (m/z) 343 (M+H)$^+$.

Step 2: 4-[3-(Phenylcarbonyl)-1H-indazol-1-yl]benzoic acid

The title compound was prepared by the hydrolysis of step 1 intermediate (80 mg, 0.2159 mmol) using lithium hydroxide (36 mg, 0.8639 mmol) in THF (3 mL) and water (2 mL) as per the process described in step 2 of Example 1 to yield 70 mg of the product as off white solid. $^1$H NMR (300 MHz, CDCl$_3$) δ 7.55-7.68 (m, 5H), 8.05 (d, J=7.2 Hz, 3H), 8.20 (d, J=8.4 Hz, 2H), 8.31 (d, J=7.8 Hz, 2H), 8.43 (d, J=7.8 Hz, 1H), 13.24 (br s, 1H); APCI-MS (m/z) 343 (M+H)$^+$.

Example 29

4-[3-(2,6-Dichlorobenzoyl)-1H-indazol-1-yl]benzoic acid

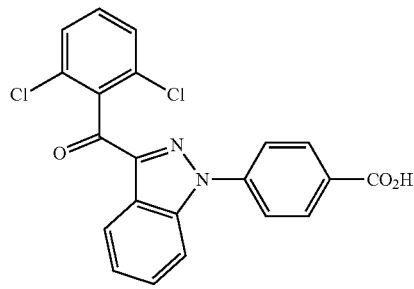

Step 1: Ethyl 4-[3-(2,6-dichlorobenzoyl)-1H-indazol-1-yl]benzoate

The title compound was prepared by reaction of Intermediate 14 (150 mg, 0.515 mmol) with ethyl 4-iodobenzoate (170 mg, 0.618 mmol) using L-proline (23 mg, 0.205 mmol), potassium carbonate (280 mg, 2.050 mmol) and copper iodide (19 mg, 0.103 mmol) in DMSO (5 mL) as per the process described in step 1 of Example 21 to give the 100 mg of the product as off white solid. $^1$H NMR (300 MHz, DMSO-$d_6$) δ 1.34 (t, J=6.9 Hz, 3H), 4.35 (q, J=6.9 Hz, 2H), 7.58-7.75 (m, 5H), 7.87 (d, J=9.0 Hz, 2H), 8.03 (d, J=8.4 Hz, 1H), 8.17 (d, J=9.0 Hz, 2H), 8.41 (d, J=8.4 Hz, 1H).

Step 2: 4-[3-(2,6-Dichlorobenzoyl)-1H-indazol-1-yl]benzoic acid

The title compound was prepared by the hydrolysis of step 1 intermediate (100 mg, 0.227 mmol) using lithium hydroxide (38 mg, 0.9105 mmol) in THF (5 mL) and water (1 mL) as per the process described in step 2 of Example 1 to yield 60 mg of the product as white solid. $^1$H NMR (300 MHz, DMSO-$d_6$) δ 7.61-7.73 (m, 5H), 7.85 (d, J=8.4 Hz, 2H), 8.03 (d, J=9.0 Hz, 1H), 8.16 (d, J=7.8 Hz, 2H), 8.41 (d, J=8.4 Hz, 1H), 13.25 (br s, 1H).

Example 30

4-(3-Benzoyl-1H-indazol-1-yl)-3-fluorobenzoic acid

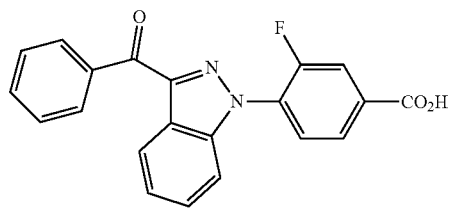 [SMILES: O=C(O)c1ccc(-n2nc(C(=O)c3ccccc3)c3ccccc32)c(F)c1]

Step 1: Ethyl 4-(3-benzoyl-1H-indazol-1-yl)-3-fluorobenzoate

The title compound was prepared by the reaction of Intermediate 13 (200 mg, 0.900 mmol) with ethyl 3-fluoro-4-iodobenzoate (291 mg, 0.990 mmol) using L-proline (41 mg, 0.360 mmol), potassium carbonate (497 mg, 3.600 mmol) and copper iodide (34 mg, 0.180 mmol) in DMSO (5 mL) as per the process described in step 1 of Example 21 to yield 27 mg of the product as yellow sticky solid. $^1$H NMR (300 MHz, DMSO-$d_6$) δ 1.35 (t, J=7.5 Hz, 3H), 4.38 (q, J=7.5 Hz, 2H), 7.57-7.64 (m, 4H), 7.66 (br s, 2H), 8.03 (br s, 3H), 8.25-8.30 (m, 2H), 8.38 (br s, 1H); ESI-MS (m/z) 389 (M+H)$^+$.

Step 2: 4-(3-Benzoyl-1H-indazol-1-yl)-3-fluorobenzoic acid

The title compound was prepared by the hydrolysis of step 1 intermediate (25 mg, 0.0643 mmol) using lithium hydroxide (10 mg, 0.257 mmol) in THF (4 mL) and water (1 mL) as per the process described in step 2 of Example 1 to yield 17 mg of the product as off white solid. $^1$H NMR (300 MHz, DMSO-$d_6$) δ 7.57-7.62 (m, 4H), 7.66 (br s, 2H), 8.03 (br s, 3H), 8.28 (d, J=7.5 Hz, 2H), 8.41 (d, J=7.8 Hz, 1H), 13.61 (br s, 1H); ESI-MS (m/z) 361 (M+H)$^+$.

Example 31

4-[3-(2,6-Dichlorobenzoyl)-1H-indazol-1-yl]-3-fluorobenzoic acid

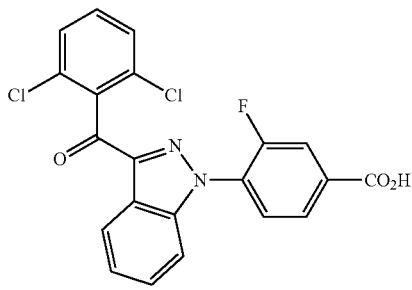 [SMILES: O=C(O)c1ccc(-n2nc(C(=O)c3c(Cl)cccc3Cl)c3ccccc32)c(F)c1]

Step 1: Ethyl 4-[3-(2,6-dichlorobenzoyl)-1H-indazol-1-yl]-3-fluorobenzoate

The title compound was prepared by the reaction of Intermediate 14 (600 mg, 2.050 mmol) with ethyl 3-fluoro-4-iodobenzoate (99 mg, 3.091 mmol) using L-proline (94 mg, 0.824 mmol), potassium carbonate (1.13 g, 8.243 mmol) and copper iodide (78 mg, 0.412 mmol) in DMSO (5 mL) as per the process described in step 1 of Example 21 to yield 60 mg of the product as off white solid. $^1$H NMR (300 MHz, DMSO-$d_6$) δ 1.32 (t, J=7.2 Hz, 3H), 4.37 (q, J=7.2 Hz, 2H), 7.55-7.68 (m, 6H), 7.82-7.89 (m, 1H), 8.02 (t, J=9.3 Hz, 2H), 8.39 (d, J=8.4 Hz, 1H).

Step 2: 4-[3-(2,6-Dichlorobenzoyl)-1H-indazol-1-yl]-3-fluorobenzoic acid

The title compound was prepared by the hydrolysis of step 1 intermediate (50 mg, 0.1312 mmol) using lithium hydroxide (22 mg, 0.5248 mmol) in THF (5 mL) and water (1 mL) as per the process described in step 2 of Example 1 to yield 30 mg of the product as off white solid. $^1$H NMR (300 MHz, DMSO-$d_6$) δ 7.54-7.67 (m, 6H), 7.82 (d, J=7.8 Hz, 1H), 7.97-8.02 (m, 2H), 8.40 (d, J=7.8 Hz, 1H), 13.65 (br s, 1H); ESI-MS (m/z) 429 (M)$^+$.

Example 32

4-{3-[(2,6-Dichlorophenyl)carbonyl]-7-fluoro-1H-indazol-1-yl}benzoic acid

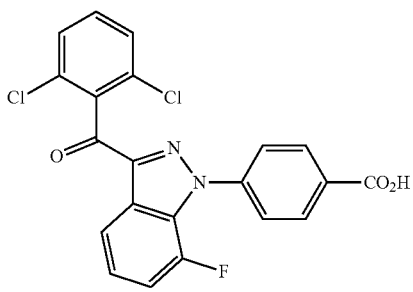 [SMILES: O=C(O)c1ccc(-n2nc(C(=O)c3c(Cl)cccc3Cl)c3cccc(F)c32)cc1]

Step 1: Ethyl 4-{3-[(2,6-dichlorophenyl)carbonyl]-7-fluoro-1H-indazol-1-yl}benzoate The title compound was prepared by the reaction of Intermediate 15 (200 mg, 0.646 mmol) with ethyl 4-iodobenzoate (260 mg, 0.970 mmol) using L-proline (29 mg, 0.258 mmol), potassium carbonate (357 mg, 2.58 mmol) and copper iodide (24 mg, 0.129 mmol) in DMSO (5 mL) as per the process described in step 1 of Example 21 to yield 65 mg of the product as off white solid. $^1$H NMR (300 MHz, DMSO-$d_6$) δ 1.33 (t, J=6.6 Hz, 3H), 4.34 (q, J=6.6 Hz, 2H), 7.55-7.65 (m, 5H), 7.77-7.82 (m, 2H), 8.13 (d, J=8.4 Hz, 2H), 8.20-8.24 (m, 1H).

Step 2: 4-{3-[(2,6-Dichlorophenyl)carbonyl]-7-fluoro-1H-indazol-1-yl}benzoic acid The title compound was prepared by the hydrolysis of step 1 intermediate (60 mg, 0.1312 mmol) using lithium hydroxide (22 mg, 0.5248 mmol) in THF (5 mL) and water (1 mL) as per the process described in step 2 of Example 1 to yield 40 mg of the product as off white solid. $^1$H NMR (300 MHz, DMSO-$d_6$) δ 7.55-7.65 (m, 5H), 7.77 (d, J=6.0 Hz, 2H), 8.10 (d, J=7.8 Hz, 2H), 8.20-8.24 (m, 1H), 13.28 (br s, 1H); APCI-MS (m/z) 428 (M)$^+$.

Example 33

4-(3-{[2-Chloro-6-(trifluoromethyl)phenyl]carbonyl}-1H-indazol-1-yl)-3-fluorobenzoic acid

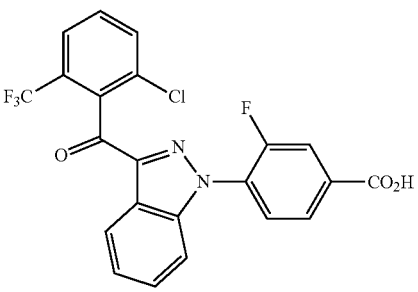 [SMILES: O=C(O)c1ccc(-n2nc(C(=O)c3c(Cl)cccc3C(F)(F)F)c3ccccc32)c(F)c1]

Step 1: Ethyl 4-(3-{[2-chloro-6-(trifluoromethyl)phenyl]carbonyl}-1H-indazol-1-yl)-3-fluorobenzoate The title compound was prepared by coupling Intermediate 16 (200 mg, 0.615 mmol) with ethyl 3-fluoro-4-iodobenzoate (270 mg, 0.923 mmol) using L-proline (28 mg, 0.246 mmol), potassium carbonate (340 mg, 2.46 mmol) and copper iodide (23 mg, 0.123 mmol) in DMSO (5 mL) as per the process described in step 1 of Example 21 to yield 25 mg of the product as yellow semi-solid. $^1$H NMR (300 MHz, DMSO-$d_6$) δ 1.33 (t, J=6.9 Hz, 3H), 4.37 (q, J=6.9 Hz, 2H), 7.60-7.70 (m, 3H), 7.79-7.83 (m, 3H), 7.91-8.05 (m, 3H), 8.38 (br s, 1H); ESI-MS (m/z) 490 (M+H)$^+$.

Step 2: 4-(3-{[2-Chloro-6-(trifluoromethyl)phenyl]carbonyl}-1H-indazol-1-yl)-3-fluorobenzoic acid The title compound was prepared by the hydrolysis of step 1 intermediate (21 mg, 0.0427 mmol) using lithium hydroxide (7 mg, 0.1711 mmol) in THF (5 mL) and water (1 mL) as per the process described in step 2 of Example 1 to yield 13 mg of the product as off white solid; $^1$H NMR (300 MHz, DMSO-$d_6$) δ 7.64-7.77 (m, 3H), 7.79-7.80 (m, 2H), 7.91-7.95 (m, 4H), 8.39-8.41 (m, 1H), 13.66 (br s, 1H); APCI-MS (m/z) 462 (M)$^+$.

Example 34

4-(3-{[2-Chloro-6-(trifluoromethyl)phenyl]carbonyl}-1H-indazol-1-yl)-benzoic acid

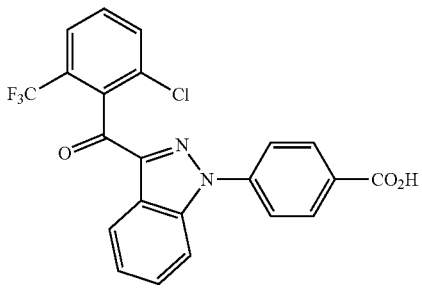

Step 1: Ethyl 4-(3-{[2-chloro-6-(trifluoromethyl)phenyl]carbonyl}-1H-indazol-1-yl)-benzoate The title compound was prepared by the coupling reaction of Intermediate 16 (50 mg, 0.153 mmol) with ethyl 4-iodobenzoate (63 mg, 0.230 mmol) using L-proline (7 mg, 0.061 mmol), potassium carbonate (85 mg, 0.615 mmol) and copper iodide (5 mg, 0.030 mmol) in DMSO (3 mL) as per the process described in step 1 of Example 21 to yield 60 mg of the product as off white semi-solid. $^1$H NMR (300 MHz, DMSO-$d_6$) δ 1.33 (t, J=7.5 Hz, 3H), 4.35 (q, J=7.5 Hz, 2H), 7.61 (t, J=7.5 Hz, 1H), 7.72 (t, J=8.7 Hz, 1H), 7.81-7.87 (m, 3H), 7.90-8.05 (m, 3H), 8.17 (d, J=8.1 Hz, 2H), 8.37-8.44 (m, 1H); ESI-MS (m/z) 472 (M)$^+$.

Step 2: 4-(3-{[2-Chloro-6-(trifluoromethyl)phenyl]carbonyl}-1H-indazol-1-yl)-benzoic acid The title compound was prepared by the hydrolysis of step 1 intermediate (55 mg, 0.1163 mmol) using lithium hydroxide (19 mg, 0.4652 mmol) in THF (5 mL) and water (1 mL) as per the process described in step 2 of Example 1 to yield 30 mg of the product as white solid. $^1$H NMR (300 MHz, DMSO-$d_6$) δ 7.58-7.63 (m, 1H), 7.69-7.74 (m, 1H), 7.82 (d, J=8.7 Hz, 3H), 7.94-8.04 (m, 3H), 8.14 (d, J=9.0 Hz, 2H), 8.16 (d, J=7.5 Hz, 1H), 13.27 (br s, 1H); APCI-MS (m/z) 444 (M+H)$^+$.

Example 35

4-{3-[(2-Chloro-6-cyclopropylphenyl)carbonyl]-7-fluoro-1H-indazol-1-yl}benzoic acid

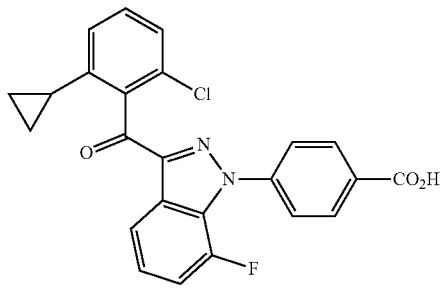

Step 1: Ethyl 4-{3-[(2-chloro-6-cyclopropylphenyl)carbonyl]-7-fluoro-1H-indazol-1-yl}benzoate To a stirred solution of Intermediate 17 (150 mg, 0.476 mmol) and ethyl 4-iodobenzoate (197 mg, 0.715 mmol) in DMSO (5 mL) in a sealed tube, were added L-proline (21 mg, 0.190 mmol), potassium carbonate (263 mg, 1.90 mmol) and copper iodide (18 mg, 0.095 mmol) at room temperature. The reaction mixture was stirred at 100° C. for 18 hours. The reaction mixture was cooled to RT and diluted with water (20 mL). The aqueous mixture was extracted with ethyl acetate (3×20 mL). The combined organic layers were washed with water (50 mL) and brine (50 mL). The solution was dried over anhydrous sodium sulphate and the solvents were removed under reduced pressure. The residue thus obtained was purified by silica gel column chromatography to yield 75 mg of the title product as off white semi-solid. $^1$H NMR (300 MHz, DMSO-$d_6$) δ 0.67-0.90 (m, 4H), 1.34 (t, J=6.9 Hz, 3H), 1.69-1.75 (m, 1H), 4.35 (q, J=7.2 Hz, 2H), 7.06 (d, J=6.9 Hz, 1H), 7.35-7.48 (m, 2H), 7.51-7.58 (m, 2H), 7.77-7.83 (m, 2H), 8.13 (d, J=8.4 Hz, 2H), 8.20-8.26 (m, 1H).

Step 2: 4-{3-[(2-Chloro-6-cyclopropylphenyl)carbonyl]-7-fluoro-1H-indazol-1-yl}benzoic acid To a stirred and cooled (0° C.) solution of Step 1 intermediate (70 mg, 0.151 mmol) in a mixture of THF (5 mL) and water (1 mL) was added lithium hydroxide (31 mg, 0.456 mmol). The reaction mixture was stirred at RT for 24 h. The solvents were distilled out under reduced pressure to afford the sticky residue which was diluted with water and acidified with 1N HCl. The precipitate thus obtained was filtered and washed with water. The obtained solid was triturated with n-hexane (20 mL) and dried well to obtain 35 mg of the title product as off white solid. $^1$H NMR (300 MHz, DMSO-$d_6$) δ 0.65-0.91 (m, 4H), 1.80-1.91 (m, 1H), 7.01-7.07 (m, 1H), 7.28-7.39 (m, 2H), 7.40-7.55 (m, 2H), 7.68-7.77 (m, 2H), 8.10 (d, J=6.9 Hz, 2H), 8.20-8.23 (m, 1H), 13.28 (br s, 1H); APCI-MS (m/z) 435 (M)+.

Example 36

4-{3-[(2,6-Dichlorophenyl)carbonyl]-1H-pyrazolo[3,4-b]pyridin-1-yl}benzoic acid

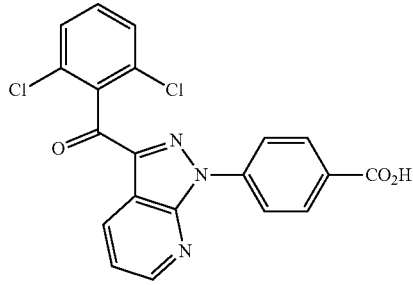 [SMILES: O=C(O)c1ccc(-n2nc(C(=O)c3c(Cl)cccc3Cl)c3cccnc32)cc1]

Step 1: Ethyl 4-{3-[(2,6-dichlorophenyl)carbonyl]-1H-pyrazolo[3,4-b]pyridin-1-yl}benzoate The title compound was prepared by reaction of Intermediate 18 (200 mg, 0.684 mmol) with ethyl 4-iodobenzoate (280 mg, 1.02 mmol) using L-proline (31 mg, 0.269 mmol), potassium carbonate (378 mg, 2.73 mmol) and copper iodide (26 mg, 0.136 mmol) in DMSO (5 mL) as per the process described in step 1 of Example 21 to yield 200 mg of the product as off white solid. $^1$H NMR (300 MHz, DMSO-$d_6$) δ 1.33 (t, J=6.9 Hz, 3H), 4.33 (q, J=6.9 Hz, 2H), 7.61-7.72 (m, 4H), 8.15 (d, J=9.0 Hz, 2H), 8.28 (d, J=8.7 Hz, 2H), 8.80 (d, J=8.4 Hz, 1H), 8.89 (br s, 1H); APCI-MS (m/z) 440 (M)+.

Step 2: 4-{3-[(2,6-Dichlorophenyl)carbonyl]-1H-pyrazolo[3,4-b]pyridin-1-yl}benzoic acid The title compound was prepared by the hydrolysis of step 1 intermediate (200 mg, 0.4542 mmol) using lithium hydroxide (76 mg, 1.1870 mmol) in THF (5 mL) and water (2 mL) as per the process described in step 2 of Example 1 to yield 120 mg of the product as off white solid. $^1$H NMR (300 MHz, DMSO-$d_6$) δ 7.61-7.73 (m, 4H), 8.18 (dd, J=8.7, 33 Hz, 4H), 8.80 (d, J=6.6 Hz, 1H), 8.80 (d, J=3.3 Hz, 1H), 13.18 (br s, 1H); APCI-MS (m/z) 412 (M)+.

Example 37

4-{3-[(2-Chloro-6-cyclopropylphenyl)carbonyl]-1H-pyrazolo[3,4-b]pyridin-1-yl}benzoic acid

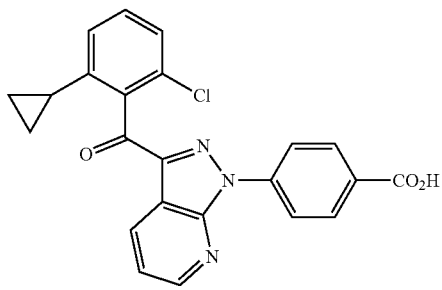 [SMILES: O=C(O)c1ccc(-n2nc(C(=O)c3c(Cl)cccc3C3CC3)c3cccnc32)cc1]

Step 1: Ethyl 4-{3-[(2-chloro-6-cyclopropylphenyl)carbonyl]-1H-pyrazolo[3,4-b]pyridin-1-yl}benzoate To a stirred solution of Intermediate 19 (250 mg, 0.839 mmol) and ethyl 4-iodobenzoate (340 mg, 1.259 mmol) in DMSO (5 mL) in a sealed tube, were added L-proline (38 mg, 0.335 mmol), potassium carbonate (460 mg, 3.358 mmol) and copper iodide (31 mg, 0.167 mmol) at room temperature. The reaction mixture was stirred at 100° C. for 18 hours. The reaction mixture was cooled to RT and diluted with water (20 mL). The aqueous mixture was extracted with ethyl acetate (3×20 mL). The combined organic layers were washed with water (50 mL) and brine (50 mL). The solution was dried over anhydrous sodium sulphate and the solvents were removed under reduced pressure. The residue thus obtained was purified by silica gel column chromatography to yield 210 mg of the title product as off white semi-solid. $^1$H NMR (300 MHz, DMSO-$d_6$) δ 0.67-0.95 (m, 4H), 1.33 (t, J=7.5 Hz, 3H), 1.62-1.75 (m, 1H), 4.34 (q, J=7.5 Hz, 2H), 7.11 (d, J=6.9 Hz, 1H), 7.40-7.52 (m, 2H), 7.65-7.72 (m, 1H), 8.16 (d, J=8.7 Hz, 2H), 8.32 (d, J=9.0 Hz, 2H), 8.75 (d, J=7.8 Hz, 1H), 8.86 (br s, 1H); APCI-MS (m/z) 446 (M+H)+.

Step 2: 4-{3-[(2-chloro-6-cyclopropylphenyl)carbonyl]-1H-pyrazolo[3,4-b]pyridin-1-yl}benzoic acid To a stirred and cooled (0° C.) solution of Step 1 intermediate (200 mg, 0.448 mmol) in a mixture of THF (10 mL) and water (4 mL) was added lithium hydroxide (94 mg, 2.2426 mmol). The reaction mixture was stirred at RT for 24 h. The solvents were distilled out under reduced pressure to afford the sticky residue which was diluted with water and acidified with 1N HCl. The precipitate thus obtained was filtered and washed with water. The obtained solid was triturated with n-hexane (20 mL) and dried well to obtain 125 mg of the title product as off white solid. $^1$H NMR (300 MHz, DMSO-$d_6$) δ 0.67-0.95 (m, 4H), 1.62-1.75 (m, 1H), 7.09 (d, J=7.2 Hz, 1H), 7.39-7.48 (m, 2H), 7.64-7.68 (m, 1H), 8.20 (dd, J=8.7, 39 Hz, 4H), 8.73 (d, J=7.2 Hz, 1H), 8.84 (d, J=3.6 Hz, 1H), 13.18 (br s, 1H); APCI-MS (m/z) 418 (M+H)+.

Example 38

4-(3-{[2-Chloro-6-(trifluoromethyl)phenyl]carbonyl}-1H-pyrazolo[3,4-b]pyridin-1-yl)benzoic acid

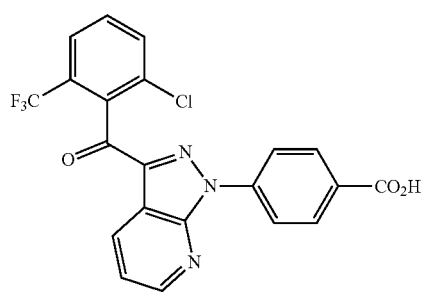 [SMILES: O=C(O)c1ccc(-n2nc(C(=O)c3c(Cl)cccc3C(F)(F)F)c3cccnc32)cc1]

Step 1: Ethyl 4-(3-{[2-chloro-6-(trifluoromethyl)phenyl]carbonyl}-1H-pyrazolo[3,4-b]pyridin-1-yl)benzoate The title compound was prepared by reaction of Intermediate 20 (600 mg, 1.8433 mmol) with ethyl 4-iodobenzoate (1 g, 3.6847 mmol) using L-proline (84 mg, 0.7359 mmol), potassium carbonate (1 g, 7.3694 mmol) and copper iodide (70 mg, 0.3684 mmol) in DMSO (6 mL) as per the process described in step 1 of Example 21 to yield 510 mg of the product as white solid. $^1$H NMR (300 MHz, DMSO-$d_6$) δ 1.31 (t, J=7.2 Hz, 3H), 4.32 (q, J=7.2 Hz, 2H), 7.70-7.77 (m, 1H), 7.80-7.90 (m, 1H), 7.95-8.05 (m, 2H), 8.10-8.17 (m, 2H), 8.20-8.28 (m, 2H), 8.70-8.81 (m, 1H), 8.89 (br s, 1H); APCI-MS (m/z) 462 (M)$^+$.

Step 2: 4-(3-{[2-Chloro-6-(trifluoromethyl)phenyl]carbonyl}-1H-pyrazolo[3,4-b]pyridin-1-yl)benzoic acid The title compound was prepared by the hydrolysis of step 1 intermediate (500 mg, 1.0552 mmol) using lithium hydroxide (265 mg, 6.331 mmol) in THF (10 mL) and water (3 mL) as per the process described in step 2 of Example 1 to yield 350 mg of the product as white solid. $^1$H NMR (300 MHz, DMSO-$d_6$) δ 7.70-7.75 (m, 1H), 7.80-7.90 (m, 1H), 7.95-8.02 (m, 2H), 8.15 (dd, J=7.8, 28.2 Hz, 4H), 8.81-8.91 (m, 2H), 13.21 (br s, 1H); APCI-MS (m/z) 446 (M+H)$^+$.

Example 39

Ethyl 4-{3-[(2,6-dichlorophenyl)carbonyl]-1H-indol-1-yl}-3-fluorobenzoate

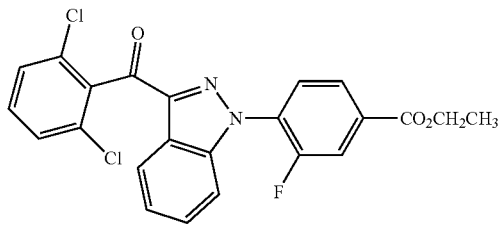

To a stirred suspension of aluminum chloride (16.9 g, 127.07 mmol) in DCM (30 mL) was added 2,6-dichlorobenzoyl chloride (9.11 mL, 63.53 mmol) and the mixture was stirred at RT for 15 min. A solution of Intermediate 5 (6 g, 21.17 mmol) in DCM (30 mL) was added drop wise to the reaction mixture was and it was stirred for 2 h at RT. Reaction mixture was poured on crushed ice. The layers were separated and the aqueous layer was extracted with ethyl acetate (2×100 mL). The combined organic extracts were washed with aqueous sodium bicarbonate (100 mL), water (50 mL), brine (25 mL) and dried (Na$_2$SO$_4$). The solvent was distilled under reduced pressure and the residue obtained was purified by silica gel column chromatography to yield 4.50 g of the title product as off white solid. $^1$H NMR (300 MHz, DMSO-$d_6$) δ 1.34 (t, J=6.9 Hz, 3H), 4.37 (q, J=6.9 Hz, 2H), 7.39 (br s, 3H), 7.54-7.62 (m, 3H), 7.86-8.01 (m, 3H), 8.23 (br s, 2H); APCI-MS (m/z) 456 (M+H)$^+$.

Example 40

Propyl 4-{3-[(2,6-dichlorophenyl)carbonyl]-1H-indol-1-yl}-3-fluorobenzoate

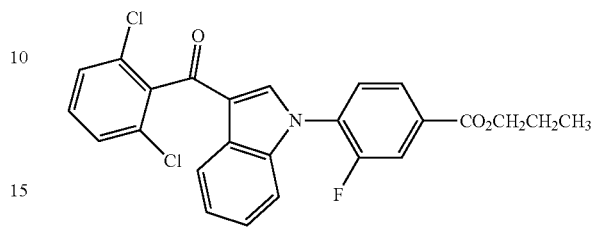

To a stirred solution of Example 19 (200 mg, 0.465 mmol) in DMF (5 mL) were added 1-bromopropane (0.22 mL, 2.276 mmol) and potassium carbonate (320 mg, 2.315 mmol), potassium iodide (77 mg, 0.466 mmol) and the reaction mixture was heated to 80° C. for 18 hours. The reaction mixture was cooled to RT and poured in to water (20 mL) and the product was extracted with ethyl acetate (2×20 mL). The combined organic layers were washed with brine (20 mL) and dried over anhydrous sodium sulfate. The solvent was distilled off and the residue obtained was purified by silica gel column chromatography to give 140 mg of the title product as off white solid. $^1$H NMR (300 MHz, DMSO-$d_6$) δ 0.97 (t, J=7.2 Hz, 3H), 1.75 (q, J=7.2 Hz, 2H), 4.28 (t, J=6.3 Hz, 2H), 7.39 (br s, 3H), 7.54-7.62 (m, 3H), 7.87-8.01 (m, 3H), 8.23 (s, 2H); APCI-MS (m/z) 470 (M+H)$^+$.

Example 41

Butyl 4-{3-[(2,6-dichlorophenyl)carbonyl]-1H-indol-1-yl}-3-fluorobenzoate

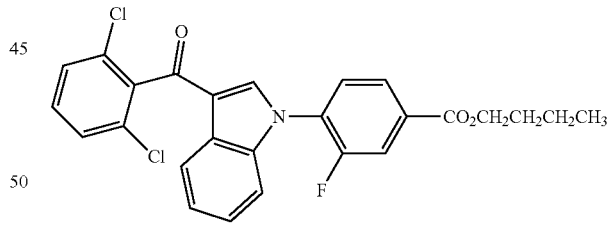

To a stirred solution of Example 19 (100 mg, 0.233 mmol) in DMF (5 mL) were added 1-iodobutane (15 μL, 0.116 mmol) and potassium carbonate (152 mg, 0.116 mmol) and the reaction mixture was heated to 90° C. for 16 hours. The reaction mixture was cooled to RT and poured in to water (10 mL) and the product was extracted with ethyl acetate (2×20 mL). The combined organic layers were washed with brine (20 mL) and dried over anhydrous sodium sulfate. The solvent was distilled off and the residue obtained was triturated with diethyl ether and n-pentane to give 52 mg of the title product as off white solid. $^1$H NMR (300 MHz, DMSO-$d_6$) δ 0.93 (t, J=7.2 Hz, 3H), 1.43 (q, J=7.2 Hz, 2H), 1.71 (t, J=6.3 Hz, 2H), 4.33 (t, J=6.3 Hz, 2H), 7.39 (br s, 3H), 7.54-7.62 (m, 3H), 7.87-8.01 (m, 3H), 8.23 (s, 2H).

Example 42

Ethyl 4-[3-(2,6-dichloro-benzoyl)-7-fluoro-1H-indol-1-yl]-3-fluorobenzoate

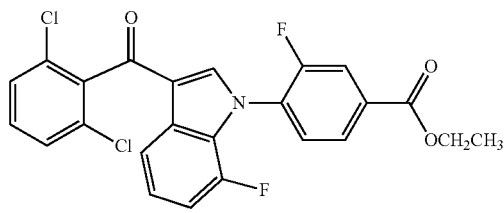 [SMILES: CCOC(=O)c1ccc(-n2cc(C(=O)c3c(Cl)cccc3Cl)c3cccc(F)c32)c(F)c1]

To a stirred suspension of aluminum chloride (264 mg, 0.918 mmol) in DCM (5 mL) was added 2,6-dichlorobenzoyl chloride (0.12 mL, 0.992 mmol) and the mixture was stirred at RT for 15 min. A solution of Intermediate 10 (100 mg, 0.333 mmol) in DCM (5 mL) was added drop wise to the reaction mixture was and it was stirred for 2 h at RT. The reaction mixture was poured on crushed ice. The layers were separated and the aqueous layer was extracted with ethyl acetate (2×10 mL). The combined organic extracts were washed with aqueous sodium bicarbonate (10 mL), water (10 mL), brine (15 mL) and dried ($Na_2SO_4$). The solvent was distilled under reduced pressure and the residue obtained was purified by silica gel column chromatography to yield 83 mg of the title product as off white solid. $^1$H NMR (300 MHz, DMSO-$d_6$) δ 1.33 (t, J=6.9 Hz, 3H), 4.37 (q, J=6.9 Hz, 2H), 7.25-7.30 (m, 1H), 7.40 (br s, 1H), 7.55-7.62 (m, 3H), 7.90-7.96 (m, 3H), 8.08 (br s, 1H), 8.27 (s, 1H); ESI-MS (m/z) 474 (M+H)$^+$.

Example 43

Propyl 4-[3-(2,6-dichloro-benzoyl)-7-fluoro-1H-indol-1-yl]-3-fluorobenzoate

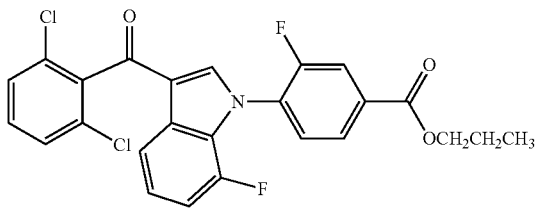

To a stirred solution of Example 25 (50 mg, 0.112 mmol) in DMF (5 mL) were added 1-bromopropane (5 μL, 0.561 mmol) and potassium carbonate (77 mg, 0.563 mmol) and the reaction mixture was heated to 70° C. for 16 hours. The reaction mixture was concentrated under reduced pressure and the residue was diluted with water (10 mL). The product was extracted with ethyl acetate (2×20 mL). The combined organic layers were washed with brine (20 mL) and dried over anhydrous sodium sulfate. The solvent was distilled off and the residue obtained was triturated with diethyl ether and n-pentane to give 25 mg of the title product as off white solid. $^1$H NMR (300 MHz, DMSO-$d_6$) δ 0.97 (t, J=6.9 Hz, 3H), 1.75 (q, J=6.9 Hz, 2H), 4.27 (br s, 2H), 7.23 (br s, 1H), 7.39 (br s, 1H), 7.50-7.60 (m, 3H), 7.90-8.01 (m, 3H), 8.08 (br s, 1H), 8.27 (s, 1H); ESI-MS (m/z) 474 (M+H)$^+$.

Example 44

Butyl 4-[3-(2,6-dichloro-benzoyl)-7-fluoro-1H-indol-1-yl]-3-fluorobenzoate

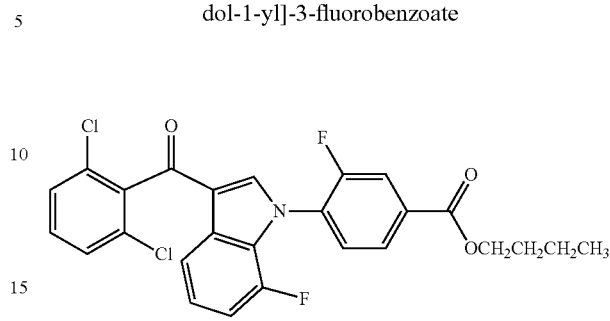

To a stirred solution of Example 25 (50 mg, 0.112 mmol) in DMF (2 mL) were added 1-iodobutane (6 μL, 0.561 mmol) and potassium carbonate (77 mg, 0.563 mmol) and the reaction mixture was heated to 90° C. for 16 hours. The reaction mixture was concentrated under reduced pressure and the residue was diluted with water (10 mL). The product was extracted with ethyl acetate (2×20 mL). The combined organic layers were washed with brine (20 mL) and dried over anhydrous sodium sulfate. The solvent was distilled off and the residue obtained was triturated with diethyl ether and n-pentane to give 21 mg of the title product as off white solid. $^1$H NMR (300 MHz, DMSO-$d_6$) δ 0.93 (t, J=6.9 Hz, 3H), 1.44 (q, J=6.9 Hz, 2H), 1.71 (br s, 2H), 4.33 (br s, 2H), 7.25 (br s, 1H), 7.40 (br s, 1H), 7.50-7.60 (m, 3H), 7.85-8.01 (m, 3H), 8.07 (br s, 1H), 8.27 (s, 1H).

Example 45

Ethyl 4-{3-[2-chloro-6-(trifluoromethyl)phenoxy]-1H-indazol-1-yl}-3-fluorobenzoate

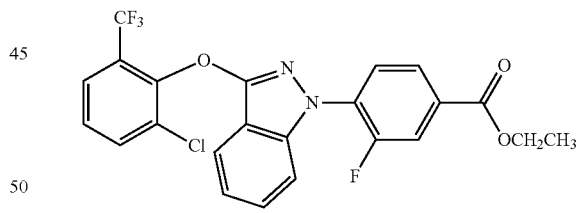

To a stirred solution of Example 7 (250 mg, 0.554 mmol) in ethyl alcohol (10 mL) was added catalytic amount of sulfuric acid and the reaction mixture was refluxed for 18 hours. The mixture was cooled to RT and concentrated under reduced pressure. The residue was diluted with ethyl acetate (20 mL) and washed with sodium bicarbonate solution (20 mL) followed by brine (20 mL). The organic layer was dried over anhydrous sodium sulfate and concentrated under reduced pressure. The residue thus obtained was triturated with a mixture of diethyl ether and n-pentane to obtain 207 mg of the title product as off white solid. $^1$H NMR (300 MHz, DMSO-$d_6$) δ 1.33 (t, J=7.5 Hz, 3H), 4.35 (q, J=7.5 Hz, 2H), 7.39 (t, J=7.8 Hz, 1H), 7.40-7.50 (m, 1H), 7.62 (br s, 3H), 7.82-8.04 (m, 5H); ESI-MS (m/z) 479 (M+H)$^+$.

Example 46

Propyl 4-{3-[2-chloro-6-(trifluoromethyl)phenoxy]-1H-indazol-1-yl}-3-fluorobenzoate

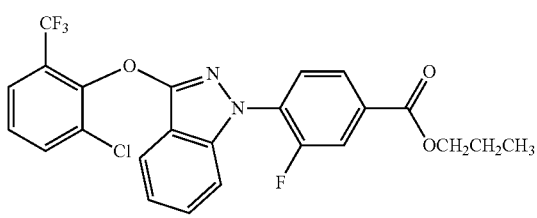

To a stirred solution of Example 7 (100 mg, 0.221 mmol) in n-propyl alcohol (5 mL) was added catalytic amount of sulfuric acid and the reaction mixture was refluxed for 18 hours. The mixture was cooled to RT and concentrated under reduced pressure. The residue was diluted with ethyl acetate (10 mL) and washed with sodium bicarbonate solution (10 mL). The organic layer was dried over anhydrous sodium sulfate and concentrated under reduced pressure. The residue thus obtained was purified by silica gel column chromatography to obtain 81 mg of the title product as off white solid. $^1$H NMR (300 MHz, DMSO-$d_6$) δ 0.97 (t, J=7.2 Hz, 3H), 1.73 (q, J=7.8 Hz, 2H), 4.26 (t, J=5.7 Hz, 2H), 7.36-7.40 (m, 1H), 7.45-7.52 (m, 1H), 7.62 (br s, 3H), 7.83-8.04 (m, 5H); ESI-MS (m/z) 493 (M+H)$^+$.

Example 47

Butyl 4-{3-[2-chloro-6-(trifluoromethyl)phenoxy]-1H-indazol-1-yl}-3-fluorobenzoate

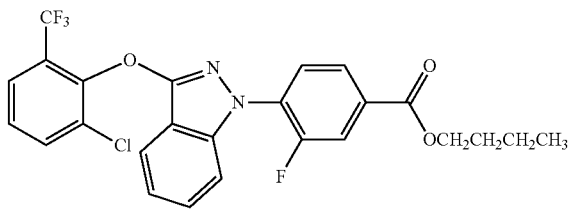

To a stirred solution of Example 7 (50 mg, 0.111 mmol) in DMF (4 mL) were added n-butyl bromide (24 μL, 0.222 mmol) and potassium carbonate (46 mg, 0.333 mmol) and the reaction mixture was heated to 90° C. for 3 hours. The reaction mixture was cooled to RT and poured in to water (10 mL) and the product was extracted with ethyl acetate (2×20 mL). The combined organic layers were washed with brine (20 mL) and dried over anhydrous sodium sulfate. The solvent was distilled off and the residue obtained was triturated with diethyl ether and n-pentane to give 43 mg of the title product as off white solid. $^1$H NMR (300 MHz, DMSO-$d_6$) δ 0.94 (t, J=7.2 Hz, 3H), 1.40 (br s, 2H), 1.69 (br s, 2H), 4.30 (br s, 2H), 7.35 (br s, 1H), 7.50 (br s, 1H), 7.61 (br s, 3H), 7.84-8.02 (m, 5H); ESI-MS (m/z) 507 (M+H)$^+$.

Example 48

Isopropyl 4-{3-[2-chloro-6-(trifluoromethyl)phenoxy]-1H-indazol-1-yl}-3-fluorobenzoate

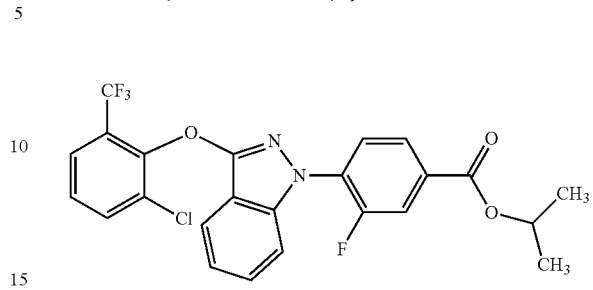

To a stirred solution of Example 7 (50 mg, 0.111 mmol) in DMF (4 mL) were added 2-bromopropane (21 μL, 0.222 mmol) and potassium carbonate (46 mg, 0.333 mmol) and the reaction mixture was heated to 90° C. for 3 hours. The reaction mixture was cooled to RT and poured in to water (10 mL) and the product was extracted with ethyl acetate (2×20 mL). The combined organic layers were washed with brine (20 mL) and dried over anhydrous sodium sulfate. The solvent was distilled off and the residue obtained was triturated with diethyl ether and n-pentane to give 43 mg of the title product as off white solid. $^1$H NMR (300 MHz, CDCl$_3$) δ 1.37 (d, J=6.3 Hz, 6H), 5.20-5.30 (m, 1H), 7.27-7.36 (m, 3H), 7.45-7.55 (m, 2H), 7.68 (t, J=8.7 Hz, 2H), 7.71-7.92 (m, 3H); APCI-MS (m/z) 493 (M+H)$^+$.

Pharmacological Activity

Biological Assay

The compounds described herein were screened for ROR gamma modulator activity using the TR-FRET assay by Lantha Screen as described in *JBC* 2011, 286, 26: 22707-10; and *Drug Metabolism and Disposition* 2009, 37, 10: 2069-78.

TR-FRET Assay for ROR Gamma

The assay is based on the principle that binding of the agonist to the ROR gamma causes a conformational change around helix 12 in the ligand binding domain, resulting in higher affinity for the co-activator peptide. ROR gamma being constitutively active, the Fluorescein-D22 co-activator peptide used in the assay is recruited in the absence of a ligand. Binding of the co-activator peptide, causes an increase in the TR-FRET signal while binding of an antagonist decreases the recruitment of the co-activator peptide, causing a decrease in the TR-FRET signal compared to control with no compound. The assay was performed using a two-step procedure, pre-incubation step with the compound followed by the detection step on addition of the anti-GST tagged terbium (Tb) and fluorescein tagged fluorophores as the acceptor.

Test compounds or reference compounds such as T0901317 (Calbiochem) were dissolved in dimethylsulfoxide (DMSO) to prepare 10.0 mM stock solutions and diluted to the desired concentration. The final concentration of DMSO in the reaction was 4% (v/v). The assay mixture was prepared by mixing 10 nM of the GST-tagged ROR gamma ligand binding domain (LBD) in the assay buffer containing 25 mM HEPES, 100 mM NaCl, 5 mM DTT and 0.01% BSA with or without the desired concentration of the compound.

The reaction was incubated at 22° C. for 1 hour. The pre-incubation step was terminated by addition of the detection mixture containing 300 nM Fluorescein-D22 co-activator peptide and 10 nM lantha screen Tb-anti GST antibody into the reaction mixture. After shaking for 5 minutes the reaction was further incubated for 1 hour at room temperature and read at 4° C. on an Infinite F500 reader as per the kit instructions (Invitrogen). The inhibition of test compound was calculated based on the TR-FRET ratio of 520/495. The activity was calculated as a percent of control reaction. $IC_{50}$ values were calculated from dose response curve by nonlinear regression analysis using GraphPad Prism software.

The compounds prepared were tested using the above assay procedure and the results obtained are given in Table 1. Percentage inhibition at concentrations of 1.0 M and 10.0 M are given in the table along with $IC_{50}$ (nM) details for selected examples. The compounds were found to have $IC_{50}$ less than 500 nM, preferably less than 100 nM, more preferably less than 50 nM.

The $IC_{50}$ (nM) values are set forth in Table 1 wherein "A" refers to an $IC_{50}$ value of less than 50 nM, "B" refers to $IC_{50}$ value in range of 50.01 to 100.0 nM and "C" refers to $IC_{50}$ values more than 100 nM.

TABLE 1

In-vitro Screening Results

| Sr. No | Example | % inhibition at 1 µM | % inhibition at 10 µM | $IC_{50}$ value (nM) |
|---|---|---|---|---|
| 1. | Example 1 | 89.97 | 96.26 | A |
| 2. | Example 2 | 96.88 | 98.43 | A |
| 3. | Example 3 | 23.45 | 34.59 | — |
| 4. | Example 4 | 31.22 | 36.98 | — |
| 5. | Example 5 | 98.44 | 99.0 | A |
| 6. | Example 6 | 99.16 | 99.58 | A |
| 7. | Example 7 | 95.26 | 94.76 | A |
| 8. | Example 8 | 96.43 | 98.16 | A |
| 9. | Example 9 | 86.45 | 96.89 | C |
| 10. | Example 10 | 100 | 100 | A |
| 11. | Example 11 | 98.06 | 97.75 | A |
| 12. | Example 12 | 94.41 | 95.11 | A |
| 13. | Example 13 | 91.69 | 91.71 | A |
| 14. | Example 14 | 91.38 | 91.17 | A |
| 15. | Example 15 | 76.38 | 95.85 | C |
| 16. | Example 16 | 96.05 | 97.21 | A |
| 17. | Example 17 | 84.89 | 95.97 | B |
| 18. | Example 18 | 80.97 | 94.54 | B |
| 19. | Example 19 | 94.48 | 94.87 | A |
| 20. | Example 20 | 95.65 | 100 | A |
| 21. | Example 21 | 92.24 | 92.44 | A |
| 22. | Example 22 | 96.82 | 99.29 | A |
| 23. | Example 23 | 98.15 | 96.72 | A |
| 24. | Example 24 | 95.79 | 97.79 | A |
| 25. | Example 25 | 96.28 | 94.25 | A |
| 26. | Example 26 | 31.30 | 33.68 | — |
| 27. | Example 27 | 95.61 | 97.9 | A |
| 28. | Example 28 | 30.18 | 62.89 | — |
| 29. | Example 29 | 96.86 | 94.27 | A |
| 30. | Example 30 | 47.11 | 88.92 | — |
| 31. | Example 31 | 96.56 | 91.56 | A |
| 32. | Example 32 | 94.58 | 90.44 | A |
| 33. | Example 33 | 98.14 | 94.10 | A |
| 34. | Example 34 | 96.87 | 92.03 | A |
| 35. | Example 35 | 92.26 | 89.17 | A |
| 36. | Example 36 | 95.67 | 96.43 | A |
| 37. | Example 37 | 97.56 | 94.62 | A |
| 38. | Example 38 | 96.84 | 93.45 | A |
| 39. | Example 39 | 15.41 | 24.99 | — |
| 40. | Example 40 | 9.11 | — | — |
| 41. | Example 41 | 5.13 | — | — |
| 42. | Example 42 | 0.61 | — | — |
| 43. | Example 43 | 6.99 | 1.02 | — |

TABLE 1-continued

In-vitro Screening Results

| Sr. No | Example | % inhibition at 1 µM | % inhibition at 10 µM | $IC_{50}$ value (nM) |
|---|---|---|---|---|
| 44. | Example 44 | 3.55 | 2.25 | — |
| 45. | Example 45 | 97.89 | 93.7 | B |
| 46. | Example 46 | 10.87 | 28.52 | — |
| 47. | Example 47 | 51.96 | 91.94 | — |
| 48. | Example 48 | 26.31 | 84.57 | — |

(—): Not determined

What is claimed is:

1. A compound of formula (I)

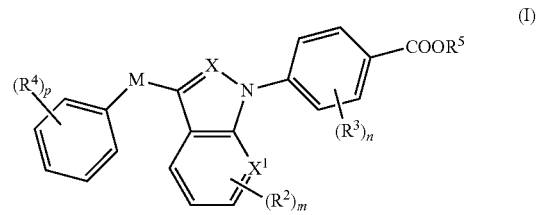

or a pharmaceutically acceptable salt thereof, wherein
M is selected from —O— and —C(O)—;
X is selected from N and CH;
$X^1$ is selected from N and CH;
each occurrence of $R^2$ is independently selected from halogen, hydroxyl and —CON(CH$_3$)$_2$;
each occurrence of $R^3$ is independently selected from halogen and hydroxyl;
each occurrence of $R^4$ is independently selected from halogen, $C_{1-8}$alkyl, halo$C_{1-8}$alkyl and $C_{3-6}$cycloalkyl;
$R^5$ is selected from hydrogen and $C_{1-4}$alkyl;
'm' is 0, 1, 2 or 3;
'n' is 0, 1, 2 or 3; and
'p' is 0, 1, 2, 3 or 4.

2. The compound according to claim 1, wherein
X is N or CH;
$X^1$ is N or CH;
each occurrence of $R^2$ is, independently F or —CON(CH$_3$)$_2$;
each occurrence of $R^3$ is F;
$R^5$ is hydrogen, —CH$_3$, —CH$_2$CH$_3$, —CH$_2$CH$_2$CH$_3$, —CH$_2$CH(CH$_3$)$_2$ or —CH$_2$CH$_2$CH$_2$CH$_3$;
'm' is 0 or 1;
'n' is 0 or 1; and

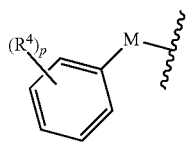

is phenoxy, 2-methylphenoxy, 3-methylphenoxy, 2-(trifluoromethyl)phenoxy, 2,6-dichlorophenoxy, 2-chloro-6-(trifluoromethyl)phenoxy, 4-chloro-2-(trifluoromethyl) phenoxy, 2-chloro-6-(difluoromethyl)phenoxy, 2-chloro-6-cyclopropylphenoxy, benzoyl, 2-fluorobenzoyl, 2-chlorobenzoyl, 2,6-dichlorobenzoyl, 2,6-difluorobenzoyl, 2-chloro-6-(trifluoromethyl)benzoyl or (2-chloro-6-cyclopropylphenyl)carbonyl.

3. The compound according to claim 1, wherein

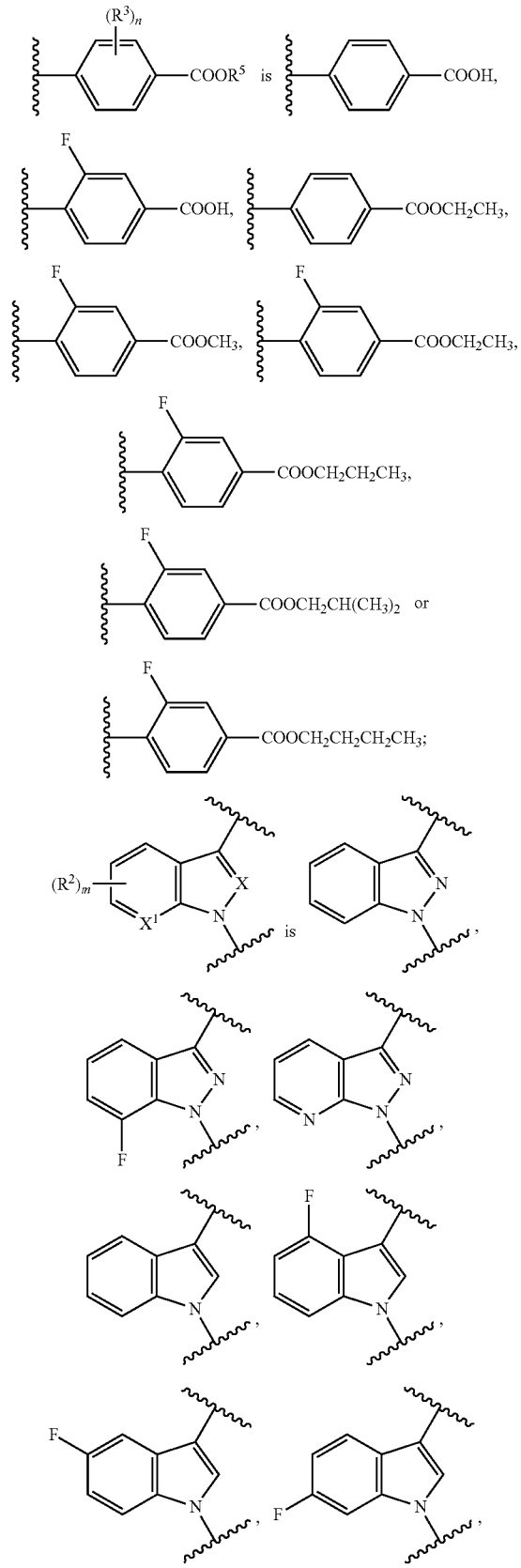

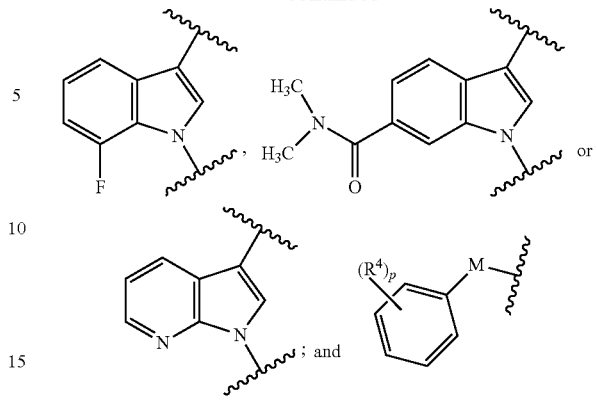

is phenoxy, 2-methylphenoxy, 3-methylphenoxy, 2-(trifluoromethyl)phenoxy, 2,6-dichlorophenoxy, 2-chloro-6-(trifluoromethyl)phenoxy, 4-chloro-2-(trifluoromethyl) phenoxy, 2-chloro-6-(difluoromethyl)phenoxy, 2-chloro-6-cyclopropylphenoxy, benzoyl, 2-fluorobenzoyl, 2-chlorobenzoyl, 2,6-dichlorobenzoyl, 2,6-difluorobenzoyl, 2-chloro-6-(trifluoromethyl)benzoyl or (2-chloro-6-cyclopropylphenyl)carbonyl.

4. The compound according to claim 1, wherein the compound has the formula (Ia)

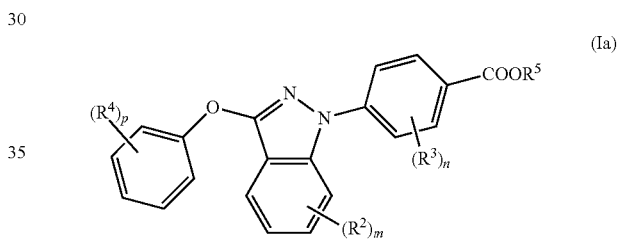

or a pharmaceutically acceptable salt thereof, wherein
each occurrence of $R^2$ is independently selected from halogen, hydroxyl and —$CON(CH_3)_2$;
each occurrence of $R^3$ is independently selected from halogen and hydroxyl;
each occurrence of $R^4$ is independently selected from halogen, $C_{1-8}$ alkyl, halo$C_{1-8}$ alkyl and $C_{3-6}$ cycloalkyl;
$R^5$ is selected from hydrogen and $C_{1-4}$alkyl;
'm' is 0, 1, 2 or 3;
'n' is 0, 1, 2 or 3; and
'p' is 0, 1, 2, 3 or 4.

5. The compound according to claim 1, wherein the compound has the formula (Ib)

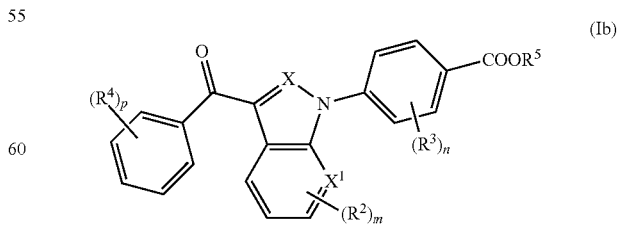

or a pharmaceutically acceptable salt thereof, wherein
X is selected from N and CH;
$X^1$ is selected from N and CH;

each occurrence of $R^2$ is independently selected from halogen, hydroxyl and —$CON(CH_3)_2$;

each occurrence of $R^3$ is independently selected from halogen and hydroxyl;

each occurrence of $R^4$ is independently selected from halogen, $C_{1-8}$ alkyl, halo$C_{1-8}$ alkyl and $C_{3-6}$ cycloalkyl;

$R^5$ is selected from hydrogen and $C_{1-4}$alkyl;

'm' is 0, 1, 2 or 3;

'n' is 0, 1, 2 or 3; and

'p' is 0, 1, 2, 3 or 4.

6. The compound according to claim 1, wherein the compound is selected from

4-[3-(2-Methylphenoxy)-1H-indazol-1-yl]benzoic acid;

4-{3-[2-(Trifluoromethyl)phenoxy]-1H-indazol-1-yl}benzoic acid;

4-[3-(3-Methylphenoxy)-1H-indazol-1-yl]benzoic acid;

4-(3-Phenoxy-1H-indazol-1-yl)benzoic acid;

4-[3-(2,6-Dichlorophenoxy)-1H-indazol-1-yl)benzoic acid;

4-[3-(2,6-Dichlorophenoxy)-1H-indazol-1-yl]-3-fluorobenzoic acid;

4-{3-[2-Chloro-6-(trifluoromethyl)phenoxy]-1H-indazol-1-yl}-3-fluorobenzoic acid;

3-Fluoro-4-{3-[2-(trifluoromethyl)phenoxy]-1H-indazol-1-yl}benzoic acid;

4-{3-[4-Chloro-2-(trifluoromethyl)phenoxy]-1H-indazol-1-yl}-3-fluorobenzoic acid;

4-{3-[2-Chloro-6-(difluoromethyl)phenoxy]-1H-indazol-1-yl}-3-fluorobenzoic acid;

4-[3-(2,6-Dichlorophenoxy)-7-fluoro-1H-indazol-1-yl]-3-fluorobenzoic acid;

4-{3-[2-Chloro-6-(difluoromethyl)phenoxy]-7-fluoro-1H-indazol-1-yl}-3-fluorobenzoic acid;

4-[3-(2-Chloro-6-cyclopropylphenoxy)-1H-indazol-1-yl]-3-fluorobenzoic acid;

4-[3-(2-Chloro-6-cyclopropylphenoxy)-7-fluoro-1H-indazol-1-yl]-3-fluorobenzoic acid;

4-{3-[(2-Fluorophenyl)carbonyl]-1H-indol-1-yl}benzoic acid;

4-{3-[(2,6-Dichlorophenyl)carbonyl]-1H-indol-1-yl}benzoic acid;

4-{3-[(2-Chlorophenyl)carbonyl]-1H-indol-1-yl}benzoic acid;

4-{3-[(2,6-Difluorophenyl)carbonyl]-1H-indol-1-yl}benzoic acid;

4-{3-[(2,6-Dichlorophenyl)carbonyl]-1H-indol-1-yl}-3-fluorobenzoic acid;

4-{3-[(2-Chlorophenyl)carbonyl]-1H-indol-1-yl}-3-fluorobenzoic acid;

4-{3-[2-Chloro-6-(trifluoromethyl)benzoyl]-1H-indol-1-yl}-3-fluorobenzoic acid;

4-[3-(2,6-Dichlorobenzoyl)-4-fluoro-1H-indol-1-yl]-3-fluorobenzoic acid;

4-[3-(2,6-Dichlorobenzoyl)-5-fluoro-1H-indol-1-yl]-3-fluorobenzoic acid;

4-[3-(2,6-Dichlorobenzoyl)-6-fluoro-1H-indol-1-yl]-3-fluorobenzoic acid;

4-[3-(2,6-Dichlorobenzoyl)-7-fluoro-1H-indol-1-yl]-3-fluorobenzoic acid;

4-[3-(2,6-Dichloro-benzoyl)-6-dimethylcarbamoyl-indol-1-yl]-3-fluoro-benzoic acid;

4-[3-(2,6-Dichlorobenzoyl)-1H-pyrrolo[2,3-b]pyridin-1-yl]-3-fluorobenzoic acid;

4-[3-(Phenylcarbonyl)-1H-indazol-1-yl]benzoic acid;

4-[3-(2,6-Dichlorobenzoyl)-1H-indazol-1-yl]benzoic acid;

4-(3-Benzoyl-1H-indazol-1-yl)-3-fluorobenzoic acid;

4-[3-(2,6-Dichlorobenzoyl)-1H-indazol-1-yl]-3-fluorobenzoic acid;

4-{3-[(2,6-Dichlorophenyl)carbonyl]-7-fluoro-1H-indazol-1-yl}benzoic acid;

4-(3-{[2-Chloro-6-(trifluoromethyl)phenyl]carbonyl}-1H-indazol-1-yl)-3-fluorobenzoic acid;

4-(3-{[2-Chloro-6-(trifluoromethyl)phenyl]carbonyl}-1H-indazol-1-yl)-benzoic acid;

4-{3-[(2-Chloro-6-cyclopropylphenyl)carbonyl]-7-fluoro-1H-indazol-1-yl}benzoic acid;

4-{3-[(2,6-Dichlorophenyl)carbonyl]-1H-pyrazolo[3,4-b]pyridin-1-yl}benzoicacid;

4-{3-[(2-Chloro-6-cyclopropylphenyl)carbonyl]-1H-pyrazolo[3,4-b]pyridin-1-yl}benzoic acid;

4-(3-{[2-Chloro-6-(trifluoromethyl)phenyl]carbonyl}-1H-pyrazolo[3,4-b]pyridin-1-yl)benzoic acid;

Ethyl 4-{3-[(2,6-dichlorophenyl)carbonyl]-1H-indol-1-yl}-3-fluorobenzoate;

Propyl 4-{3-[(2,6-dichlorophenyl)carbonyl]-1H-indol-1-yl}-3-fluorobenzoate;

Butyl 4-{3-[(2,6-dichlorophenyl)carbonyl]-1H-indol-1-yl}-3-fluorobenzoate;

Ethyl 4-[3-(2,6-dichloro-benzoyl)-7-fluoro-1H-indol-1-yl]-3-fluorobenzoate;

Propyl 4-[3-(2,6-dichloro-benzoyl)-7-fluoro-1H-indol-1-yl]-3-fluorobenzoate;

Butyl 4-[3-(2,6-dichloro-benzoyl)-7-fluoro-1H-indol-1-yl]-3-fluorobenzoate;

Ethyl 4-{3-[2-chloro-6-(trifluoromethyl)phenoxy]-1H-indazol-1-yl}-3-fluorobenzoate;

Propyl 4-{3-[2-chloro-6-(trifluoromethyl)phenoxy]-1H-indazol-1-yl}-3-fluorobenzoate;

Butyl 4-{3-[2-chloro-6-(trifluoromethyl)phenoxy]-1H-indazol-1-yl}-3-fluorobenzoate;

Isopropyl 4-{3-[2-chloro-6-(trifluoromethyl)phenoxy]-1H-indazol-1-yl}-3-fluorobenzoate;

and pharmaceutically acceptable salt thereof.

7. The compound according to claim 1, wherein the compound has the formula

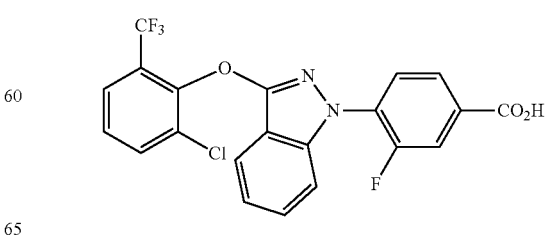

or a pharmaceutically acceptable salt thereof.

8. The compound according to claim 1, wherein the compound has the formula

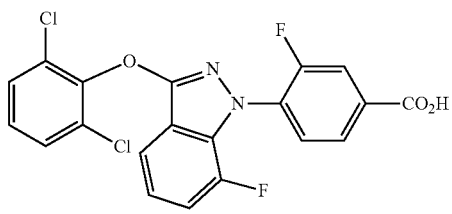 [SMILES: O=C(O)c1ccc(-n2nc(Oc3c(Cl)cccc3Cl)c3cccc(F)c32)c(F)c1]

or a pharmaceutically acceptable salt thereof.

9. The compound according to claim 1, wherein the compound has the formula

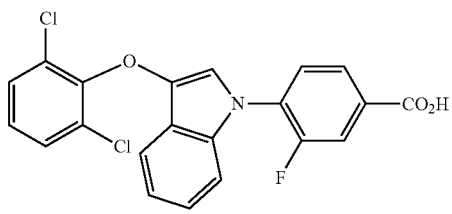 [SMILES: O=C(O)c1ccc(-n2cc(Oc3c(Cl)cccc3Cl)c3ccccc32)c(F)c1]

or a pharmaceutically acceptable salt thereof.

10. The compound according to claim 1, wherein the compound has the formula

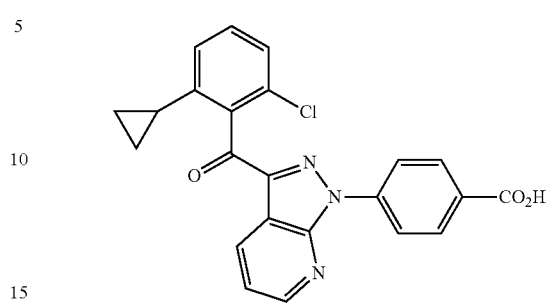

or a pharmaceutically acceptable salt thereof.

11. A pharmaceutical composition comprising a compound according to claim 1 and a pharmaceutically acceptable excipient, wherein the pharmaceutically acceptable excipient is a carrier or diluent.

* * * * *